US011542545B2

(12) United States Patent
Ismagilov et al.

(10) Patent No.: US 11,542,545 B2
(45) Date of Patent: Jan. 3, 2023

(54) MICROFLUIDIC MEASUREMENTS OF THE RESPONSE OF AN ORGANISM TO A DRUG

(71) Applicants: CALIFORNIA INSTITUTE OF TECHNOLOGY, Pasadena, CA (US); Talis Biomedical Corporation, Redwood City, CA (US)

(72) Inventors: Rustem F. Ismagilov, Altadena, CA (US); Eugenia Khorosheva, South Pasadena, CA (US); Travis S. Schlappi, Pasadena, CA (US); Matthew S. Curtis, Pasadena, CA (US); Nathan G. Schoepp, Pasadena, CA (US); Hedia Maamar, San Jose, CA (US); Feng Shen, San Jose, CA (US); Erik B. Jue, Pasadena, CA (US)

(73) Assignees: California Institute of Technology, Pasadena, CA (US); Talis Biomedical Corporation, Redwood City, CA (US)

(*) Notice: Subject to any disclaimer, the term of this patent is extended or adjusted under 35 U.S.C. 154(b) by 170 days.

(21) Appl. No.: 15/524,449

(22) PCT Filed: Nov. 5, 2015

(86) PCT No.: PCT/US2015/059344
§ 371 (c)(1),
(2) Date: May 4, 2017

(87) PCT Pub. No.: WO2016/085632
PCT Pub. Date: Jun. 2, 2016

(65) Prior Publication Data
US 2018/0274020 A1 Sep. 27, 2018

Related U.S. Application Data

(60) Provisional application No. 62/075,648, filed on Nov. 5, 2014.

(51) Int. Cl.
*C12Q 1/6851* (2018.01)
*C12Q 1/689* (2018.01)
*C12Q 1/6809* (2018.01)
*C12Q 1/18* (2006.01)
*C12Q 1/686* (2018.01)
*B01L 3/00* (2006.01)
*B01L 7/00* (2006.01)

(52) U.S. Cl.
CPC ...... *C12Q 1/6851* (2013.01); *B01L 3/502715* (2013.01); *B01L 7/00* (2013.01); *C12Q 1/18* (2013.01); *C12Q 1/686* (2013.01); *C12Q 1/689* (2013.01); *C12Q 1/6809* (2013.01); *B01L 2300/0861* (2013.01); *C12Q 2600/136* (2013.01); *C12Q 2600/158* (2013.01)

(58) Field of Classification Search
CPC .... C12Q 1/18; C12Q 2600/136; C12Q 1/689; C12Q 2545/114; C12Q 1/6851; C12Q 1/686; C12Q 2600/158
See application file for complete search history.

(56) References Cited

U.S. PATENT DOCUMENTS

| | | | |
|---|---|---|---|
| 5,789,173 A | 8/1998 | Peck et al. | |
| 6,153,400 A | 11/2000 | Matsumura et al. | |
| 6,391,577 B1 | 5/2002 | Mikkelsen et al. | |
| 7,728,119 B2 | 6/2010 | Nakamura et al. | |
| 8,476,063 B2 | 7/2013 | Jovanovich et al. | |
| 9,133,498 B2 | 9/2015 | Kwon et al. | |
| 9,415,392 B2 | 8/2016 | Ismagilov et al. | |
| 9,447,461 B2 | 9/2016 | Ismagilov et al. | |
| 9,464,319 B2 | 10/2016 | Ismagilov et al. | |
| 9,493,826 B2 | 11/2016 | Ismagilov et al. | |
| 9,687,845 B2 | 6/2017 | Weibel et al. | |
| 9,803,237 B2 | 10/2017 | Ismagilov et al. | |
| 9,808,798 B2 | 11/2017 | Ismagilov et al. | |
| 9,822,356 B2 | 11/2017 | Ismagilov et al. | |
| 10,196,684 B2 | 2/2019 | Ismagilov et al. | |
| 2005/0095665 A1 | 5/2005 | Williams et al. | |
| 2007/0190531 A1 | 8/2007 | Mitani et al. | |
| 2009/0143233 A1 | 6/2009 | Knight et al. | |
| 2009/0181395 A1 | 7/2009 | Becker et al. | |
| 2011/0269130 A1 | 11/2011 | Shi et al. | |
| 2012/0010091 A1 | 1/2012 | Linnarson | |
| 2012/0028342 A1 | 2/2012 | Ismagilov et al. | |
| 2012/0100551 A1 | 4/2012 | Kojima et al. | |
| 2012/0322058 A1 | 12/2012 | Regan et al. | |
| 2012/0329038 A1 | 12/2012 | Ismagilov et al. | |
| 2013/0052653 A1 | 2/2013 | Stein et al. | |

(Continued)

FOREIGN PATENT DOCUMENTS

CN 103003446 A 3/2013
KR 10-2012-0133385 A 12/2012

(Continued)

OTHER PUBLICATIONS

Beuving et al., "Antibiotic Susceptibility Testing of Grown Blood Cultures by Combining Culture and Real-Time Polymerase Chain Reaction Is Rapid and Effective," PLoS One, December, vol. 6, No. 2, e27689, pp. 1-6. (Year: 2011).*
Pholwat et al., "Digital PCR to Detect and Quantify Heteroresistance in Drug Resistant *Mycobacterium tuberculosis*," PLoS One, February, vol. 8, No. 2, e57238, pp. 10. (Year: 2013).*
Hindson et al., "Absolute quantification by droplet digital PCR versus analog real-time PCR", Nature Methods, October, vol. 10, No. 10, pp. 1003-1005; and On-line methods pp. 1-3. (Year: 2013).*
Assmann, et al. "Identification of vancomycin interaction with Enterococcus faecalis within 30 min of interaction time using Raman spectroscopy", Anal. Bioanal. Chem., vol. 407, 2015, pp. 8343-8352.

(Continued)

*Primary Examiner* — Young J Kim
(74) *Attorney, Agent, or Firm* — Shay Glenn LLP

(57) ABSTRACT

Disclosed herein are methods and devices for rapid assessment of whether a microorganism present in a sample is susceptible or resistant to a treatment.

20 Claims, 19 Drawing Sheets
Specification includes a Sequence Listing.

(56) References Cited

U.S. PATENT DOCUMENTS

| | | |
|---|---|---|
| 2013/0190196 A1 | 7/2013 | Onderdonk et al. |
| 2013/0281316 A1 | 10/2013 | Ismagilov et al. |
| 2013/0288249 A1 | 10/2013 | Gullberg et al. |
| 2013/0309679 A1 | 11/2013 | Ismagilov et al. |
| 2014/0278136 A1 | 9/2014 | Shamsheyeva et al. |
| 2014/0308663 A1 | 10/2014 | Yonekawa et al. |
| 2014/0323340 A1 | 10/2014 | Goldberg et al. |
| 2014/0336064 A1 | 11/2014 | Ismagilov et al. |
| 2015/0159205 A1 | 6/2015 | Narayanan et al. |
| 2015/0225803 A1 | 8/2015 | Ismagilov et al. |
| 2015/0247190 A1 | 9/2015 | Ismagilov et al. |
| 2015/0267266 A1 | 9/2015 | Soetaert et al. |
| 2016/0160268 A1 | 6/2016 | Haake et al. |
| 2016/0256870 A1 | 9/2016 | Ismagilov et al. |
| 2016/0263577 A1 | 9/2016 | Ismagilov et al. |
| 2016/0288121 A1 | 10/2016 | Ismagilov et al. |
| 2016/0362734 A1 | 12/2016 | Ismagilov et al. |
| 2017/0152553 A1 | 6/2017 | Ismagilov et al. |
| 2017/0225161 A1 | 8/2017 | Begolo et al. |
| 2019/0352705 A1 | 11/2019 | Ismagilov et al. |

FOREIGN PATENT DOCUMENTS

| | | |
|---|---|---|
| WO | 2004009849 A1 | 1/2004 |
| WO | 2010091111 A1 | 8/2010 |
| WO | 2012016357 A1 | 8/2010 |
| WO | WO 2010/117620 A2 | 10/2010 |
| WO | 2011106536 A2 | 9/2011 |
| WO | 2012109500 A2 | 8/2012 |
| WO | WO 2013/130875 A1 | 9/2013 |
| WO | WO 2013/159116 A1 | 10/2013 |
| WO | WO 2013/159117 A1 | 10/2013 |
| WO | WO 2014/055963 A1 | 4/2014 |
| WO | WO 2014/172688 A1 | 10/2014 |
| WO | WO 2015/009967 A1 | 1/2015 |
| WO | WO 2015013324 | 1/2015 |
| WO | WO 2015/058008 A2 | 4/2015 |
| WO | WO 2015/084458 A2 | 6/2015 |
| WO | WO 2016/011280 A1 | 1/2016 |
| WO | WO 2016/085632 A2 | 6/2016 |

OTHER PUBLICATIONS

Barczak, et al. "RNA signatures allow rapid identification of pathogens and antibiotic susceptibilities" PNAS, vol. 109, No. 16, 2012, pp. 6217-6222.

Bernhardt, et al. "Detection of Bacteria in Blood by Centrifugation and Filtration" J. Clinical Microbiology, vol. 29, No. 3, 1991, pp. 422-425.

Besant, et al. "Rapid electrochemical phenotypic profiling of antibiotic-resistant bacteria" Lab Chip, vol. 15, May 2015, pp. 2799-2807.

Beuving, et al. "Antibiotic Susceptibility Testing of Grown Blood Cultures by Combining Culture and Real-Time Polymerase Chain Reaction Is Rapid and Effective" PLoS ONE, vol. 6, No. 12, 2011, pp. e27689.

Blattner, et al. "The Complete Genome Sequence of *Escherichia coli* K-12" Science, vol. 277, 1997, pp. 1453-1462.

Boedicker, et al. "Microfluidic Confinement of Single Cells of Bacteria in Small Volumes Initiates High-Density Behavior of Quorum Sensing and Growth and Reveals Its Variability" Agnew. Chem. Int. Ed., vol. 48, 2009, pp. 5908-5911. Including Supporting Information.

Brunschede, et al. "Establishment of exponential growth after a nutritional shift-up in *Escherichia coli* B/r: Accumulation of deoxyribonucleic acid, ribonucleic acid, and protein" J. Bacteriology, vol. 129, No. 2, 1977, pp. 1020-1033.

Cartron, et al. "Feo—Transport of ferrous iron into bacteria" BioMetals, vol. 19, 2006, pp. 143-157.

Churski, et al. "Rapid screening of antibiotic toxicity in an automated microdroplet system" Lab Chip, vol. 12, 2012, pp. 1629-1637.

Cirz, et al. "Inhibition of Mutation and Combating the Evolution of Antibiotic Resistance" PLoS Biology, vol. 3, No. 6, 2005, p. e176.

Couturier and Rocha. "Replication-associated gene dosage effects shape the genomes of fast-growing bacteria but only fortranscription and translation genes" Molecular Microbiology, vol. 59, No. 5, 2006, pp. 1506-1518.

Donachie and Blakely. "Coupling the initiation of chromosome replication to cell size in *Escherichia coli*" Cur. Opin. Microbiology, vol. 6, 2003, pp. 146-150.

Drlica and Zhao. "DNA gyrase, topoisomerase IV, and 4-quinolones" Microbiol. Mol. Biology Rev., vol. 61, No. 3, 1997, pp. 377-392.

Dwyer, et al. "Antibiotics induce redox-related physiological alterations as part of their lethality" PNAS, vol. 111, No. 20, May 2014, pp. E100-E109.

Fossum, et al. "Organization of sister origins and replisomes during multifork DNA replication in *Escherichia coli*" EMBO Journal, vol. 26, 2007, pp. 4514-4522.

Geiss, et al. "Direct multiplexed measurement of gene expression with color-coded probe pairs" Nature Biotech., vol. 26, No. 3, 2008, pp. 317-325. Including Corrigendum.

Hagiwara, et al. "A Genome-Wide View of *Escherichia coli* BasS-BasR Two-component System Implicated in Iron-responses" Bioscience, Biotechnology and Biochemistry, vol. 68, No. 8, 2004, pp. 1758-1767.

Halford, et al. "Rapid Antimicrobial Susceptibility Testing by Sensitive Detection of Precursor rRNA Using a Novel Electrochemical Biosensing Platform" Antimicrobial Agents and Chemotherapy, vol. 57, No. 2, 2013, pp. 936-943.

Hou, et al. "Direct detection and drug-resistance profiling of bacteremias using inertial microfluidics" Lab Chip, vol. 15, 2015, pp. 2297-2307.

Jeon, et al. "RstA-Promoted Expression of the Ferrous Iron Transporter FeoB under Iron-Replete Conditions Enhances Fur Activity in *Salmonella enterica*" J. Bacteriology, vol. 190, No. 2, 2008, pp. 7326-7334.

Joshi, et al. "*Escherichia coli* sister chromosome separation includes an abrupt global transition with concomitant release of late-splitting intersister snaps" PNAS, vol. 108, No. 7, 2011, pp. 2765-2770.

Kang, et al. "An extracorporeal blood-cleansing device for sepsis therapy" Nature Med., vol. 20, No. 10, Oct. 2014, pp. 1211-1216.

Kang, et al. "Rapid detection of single bacteria in unprocessed blood using Integrated Comprehensive Droplet Digital Detection" Nature Communications, Nov. 2014, pp. 1-10.

Kempf, et al. "Fluorescent In Situ Hybridization Allows Rapid Identification of Microorganisms in Blood Cultures" J. Clin. Microbiol., vol. 38, No. 2, 2000, pp. 830-838.

Kostic, et al. "Thirty-minute screening of antibiotic resistance genes in bacterial isolates with minimal sample preparation in static self-dispensing 64 and 384 assay cards" Appl Microbiol Biotechnol, vol. 99, No. 18, Jul. 2015, pp. 7711-7722.

Kreutz et al., "Theoretical Design and Analysis of Multivolume Digital Assays with Wide Dynamic Range Validated Experimentally with Microfluidic Digital PCR", Anal. Chem., 2011, vol. 83, pp. 8158-8168.

Kubitschek and Freedman "Chromosome Replication and the Division Cycle of *Escherichia coli* B/r" J. Bacteriology, vol. 107, No. 1, 1971, pp. 95-99.

Lehman, et al. "A multiplex real-time PCR assay for rapid detection and differentiation of 25 bacterial and fungal pathogens from whole blood samples" Med Microbiol Immunol, vol. 197, 2008, pp. 313-324.

Lobritz, et al. "Antibiotic efficacy is linked to bacterial cellular respiration" PNAS, vol. 12, No. 27, Jul. 2015, pp. 8173-8180.

Ma, et al. "Gene-targeted microfluidic cultivation validated by isolation of a gut bacterium listed in Human Microbiome Project's Most Wanted taxa" PNAS, vol. 111, No. 27, Jul. 2014, pp. 9768-9773.

Ma, et al. "Individually addressable arrays of replica microbial cultures enabled by splitting SlipChips" Integr Biol, vol. 6, 2014, pp. 796-805. Including Supporting Information.

Mach, et al. "A Biosensor Platform for Rapid Antimicrobial Susceptibility Testing Directly from Clinical Samples" J Urol, vol. 185, No. 1, 2011, pp. 148-153.

(56) References Cited

OTHER PUBLICATIONS

Mann and Mikkelson "Antibiotic Susceptibility Testing at a Screen-Printed Carbon Electrode Array" Anal Chem, vol. 80, 2008, pp. 843-848.
Mezger, et al. "A General Method for Rapid Determination of Antibiotic Susceptibility and Species in Bacterial Infections" J Clin Microbiology, vol. 53, No. 2, Feb. 2015, pp. 425-432.
Millar, et al. "A simple and sensitive method to extract bacterial, yeast and fungal DNA from blood culture material" J Microbiol Methods, vol. 42, 2000, pp. 139-147.
Rolain, et al. "Real-time PCR for universal antibiotic susceptibility testing" Brit. J. Antimicrobial Chemotherapy, vol. 54, 2004, pp. 538-541.
Shen, et al. "Digital PCR on a SlipChip" Lab Chip, vol. 10, 2010, pp. 2666-2672.
Shishkin, et al. "Simultaneous generation of many RNA-seq libraries in a single reaction." Nat Meth, vol. 12, 2014, pp. 323-325.
Slager, et al. "Antibiotic-induced replication stress triggers bacterial competence by increasing gene dosage near the origin." Cell, vol. 157, 2014, pp. 395-406.
Tamayo, et al. "Rapid assessment of the effect of ciprofloxacin on chromosomal DNA from *Escherichia coli* using an in situ DNA fragmentation assay." BMC Microbiol, vol. 9, 2009, p. 69.
Touati, et al. "Lethal oxidative damage and mutagenesis are generated by iron in delta-fur mutants of *Escherichia coli*: Protective role of superoxide dismutase." J Bacter, vol. 177, 1995, pp. 2305-2314.
Weaver, et al. "Taking qPCR to a higher level: Analysis of CNV reveals the power of high throughput qPCR to enhance quantitative resolution." Methods, vol. 50, 2010, pp. 271-276.
Wecke and Mascher "Antibiotic research in the age of omics: from expression profiles to interspecies communication." J. Antimicrob Chemo, vol. 66, 2011, pp. 2689-2704.
Wiesinger-Mayr et al. "Establishment of a semi-automated pathogen DNA isolation from whole blood and comparison with commercially available kits" J Microbiol Methods, vol. 85, 2011, pp. 206-213.
Zierdt, et al. "Development of lysis-filtration blood culture technique." J Clin Microbiol, vol. 5, 1977, pp. 46-50.
Zierdt "Simplified Lysed-Blood Culture Technique" J Clin Microbiol, vol. 23, No. 3, 1986, pp. 452-455.
Boedicker, J et al., "Detecting Bacteria and Determining their Susceptibility to Antibiotics by Stochastic Confinement in Nanoliter Droplets using Plug-Based Microfluidics," Lab on a Chip, vol. 8, No. 8, Jan. 1, 2008, p. 1265-1272.
Chantell C., "Multiplexed automated digital microscopy for rapid identification and antimicrobial susceptibility testing of bacteria and yeast directly from clinical samples," Clinical Microbiology Newsletter, Oct. 15, 2015, vol. 37, No. 20, pp. 161-167.
Choi, J., et al., "A rapid antimicrobial susceptibility test based on single-cell morphological analysis," Sci Transl Med., Dec. 17, 2014, vol. 6, No. 267, 267ra174, pp. 1-15.
Davies, J., et al., "Origins and evolution of antibiotic resistance," Microbiol Mol Biol Rev., Sep. 2010, vol. 74, No. 3, pp. 417-433.
Douglas, I.S., et al., "Rapid automated microscopy for microbiological surveillance of ventilator-associated pneumonia," Am J Respir Crit Care Med., Mar. 1, 2015, vol. 191, No. 5, pp. 566-573.
Ertl, P., et al., "Rapid antibiotic susceptibility testing via electrochemical measurement of ferricyanide reduction by *Escherichia coli* and Clostridium sporogenes," Anal Chem., Oct. 15, 2000, vol. 72, No. 20, pp. 4957-4964.
European Patent Office, Extended European Search Report, EP Patent Application No. 15862888.3, dated Jul. 9, 2018, nine pages.
Fredborg, M., et al., "Real-time optical antimicrobial susceptibility testing," J Clin Microbiol., Jul. 2013, vol. 51, No. 7, pp. 2047-2053.
Halford, C., et al., "Rapid antimicrobial susceptibility testing by sensitive detection of precursor rRNA using a novel electrochemical biosensing platform," Antimicrob Agents Chemother., Feb. 2013, vol. 57, No. 2, pp. 936-943.

Ikeuchi, T., et al., "PCR-based method for rapid and minimized electrochemical detection of mecA gene of methicillin-resistant *Staphylococcus aureus* and methicillin-resistant *Staphylococcus epidermidis*," General Medicine: Open Access. 2015, vol. 3, No. 6, pp. 1-5.
Intellectual Property Office of Singapore, Invitation to Respond to Written Opinion and Search Report, Singapore Patent Application No. 11201703695V, dated May 8, 2018, ten pages.
Jorgensen, J.H., et al., "Antimicrobial susceptibility testing: a review of general principles and contemporary practices," Clin Infect Dis., Dec. 2009, vol. 49, No. 11, pp. 1749-1755.
Kostic, T., et al., "Thirty-minute screening of antibiotic resistance genes in bacterial isolates with minimal sample preparation in static self-dispensing 64 and 384 assay cards," Appl Microbiol Biotechnol., Jul. 31, 2015, vol. 99, No. 18, pp. 7711-7722.
Kumar, A., et al., "Duration of hypotension before initiation of effective antimicrobial therapy is the critical determinant of survival in human septic shock," Crit Care Med. 2006, vol. 34, No. 6, pp. 1589-1596.
Kurosaki, Y., et al., "Development and Evaluation of Reverse Transcription-Loop-Mediated Isothermal Amplification (RT-LAMP) Assay Coupled with a Portable Device for Rapid Diagnosis of Ebola Vims Disease in Guinea," PLoS Negl Trop Dis., Feb. 22, 2016, vol. 10, No. e0004472, pp. 1-12.
Marston, H.D., et al., "Antimicrobial Resistance," JAMA. Sep. 20, 2016, vol. 316, No. 11, pp. 1193-1204.
PCT International Search Report and Written Opinion for PCT/US17/53338, dated Jan. 30, 2018, 25 Pages.
PCT International Search Report and Written Opinion for PCT/US2017/061403, dated Feb. 13, 2018, 16 Pages.
PCT Invitation to Pay Additional Fees for PCT/US17/53338, dated Nov. 30, 2017, 3 Pages.
Peterson, L.R., et al., "Methicillin-Resistant *Staphylococcus aureus* Control in the 21st Century Laboratory Involvement Affecting Disease Impact and Economic Benefit from Large Population Studies," J Clin Microbiol., Nov. 2016, vol. 54, No. 11, pp. 2647-2654.
Schlappi, T., et al., "Flow-through Capture and in Situ Amplification Can Enable Rapid Detection of a Few Single Molecules of Nucleic Acids from Several Milliliters of Solution." Analytical Chemistry, Jul. 2016, vol. 88, No. 15, pp. 7647-7653.
Schoepp, N.G., et al., "Digital Quantification of DNA Replication and Chromosome Segregation Enables Determination of Antimicrobial Susceptibility after only 15 Minutes of Antibiotic Exposure," Angew Chern Int Ed Engl., 2016, vol. 55, No. 33, pp. 9557-9561.
Shen, F., et al., "Digital Isothermal Quantification of Nucleic Acids via Simultaneous Chemical Initiation of Recombinase Polymerase Amplification Reactions on SlipChip," Analytical Chemistry, Apr. 8, 2011, vol. 83, pp. 3533-3540.
Shen, F., et al., "Nanoliter multiplex PCR arrays on a SlipChip," Analytical chemistry, Jun. 1, 2010, vol. 82, No. 11, pp. 4606-4612.
Spencer, M., et al., "A primer on on-demand polymerase chain reaction technology," Am J Infect Control. 2015, vol. 43, No. 10, pp. 1102-1108.
Steinberger-Levy, I., et al., "A Rapid Molecular Test for Determining Yersinia pestis Susceptibility to Ciprofloxacin by the Quantification of Differentially Expressed Marker Genes," Frontiers in Microbiology, May 2016, vol. 7, pp. 1-13.
Van Der Zee, A., et al., "Review of a major epidemic of methicillin-resistant *Staphylococcus aureus*: the costs of screening and consequences of outbreak management," Am J Infect Control. 2013, vol. 41, No. 3, pp. 204-209.
Whale, A. S., et al., "Comparison of microfluidic digital PCR and conventional quantitative PCR for measuring copy number variation," Nucleic Acids Res., Feb. 28, 2012, vol. 40, No. 11, e82, pp. 1-9.
Zboromyrska, Y., et al., "Rapid detection of beta-lactamases directly from positive blood cultures using a loop-mediated isothermal amplification (LAMP)-based assay," Int J Antimicrob Ag., Mar. 4, 2015, vol. 46, No. 3, pp. 355-356.

(56) References Cited

OTHER PUBLICATIONS

PCT International Search Report & Witten Opinion, International Application No. PCT/US2015/059344, dated Jul. 12, 2016, 20 Pages.

PCT International Search Report and Written Opinion, International Application No. PCT/US2014/060977, dated Apr. 23, 2015, 17 Pages.

Joneja, A., et al., "Linear nicking endonuclease-mediated strand displacement DNA amplification," Anal Biochem., 2011, pp. 58-69, vol. 414, No. 1.

Wang, Y., et al., "A one-step reverse transcription loop-mediated isothermal amplification for detection and discrimination of infectious bursal disease virus," Virology Journal, 2011, pp. 1-7, vol. 8, No. 108.

Boedicker et al.; Detecting bacteria and determining their susceptibility to antibiotics by stochastic confinement in nanoliter droplets using plug-based microfluidics; Lab on Chip; 8(8); pp. 1265-1272; Jul. 2008.

Karlin-Neumann; Enabling cancer research and treatment with droplet-based digital PCR technology; American Laboratory; 46(7); pp. 27-29; retrieved from the internet (https://www.americanlaboratory.com/914-Application-Notes/167485-Enabling-Cancer-Research-and-Treatment-With-Droplet-Based-Digital-PCR-Technologyh): 4 pages; Sep. 2014.

Porensky et al.; A single administrarion of morpholino antisense oligomer rescues spinal muscular atrophy in mouse; Human Molecular Genetics; 21(7); pp. 1625-1638; Apr. 2012.

Yung et al.; Single-molecule detection of epidermal growth factor receptor mutations in plasma by microfluidics digtal PCR in non-small cell lung cancer patients: Clinical Cancer Research: 15(6); pp. 2076-2084; Mar. 2009.

\* cited by examiner

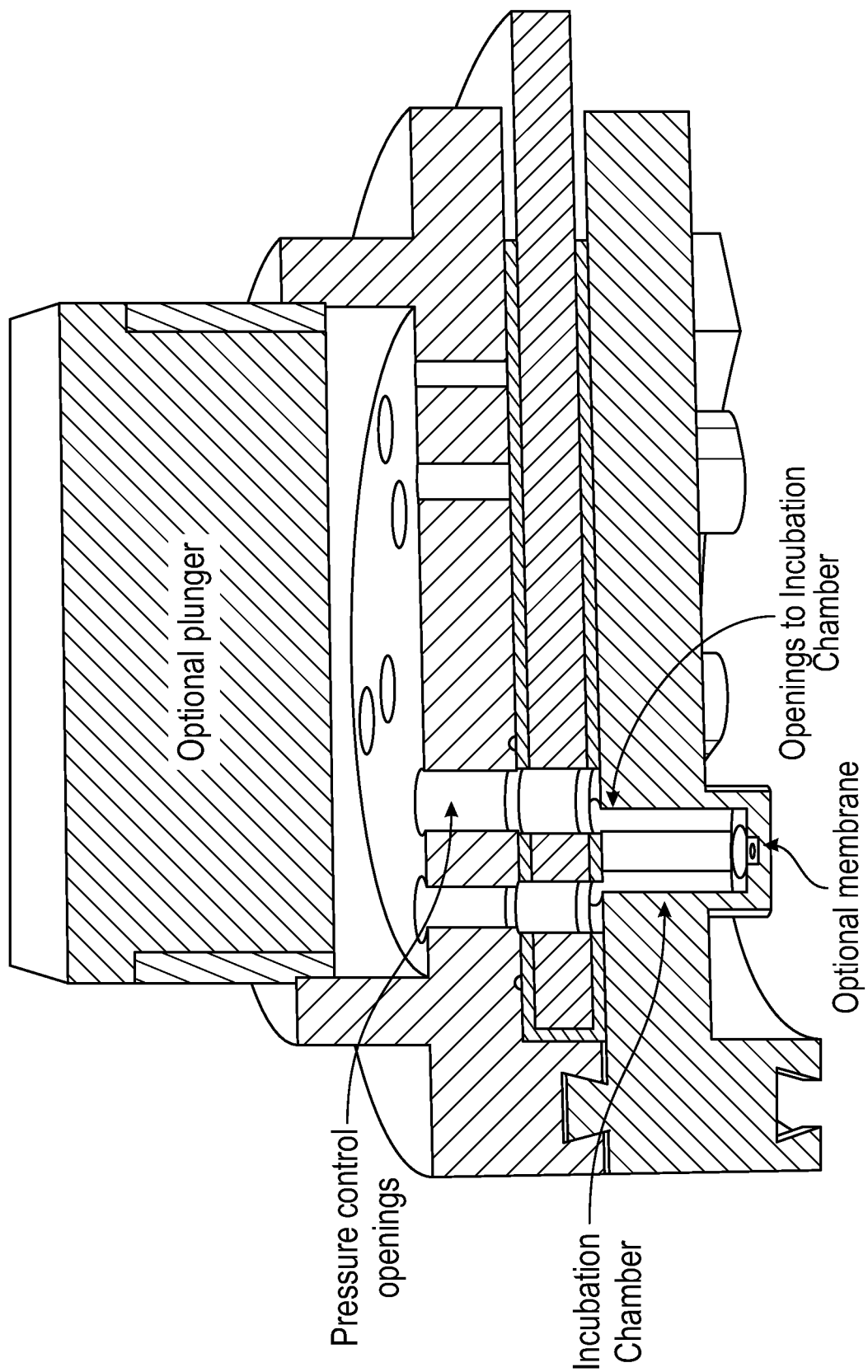

```
                        SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgccgtaact tcgggagaag gca                                              23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcaaggacca gtgttcagtg tc                                               22
```

MICROFLUIDIC MEASUREMENTS OF THE RESPONSE OF AN ORGANISM TO A DRUG

CROSS-REFERENCE TO RELATED APPLICATIONS

This application is the National Stage of International Application No. PCT/US2015/059344, filed Nov. 5, 2015, which claims the benefit of and priority to U.S. Provisional Application No. 62/075,648, filed Nov. 5, 2014, the contents of which are incorporated herein by reference in their entirety.

STATEMENT AS TO FEDERALLY SPONSORED RESEARCH

This invention was made with government support under grant numbers EB012946, GM074961 and OD003584 awarded by the National Institutes of Health and contract number HR0011-11-2-0006 awarded by the Defense Advanced Research Projects Agency. The government has certain rights in the invention.

SEQUENCE LISTING

The instant application contains a Sequence Listing which has been submitted via EFS-Web and is hereby incorporated by reference in its entirety. Said ASCII copy, created on May 4, 2017 is named 31072US_CRF_sequencelisting.txt, and is 827 bytes in size.

TECHNICAL FIELD

The present application relates to the field of microfluidics and to the fields of detection and amplification of biological entities.

BACKGROUND OF THE INVENTION

Antibiotic resistance constitutes a major imminent threat to public health worldwide. Statistics from the CDC (U. S. Department of Health and Human Services, 2013, 114) and WHO (Organization, 2014, 257) are alarming and emphasize that the current paradigm of liberal and non-selective antibiotic use cannot continue. Emergence of resistance in Gram-negative organisms, for which there are limited treatment options, is of particular concern. Over-use of broad-spectrum antibiotics in clinics is a major contributor to the evolution and spread of drug-resistant pathogens; however, combating resistance requires diagnostic development in all settings.

To improve care, clinical laboratories require rapid tests to identify the pathogen and determine its antimicrobial susceptibility. Laboratories currently conduct identification and antimicrobial susceptibility tests (AST) via culture-based methods, which take 24-48 hours. Because the physician does not know in a proximate timeframe what organism is present, the bacterial burden, or the susceptibility of the organism to various therapeutic approaches, clinicians often choose to treat with broad spectrum (e.g. 2nd and 3rd generation) antibiotics and can even treat sub-clinical infection or false positives. Overprescribing antibiotics is most acute among complex, recurrent, and specialty cases. These include febrile children, obstructed patients, such as men with BPH, nephrolithiasis, especially those with repeated instrumentation, women with infection during pregnancy, hospitalized patients, and immune-compromised patients. In these situations, clinicians tend to treat more aggressively. Accelerating turnaround will allow clinicians to improve patient care by administering the right antimicrobial regimen without delays. Thus, to improve the problem of emerging antimicrobial resistance and to improve care, physicians in primary care settings require ultra-rapid tests to identify the pathogen and determine its antimicrobial susceptibility. What is needed, therefore, are devices and methods for rapidly and accurately diagnosing infection and antimicrobial resistance or susceptibility.

SUMMARY OF THE INVENTION

In one aspect, the invention provides devices and methods can rapidly identify a cell, including a cancer cell, or microorganism, including a pathogen, quantify their load, and diagnose their susceptibility or resistance to drugs, such as antibiotics. In some embodiments the devices can enable phenotypic detection and metabolic profiling of drug susceptibility or drug resistance using individual microorganisms or cells which can originate from various sample types, including clinical or environmental samples. These sample types can include, but are not limited to, blood, cerebral spinal fluid (CSF), saliva and urine and can also include environmental samples, such as from water or a hospital surface. In some embodiments, the devices enable incubation of cells with drugs, such as antibiotics, and then rapidly extract and quantify nucleic acids or other molecules in a contamination-free platform. The devices can use digital single-molecule measurements in microfluidics devices, which provide ultra-sensitive measurements that improve detection limits while providing quantitative data, important for differentiating pathogens from contaminants and enabling earlier differentiation between drug-resistant and susceptible organisms or cells. In some embodiments, these devices can differentiate the state of individual microorganisms or cells from a clinical sample, and understand the timing of their individual responses to drugs, such as for example antibiotics, providing ultra-fast drug-susceptibility measurements.

In some embodiments, the data associated with the sample comprises measurements from greater than one spatially-isolated compartment each of the compartments comprising a portion of the sample.

In some embodiments, the sample undergoes a nucleic acid amplification. In some embodiments, the nucleic acid amplification reaction is a loop mediated amplification (LAMP) reaction. In some embodiments, the nucleic acid amplification reaction is a PCR reaction. In some embodiments, the method is performed at about or at a temperature range of 55-65° C. In some embodiments, at least a portion of the sample is partitioned into an array comprising at least 2 or more. In some embodiments, the array is a SlipChip. In some embodiments, the nucleic acid that is amplified is RNA.

Also provided herein are methods for detecting and quantifying target molecules from a sample, comprising: providing a first sample comprising a target molecule from a first portion of a population of bacteria and a second sample comprising a target molecule from a second portion of said population of bacteria, wherein the first portion has been treated with an antibiotic, and wherein the second portion has not been treated with the antibiotic; distributing said first sample among a plurality of first analysis regions; distributing said second sample among a plurality of second analysis regions; contacting each of the first and second analysis regions with a reagent for performing a reaction to detect the presence or absence of a threshold number of target molecules in each of the first and second analysis regions; and detecting the presence or absence of the threshold number of target molecules in each of the first and second analysis regions, wherein the distribution of each sample among the analysis regions is effected such that the threshold number of target molecules is detected in some of the first and second analysis regions and is not detected in some of the first and second analysis regions after said reaction.

In some embodiments, the threshold number is greater than zero, one, two, three, four, or five. In some embodiments, the distribution of each sample among the analysis regions is effected such that at least some of the analysis regions do not have the target molecule, and at least some of the analysis regions have only one target molecule. In some embodiments, the distribution of each sample among the analysis regions is effected such that at least one of the analysis regions contains only one target molecule. In some embodiments, the first sample comprises said reagent, and wherein contacting the plurality of first analysis regions with the reagent comprises said step of distributing said first sample among said plurality of first analysis regions. In some embodiments, the second sample comprises said reagent, and wherein contacting the plurality of second analysis regions with the reagent comprises said step of distributing said second sample among said plurality of second analysis regions.

In some embodiments, reaction comprises nucleic acid amplification. In some embodiments, the nucleic acid amplification is essentially isothermal. In some embodiments, the nucleic acid amplification is a polymerase chain reaction. In some embodiments, the nucleic acid amplification is a nucleic acid sequence based amplification (NASBA), self-sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR, or ligation mediated PCR.

In some embodiments, said analysis regions comprise wells. In some embodiments, the target molecule is a nucleic acid. In some embodiments, the reagent is a nucleic acid amplification reagent. In some embodiments, the method of detecting and quantifying target molecules from a sample further comprises exposing each of the analysis regions to conditions effective for amplification of the nucleic acid.

In some embodiments, the target molecule comprises a segment of a bacterial chromosome or plasmid. In some embodiments, the target molecule is less than 50 kDa, less than 100 kDa, less than 200 kDa, or less than 400 kDa from the origin of replication. In some embodiments, the target molecule comprises a sequence of a gene on said bacterial chromosome or plasmid. In some embodiments, the target molecule comprises mRNA. In some embodiments, the target molecule is amplified by an amplification reaction, said amplification reaction comprising primers complementary to a sequence of the target molecule. In some embodiments, the mRNA encodes recA or lexA.

In some embodiments, the reagent is disposed in a plurality of reagent regions. In some embodiments, contacting is effected by placing the plurality of reagent regions in fluid communication with the first or second plurality of analysis regions. In some embodiments, contacting comprises effecting relative motion between a substrate comprising the reagent regions with a substrate comprising the first and second plurality of analysis regions. In some embodiments, the method of detecting and quantifying target molecules from a sample further comprises analyzing the detection of the presence or absence of the threshold number of target molecules in each plurality of analysis regions to determine a resistance or susceptibility to an antibiotic in the population of bacteria.

In some embodiments, the target molecule has been removed from the bacteria in the first sample, and wherein the time between initial exposure of the bacteria to antibiotic and the removal of the target molecules is less than the mean doubling time of the bacteria during a growth phase. In some embodiments, the detection of the presence or absence of the threshold number of target molecules in each of the first and second analysis regions is performed less than 3 hours, 2 hours, or one hour after the end of exposure of the first sample to the antibiotic. In some embodiments, the detection of the presence or absence of the threshold number of target molecules in each of the first and second analysis regions is performed less than 45 minutes, 30 minutes, 15 minutes, or 10 minutes after the end of exposure of the first sample to the antibiotic. In some embodiments, the detection of the presence or absence of the threshold number of target molecules in each of the first and second analysis regions is performed less than 3 hours, less than 2 hours, or less than 1 hour after the end of exposure of the first sample to the antibiotic. In some embodiments, the detection of the presence or absence of the threshold number of target molecules in each of the first and second analysis regions is performed less than 45 minutes, less than 30 minutes, less than 15 minutes, or less than 10 minutes after the end of exposure of the first sample to the antibiotic.

In some embodiments, the bacteria from said first sample have been treated with antibiotic for a period of no more than 2 hours, no more than 1 hour, no more than 45 minutes, no more than 30 minutes, no more than 15 minutes, or no more than 10 minutes. In some embodiments, the time from the first exposure of the bacteria from the first sample to an antibiotic to the detection step is less than 3 hours, less than 2 hours, less than 1 hour after, less than 45 minutes, or less than 30 minutes.

In some embodiments, the first plurality of analysis regions comprises at least 10, 20, 30, 40, or 50 analysis regions. In some embodiments, the second plurality of analysis regions comprises at least 10, 20, 30, 40, or 50 analysis regions. In some embodiments, the distribution of the first and second sample into the first and second plurality of analysis regions is performed in parallel. In some embodiments, the first sample or second sample comprises less than 10,000, 5,000, 1,000, 500, 200, 100, 50, 20, or 10 target molecules.

Also provided herein is a method of determining a resistance or susceptibility to an antibiotic in a population of bacteria, comprising: providing a first sample comprising a target molecule from a first portion of a population of bacteria and a second sample comprising a target molecule from a second portion of said population of bacteria, wherein the first portion has been treated with an antibiotic, and wherein the second portion has not been treated with the antibiotic; distributing said first sample among a plurality of first analysis regions; distributing said second sample among a plurality of second analysis regions; contacting each of the first and second analysis regions with a reagent for performing a reaction to detect the presence or absence of a threshold number of target molecules in each of the first and second analysis regions; detecting the presence or absence of the threshold number of target molecules in each of the first and second analysis regions, wherein the distribution of each sample among the analysis regions is effected such that the threshold number of target molecules is detected in some of the first and second analysis regions and is not detected in some of the first and second analysis regions after said reaction; and analyzing the results of the detection to determine a resistance or susceptibility to said antibiotic in the population of bacteria.

Also provided herein is a method of determining a resistance or susceptibility to an antibiotic in a population of bacteria, comprising: distributing a population of bacteria into a plurality of clonal isolation regions, the distribution being effected such that at least some of the clonal isolation regions are statistically estimated to each contain a single isolated bacterium; expanding each of the single isolated bacteria to generate a plurality of clonal populations; distributing each of said plurality of clonal populations into at least one treatment region from a plurality of treatment regions and into at least one control region from a plurality of control regions; contacting the first plurality of treatment regions with an antibiotic, the plurality of control regions not contacted with the antibiotic; for each of the first plurality of treatment regions and each of the plurality of control regions, distributing one or more target molecules from each clonal population into a distinct plurality of analysis regions; contacting each of the analysis regions with a reagent for performing a reaction to detect the presence or absence of a threshold number of target molecules in each of the first and second analysis regions; and detecting the presence or absence of the threshold number of target molecules in each of the first and second analysis regions, wherein the distribution of each sample among the analysis regions is effected such that the threshold number of target molecules is detected in some of the distinct plurality of analysis regions and is not detected in some of the distinct plurality of analysis regions after said reaction.

In some embodiments, the method of determining a resistance or susceptibility to an antibiotic in a population of bacteria further comprises analyzing the results of the detection to determine a resistance or susceptibility to said antibiotic in at least some of said plurality of clonal populations.

Also provided herein are methods, comprising: providing a first sample comprising a target analyte from a first portion of a population of cells and a second sample comprising a target analyte from a second portion of said population of cells, wherein the first portion has been treated with a drug, and wherein the second portion has not been treated with the drug; distributing said first sample among a plurality of first analysis regions; distributing said second sample among a plurality of second analysis regions; contacting each of the first and second analysis regions with a reagent for performing a reaction to detect the presence or absence of a threshold number of target analytes in each of the first and second analysis regions; and detecting the presence or absence of the threshold number of target analytes in each of the first and second analysis regions, wherein the distribution of each sample among the analysis regions is effected such that the threshold number of target analytes is detected in some of the first and second analysis regions and is not detected in some of the first and second analysis regions after said reaction.

Also provided herein are kits comprising: a container comprising a plurality of analysis regions, a plurality of reagent regions comprising a component of a nucleic acid amplification, wherein the container comprises a first layer and a second layer configured to move relative to the other between a first position, where the plurality of analysis regions and the plurality of reagent regions are isolated from each other, and a second position, wherein at least some of the plurality of analysis regions is in fluid communication with at least some of the plurality of reagent regions; and instructions for use for determining a resistance or susceptibility to an antibiotic in a population of bacteria.

In some embodiments, the component of a nucleic acid amplification comprises primers for amplifying recA or lexA mRNA. In some embodiments, the component of a nucleic acid amplification comprises primers for amplifying a nucleic acid target on a bacterial chromosome or plasmid less than 50 kDa, less than 100 kDa, less than 200 kDa, or less than 400 kDa from the origin of replication. In some embodiments, the container comprises at least 10, 20, 30, 40, or 50 analysis regions. In some embodiments, the container comprises at least 10, 20, 30, 40, or 50 reagent regions.

In some embodiments, the antibiotic is selected from the group consisting of: aminoglycosides, cephalosporins, tetracyclines, sulfonamides, macrolides, vancomycin, and β-lactams. In certain of these embodiments, the instructions indicate that a decrease in nucleic acid target detection in a portion of the population of bacteria treated with said antibiotic as compared to a portion of the population of bacteria not treated with said antibiotic indicates that the population of bacteria is susceptible to said antibiotic.

In some embodiments, the antibiotic is selected from the group consisting of: HPUra, hydroxyurea, trimethoprim, ciprofloxacin, and MMC. In certain of these embodiments, the instructions indicate that an increase in nucleic acid target detection in a portion of the population of bacteria treated with said antibiotic as compared to a portion of the population of bacteria not treated with said antibiotic indicates that the population of bacteria is susceptible to said antibiotic.

Also provided herein is a device for processing a sample, comprising an incubation module, a sample preparation module, and a digital quantification module, wherein said device is configurable to place each module in fluid communication with the other modules; wherein said incubation module comprises an incubation chamber configured to incubate an organism with a drug, wherein said sample preparation module is configured to extract a nucleic acid from said organism; and wherein said digital quantification module comprises a plurality of reaction areas configured to perform digital detection of the presence or absence of said nucleic acid in said reaction area.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Described herein are a number of devices and methods that can be used individually or in various combinations for applications including but not limited to those listed herein. Furthermore, they can be used in various combinations with previously disclosed devices and methods for previously described applications.

The present application incorporates the following applications by reference in their entireties for any and all purposes: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011; U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011; international application PCT/US2010/028361, "Slip Chip Device and Methods," filed on Mar. 23, 2010; U.S. Application 61/262,375, "Slip Chip Device and Methods," filed on Nov. 18, 2009; U.S. Application 61/162,922, "Slip Chip Device and Methods," filed on Mar. 24, 2009; U.S. Application 61/340,872, "Slip Chip Device and Methods," filed on Mar. 22, 2010; U.S. application Ser. No. 13/440,371, "Analysis Devices, Kits, And Related Methods For Digital Quantification Of Nucleic Acids And Other Analytes," filed on Apr. 5, 2012; U.S. application Ser. No. 13/467,482, "Multivolume Devices, Kits, Related Methods for Quantification and Detection of Nucleic Acids and Other Analytes," filed on May 9, 2012; U.S. application Ser. No. 13/868,028, "Fluidic Devices and Systems for Sample Preparation or Autonomous Analysis," filed on Apr. 22, 2013; U.S. application Ser. No. 13/868,009, "Fluidic Devices for Biospecimen Preservation," filed on Apr. 22, 2013; international application PCT/US2013/037658, "Fluidic Devices for Biospecimen Preservation," filed on Apr. 22, 2013; international application PCT/US2013/037660, "Fluidic Devices and Systems for Sample Preparation or Autonomous Analysis," filed on Apr. 22, 2013; U.S. application Ser. No. 13/869,856, "Slip-Induced Compartmentalization," filed Apr. 24, 2013; international application PCT/US2013/063594, "Methods and Systems for Microfluidics Imaging and Analysis," filed on Oct. 4, 2013; international application PCT/US2014/034728, "Parallelized Sample Handling," filed on Apr. 18, 2014; international application PCT/US2014/047092, "Digital Assay for Quantifying and Concentrating Analytes," filed on Jul. 17, 2014; U.S. Application 62/038,036, "The Pumping Lid: Devices and Methods for Programmable Generation of Positive and Negative Pressures," filed on Aug. 15, 2014; U.S. Application 62/050,647, "Digital Microfluidics Methods for Optimizing Isothermal Amplification Reactions," filed on Sep. 15, 2014; international application PCT/US2014/056401, "System and Method for Movement and Timing Control," filed on Sep. 18, 2014; and International Application No. PCT/US2014/060977 "Enhanced Nucleic Acid Identification and Detection" filed on Oct. 16, 2014.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 6A, 6B, and 6C show 3 different views of an integrated device comprising an incubation module, according to an embodiment of the invention.

DETAILED DESCRIPTION OF THE INVENTION

Figure 1:
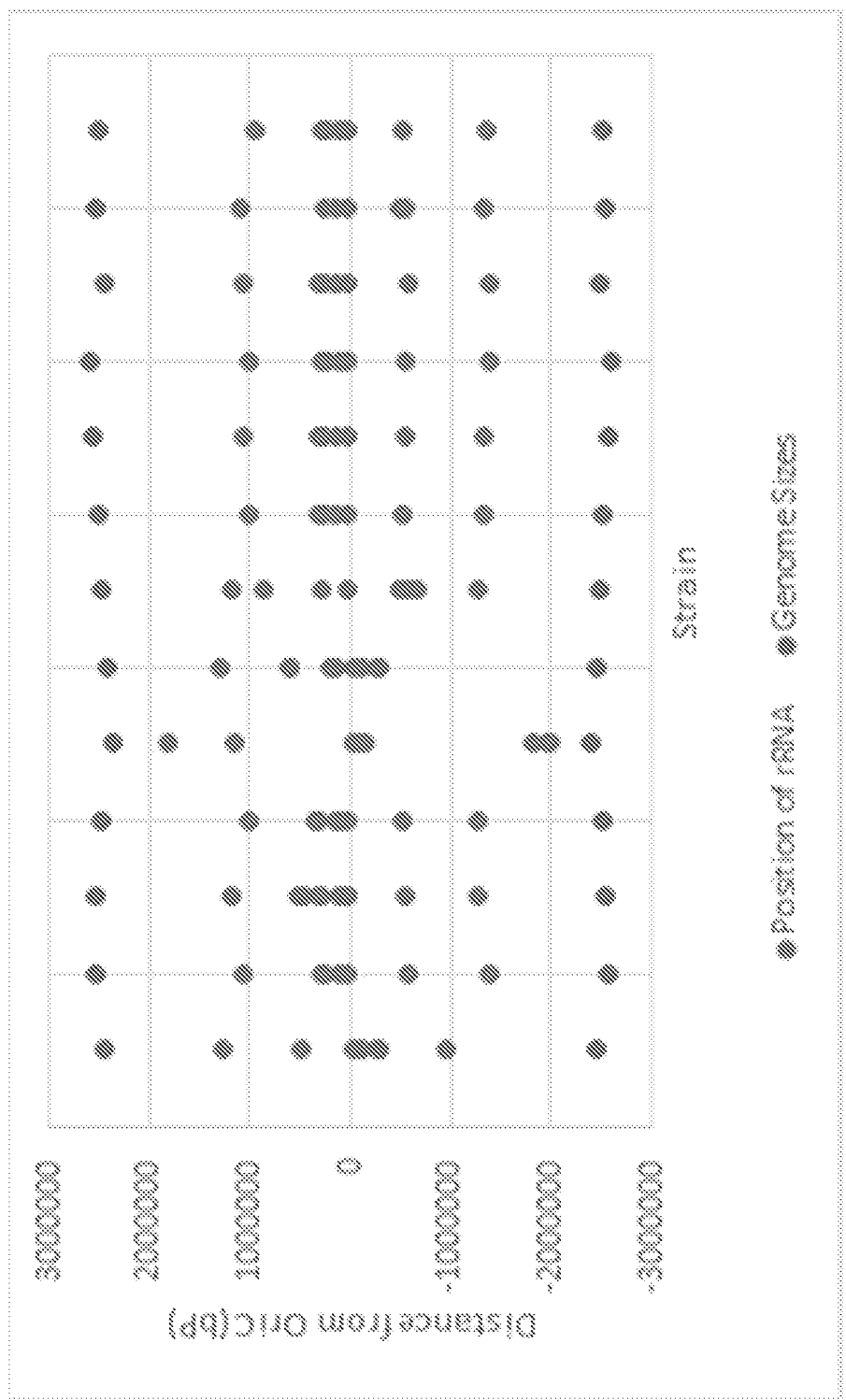
FIG. 1 shows the mapped position of rDNA genes relative to the origin of replication in a Urinary Tract Infection (UTI) *Escherichia coli* isolates.

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

As used herein, ranges and amounts can be expressed as "about" a particular value or range. About also includes the exact amount. Hence "about 10 degrees" means "about 10 degrees" and also "10 degrees." Generally, the term "about" can include an amount that would be expected to be within experimental error.

Assays

The devices and methods described herein can be applied for assays for detection of drug susceptibility or resistance in an organism. The detection can be detection of a signal generated by an assay, for example, an assay to detect a nucleic acid or quantification of a nucleic acid associated with a resistance or susceptibility to a drug in an organism.

An assay can comprise conducting a reaction (e.g., amplification) on a nucleic acid from an organism exposed to a drug and comparing the results of the reaction (e.g., reaction outcome, positive or negative signal generation) to a reaction conducted on a nucleic acid from an organism that has not been exposed to the drug. This can reveal a susceptibility or a resistance of the organism to the drug.

In certain embodiments, the method comprises exposing a portion of a sample containing a microorganism to a drug. In some embodiments, the method further comprises extracting nucleic acid from the micro-organism. In some embodiments, the method comprises performing a sequence-specific quantification of a nucleic acid from the microorganism. The quantification information is then used for determining or quantifying a resistance or susceptibility of a microorganism to a drug.

Assays can be conducted in a digital format, that is, assays can be conducted on a sample divided into partitions (i.e., analysis regions) such that some of the partitions provide no signal, while other partitions provide a signal. In some embodiments, the partitions contain one or zero target analytes (e.g., a target cell, a portion of a cell, or a target molecule, such as nucleic acid molecules or proteins). In some cases, some partitions can contain more than one target analyte. In some embodiments, the reaction efficiency is such that a threshold number of target analytes is required to achieve a positive signal. In these cases, the format is digital if some of the partitions contain a number of target analytes above the threshold, and some of the partitions contain a number of target analytes below the threshold. In some embodiments, the threshold can vary between partitions, such that some partitions with fewer target analytes generate a signal, while some partitions with more target analytes do not generate signal. In these cases, digital detection can still be performed based on a probabilistic threshold applied over a plurality of wells, as long as some partitions do not produce a signal, and some do.

In some cases, the majority of partitions contain one or zero target analytes. This digital or single molecule format can be used in conjunction with assays described herein, including identification, detection, genotyping, SNP detection, rare allele detection, and quantification of nucleic acids.

An assay can be conducted in less than or equal to about 600 minutes, 540 minutes, 480 minutes, 420 minutes, 360 minutes, 300 minutes, 240 minutes, 180 minutes, 120 minutes, 110 minutes, 100 minutes, 90 minutes, 80 minutes, 70 minutes, 60 minutes, 50 minutes, 40 minutes, 30 minutes, 20 minutes, 15 minutes, 10 minutes, 9 minutes, 8 minutes, 7 minutes, 6 minutes, 5 minutes, 4 minutes, 3 minutes, 2 minutes, or 1 minute. An assay can have an accuracy of at least about 50%, 60%, 70%, 80%, 90%, 95%, 96%, 97%, 98%, 99%, 99.9%, or 99.99%. The rates of false positives can be below 10%, below 1%, below 0.1%, below 0.01%, below 0.001%, or below 0.0001%. The rates of false negatives can be below 10%, below 1%, below 0.1%, below 0.01%, below 0.001%, or below 0.0001%.

Assays can be used for detecting copy number variations (CNVs). CNVs are a form of structural variation, alterations of the DNA of a genome that changes the number of copies of one or more sections of the DNA. CNVs can correspond to relatively large regions of the genome that have been deleted or duplicated on certain chromosomes. Like other types of genetic variation, some CNVs have been associated with susceptibility or resistance to disease. Gene copy number can be elevated in cancer cells. The methodology described herein also allows identifying genetic changes at chromosome level.

Antibiotic susceptibility testing method through measuring DNA replication (e.g. detecting CNV) is applicable to evaluation of response to antibiotics, and other agents impairing cell growth and genomic DNA replication in all the unicellular and multicellular organisms, including eukaryotes. The measurement of "relative chromosomal DNA replication rate" is a useful measurable parameter to distinguish between susceptible cells growing in the presence versus absence of a drug (e.g., an antibiotic) and resistant cells growing in the presence versus absence of a drug. In some embodiments, differences in these markers can be observed using the devices and methods disclosed herein within a time period that is shorter than the average time of division of a cell, enabling the detection of cellular replication in that cell earlier than methods of detection that are dependent on cell-division. Therefore, methods and devices described herein enable one to rapidly distinguish between cells that are drug resistant and drug susceptible. The methods and devices provided herein can also be applied to any drug-screening, including screening of human cells (such as e.g. in the monitoring of a tumor biopsy in response to treatment).

In one embodiment, copy number of rDNA within cells is measured after cells are incubated for short periods of time, with and without the presence of antibiotics, and the difference in the magnitude of this change is used to determine drug resistance and susceptibility of the cells. In some embodiments, the change in rDNA copy is determined using a nucleic acid amplification technique (such as for example qPCR or digital PCR or digital isothermal amplification), and the results used to determine resistance or susceptibility to the drug. In some embodiments, the method for determining drug susceptibility uses digital quantification. In some embodiments average DNA fragments copies originated from individual cells, are digitally quantified to measure proximal to origin/distant to origin selected gene rates.

In some embodiments, drug susceptibility testing is based on RNA, such as by comparing transcription levels. In some embodiments, drug susceptibility testing is based on RNA, such as by comparing transcription levels using digital quantification. In some embodiments, quantification strategies (such as e.g. NASBA, qRT-PCR, sequencing, nanostring, among others) can be appropriate. In some embodiments RNA from cells obtained from samples is quantified in a digital format. In some embodiments gene target expression levels in each individual cell are quantified through single cell measurements on a device, such as the devices described herein.

An assay can be used for quantitative detection of nucleic acids, such as recA mRNA. For example, a method can be used comprising the steps of taking a sample from the patient, accessing RNA in the sample or extracting RNA from the sample, using at least one RT-LAMP primer to reverse transcribe and amplify the mRNA in a qualitative and/or in a quantitative format, and testing for amplification to confirm presence of nucleic acids including but not limited to recA mRNA.

In some embodiments, relative RNA and/or DNA amplification is used. In some embodiments, relative RNA and/or DNA quantification is used. In some embodiments digital detection is used for RNA and/or DNA quantification. In some embodiments, multiple reliable RNA and/or DNA targets will be used simultaneously in multiplex format In some embodiments, RNA targets and/or their genes involved in the same physiological process or antibiotic response mechanism can be used.

In some embodiments, this invention could be applied to drug resistance testing of tumor cells. In some embodiments, this invention be applied to drug resistance testing of cancerous cells. The devices describe herein are applicable for use with a variety of sample types, including clinical sample types, (such as, for example, in-patient vs out-patient, pre-treated vs treatment-naïve), infection levels (such as, for example, negative vs positive vs contaminated), and sample storage/handling (such as, for example, fresh vs borate-preserved vs refrigerated).

In some embodiments, a slow growing microorganism's drug resistance is possible to assess through a combination of staining and genetic markers using the devices and methods described herein. In some embodiments, a combination of genetic markers of cell growth and genetic markers of antibiotic susceptibility can be used to determine the genetic antibiotic resistance of slow-growing cells.

The assays, reactions, and techniques described herein can be performed on any suitable platform, including but not limited to tubes, capillary tubes, droplets, microfluidic devices (e.g., SlipChip devices), wells, well plates, microplates, microfluidic wells, microfluidic droplets, emulsions, solid supports (e.g., beads or microarrays), microchips, or gels (e.g., 2D gels, 3D gels) and reactions inside gels including "polonies" as in polony PCR on surfaces and in gels.

In one embodiment, an assay to determine the resistance or susceptibility of a cell is performed as follows: Cells are pre-cultured (e.g. at 37° C.) to a desired density (e.g. $10^1$ cells/mL, $10^2$ cells/mL, $10^3$ cells/mL, $10^4$ cells/mL, $10^5$ cells/mL, $10^6$ cells/mL, $10^7$ cells/mL, $10^8$ cells/mL, or $10^9$ cells/mL) in various matrices (e.g. a Bacto Brain-Heart Infusion broth (BHI), a mix of BHI and pooled human urine, and/or whole human urine) before being diluted and incubated with or without a drug. In some embodiments, incubation is performed at a desired temperature (e.g. 37° C.) and then treated with a desired concentration of antibiotics. Cells can be incubated with and without antibiotics for a period of time (e.g. <10 minutes, 10 minutes, 15 minutes, 20 minutes, 30 minutes, 45 minutes, 60 minutes, or >60 minutes) before an aliquot of the culture or the original test sample is used for nucleic acid extraction. Nucleic acids can be extracted using standard methods (such as e.g. a one-step DNA extraction buffer or a one-step RNA extraction buffer (e.g. available from Epicentre), among others). In some embodiments, following extraction, nucleic acids are quantified using nucleic acid amplification techniques, such as e.g. quantitative PCR or digital PCR. To quantify 23S genes in *Enterobacter*, the following 23S primers specific for *Enterobacter* can be used: TGCCGTAACTTCGG-GAGAAGGCA (SEQ ID NO: 1); TCAAGGACCAGTGTTCAGTGTC (SEQ ID NO: 2; 428 bp product. (See, Matsuda K, Tsuji H, Asahara T, Kado Y, Nomoto K. Sensitive Quantitative Detection of Commensal Bacteria by rRNA-Targeted Reverse Transcription-PCR. *Applied and Environmental Microbiology.* 2007; 73(1):32-39. doi:10.1128/AEM.01224-06). The *E. coli* genome contains seven distinct operons with minor sequence differences, such as (such as (rrnA, rrnB, rrnC, rrnD. rrnE, rrnG (aka rrnF) and rrnH. The term "rDNA," as used herein, refers to rRNA operons sequences. This term includes both coding sequences and non-coding sequences/spacers. In some embodiments, this invention takes advantage of rDNA to provide both most conservative sequences and variable enough sequences to design primers targeting specific species. A typical operon coding for rRNA (such as GenBank: J01695.2) codes for 5S, 16S and 23S rRNA as well as tRNA, and has spacers in between these sequences. When using rDNA genes as replication markers, primers either for the coding parts of the rRNA operons, or for the spacers between them, or both, can be selected.

Samples

Disclosed herein are methods, devices and systems related to analysis of samples. In some embodiments, methods of the invention comprises obtaining a sample from an organism. A sample can be obtained from a subject (e.g., a patient or a pet) and can include blood, feces, urine, saliva or other bodily fluid. The sample can be obtained by the patient or by a medical professional. Examples of medical professionals include, but are not limited to, physicians, emergency medical technicians, nurses, first responders, psychologists, medical physics personnel, nurse practitioners, surgeons, dentists, and any other medical professional. The sample can be obtained from any bodily fluid, for example, amniotic fluid, aqueous humor, bile, lymph, breast milk, interstitial fluid, blood, blood plasma, cerumen (ear-wax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In an example, the sample is obtained by a blood draw, where the medical professional draws blood from a subject, such as by a syringe.

Samples can be collected in a sample collection container. In some embodiments the sample collection container is coded with information that can be detected. For example a detector can recognize a barcode. The barcode can have information about where a sample was collected or from which individual a sample was collected. A detector can take this information and use it to process or transmit data generated regarding a sample. For example a camera-phone can take a photo of a sample collection container. The camera-phone can recognize a barcode on the container which identifies a patient. The camera-phone can then link date generated regarding the sample to the patient from which the sample was obtained. The linked data can then be transmitted to the patient or to the patient's physician. In some embodiments a single image is generated of the sample collection container and a sample analysis unit.

Food samples can also be analyzed. Samples can be any composition potentially comprising a target organism. Sources of samples include, but are not limited to, geothermal and hydrothermal fields, acidic soils, sulfotara and boiling mud pots, pools, hot-springs and geysers where the enzymes are neutral to alkaline, marine actinomycetes, metazoan, endo and ectosymbionts, tropical soil, temperate soil, arid soil, compost piles, manure piles, marine sediments, freshwater sediments, water concentrates, hypersaline and super-cooled sea ice, arctic tundra, Sargasso sea, open ocean pelagic, marine snow, microbial mats (such as whale falls, springs and hydrothermal vents), insect and nematode gut microbial communities, plant endophytes, epiphytic water samples, industrial sites and ex situ enrichments. Additionally, a sample can be isolated from eukaryotes, prokaryotes, myxobacteria (epothilone), air, water, sediment, soil or rock, a plant sample, a food sample, a gut sample, a salivary sample, a blood sample, a sweat sample, a urine sample, a spinal fluid sample, a tissue sample, a vaginal swab, a stool sample, an amniotic fluid sample, a fingerprint, aerosols, including aerosols produced by coughing, skin samples, tissues, including tissue from biopsies, and/or a buccal mouthwash sample. Other sample types include samples for clinical testing (such as, for example, in-patient vs out-patient, pre-treated vs treatment-naïve), infection level testing (such as, for example, negative vs positive vs contaminated), and storage/handling testing (such as, for example, fresh vs borate-preserved vs refrigerated).

Samples can comprise organisms. Samples can comprise microorganisms. The number of microorganisms in a sample can be less than 10, less than 100, less than 1,000, less than $10^4$, less than $10^5$, or less than $10^6$. In some embodiments, the sample is a processed sample (e.g., concentrated, filtered, etc.).

Samples can comprise target analytes from the organisms. Target analytes can comprise, for example, cells, portions of cells, polypeptides, or nucleic acids. Nucleic acids can be cell-free nucleic acids. Nucleic acids can be isolated from cells. Nucleic acids can be single or double stranded. Target analytes can comprise DNA or RNA. In some cases, the RNA is tRNA, mRNA, rRNA, trRNA, snRNA, snoRNA, smY, scaRNA, gRNA, RNase P, RNase MRP, aRNA, crRNA, incRNA, miRNA, piRNA, siRNA, tasi RNA, rasiRNA, 7SK, vRNA or any combination thereof. The DNA can be ssDNA, dsDNA, cDNA, or any combination thereof. In some cases, the DNA comprises a gene or a gene fragment. The gene or gene fragment can comprise a mutation. The mutation can comprise point mutations, insertions, deletions, amplifications, translocations, inversions, copy number variations, and/or other mutations. In some cases, the DNA comprises a non-coding region. The noncoding region can comprise functional sequences, regulatory elements, intrans, exons, pseudogenes, repeat sequences, transposons, viral elements, telomeres, genetic switches, transcription factor sites, operators, enhancers, silencers, promoters, insulators, and/or other regions. In some cases, the DNA comprises cDNA. In some cases, the DNA is from bacteria or viruses. In some cases, the DNA is collected from a cell. In some examples, the DNA is intracellular. In some cases, the DNA is extracellular.

Target analytes can comprise RNA. In some cases, the RNA comprises mRNA. In some cases, the RNA comprises noncoding RNA (ncRNA). The noncoding RNA can comprise transfer RNA (tRNA), ribosomal RNA (rRNA), transfer-messenger RNA (tmRNA), small nucleolar RNA (snoRNA), microRNA (miRNA), small interlering RNA (siRNA), small nuclear RNA (snRNA), piwi-interacting RNA (piRNA), long ncRNA (lncRNA), and/or other types of ncRNA. In some cases, the RNA is from bacteria or viruses. In some cases, the RNA is collected from a cell. In some examples, the RNA is intracellular. In some cases, the RNA is extracellular.

The terms "nucleic acid" and "nucleic acid molecule" as used interchangeably herein, refer to a molecule comprised of nucleotides, i.e., ribonucleotides, deoxyribonucleotides, or both. The term includes monomers and polymers of ribonucleotides and deoxyribonucleotides, with the ribonucleotide and/or deoxyribonucleotides being connected together, in the case of the polymers, via 5' to 3' linkages. However, linkages can include any of the linkages known in the nucleic acid synthesis art including, for example, nucleic acids comprising 5' to 2' linkages. The nucleotides used in the nucleic acid molecule can be naturally occurring or can be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like. Nucleic acids can be detected from a sample.

The term "oligonucleotide" as used herein refers to a nucleic acid molecule comprising multiple nucleotides. An oligonucleotide can comprise about 2 to about 300 nucleotides.

Target analytes can comprise genetic markers of cell growth and genetic markers of antibiotic susceptibility. Target analytes can include markers for drug resistance or susceptibility to tumor cells. Target analytes can include markers for oxidative stress that can be detected with, e.g., oxidation-sensitive dyes to assay cell viability in response to treatment with a drug. In some embodiments, target analytes comprise polypeptides or proteins. In some embodiments, target analytes include cell membrane or cell membrane associated molecules, wherein a change in the cell membrane or cell membrane associated molecule is linked to the response of an organism to a drug.

Organisms

The term "organism" refers to any organisms or microorganism, including bacteria, yeast, fungi, viruses, protists (protozoan, micro-algae), archaebacteria, plants and eukaryotes. Eukaryotes can be a single-celled eukaryotic cell. Bacteria include gram-positive and gram-negative bacteria. The term "organism" refers to living matter and viruses comprising nucleic acid that can be detected and identified by the methods of the invention. Organisms include, but are not limited to, bacteria, archaea, prokaryotes, eukaryotes, viruses, protozoa, *mycoplasma*, fungi, plants and nematodes. Different organisms can be different strains, different varieties, different species, different genera, different families, different orders, different classes, different phyla, and/or different kingdoms. Organisms can be isolated from environmental sources including soil extracts, marine sediments, freshwater sediments, hot springs, ice shelves, extraterrestrial samples, crevices of rocks, clouds, attached to particulates from aqueous environments, and can be involved in symbiotic relationships with multicellular organisms. Examples of such organisms include, but are not limited to *Streptomyces* species and uncharacterized/unknown species from natural sources. Organisms can include genetically engineered organisms or genetically modified organisms. Organisms can include transgenic plants. Organisms can include genetically modified crops. Any organism can be genetically modified. Examples of organisms which can be genetically modified include plantains, yams, sorghum, sweet potatoes, soybeans, cassava, potatoes, rice, wheat, or corn.

Organisms can include bacterial pathogens such as: *Aeromonas* hydrophile and other species (spp.); *Bacillus anthracis*; *Bacillus cereus*; *Botulinum neurotoxin* producing species of *Clostridium*; *Brucella abortus*; *Brucella melitensis*; *Brucella suis*; *Burkholderia mallei* (formally *Pseudomonas mallei*); *Burkholderia pseudomallei* (formerly *Pseudomonas pseudomallei*); *Campylobacter jejuni*; *Chlamydia psittaci*; *Clostridium botulinum*; *Clostridium botulinum*; *Clostridium perfringens*; *Coccidioides immitis*; *Coccidioides posadasii*; *Cowdria ruminantium* (Heartwater); *Coxiella burnetii*; Enterovirulent *Escherichia co//group* (EEC Group) such as *Escherichia coli*-enterotoxigenic (ETEC), *Escherichia coli*-enteropathogenic (EPEC), *Escherichia coli*-O157:H7 enterohemorrhagic (EHEC), and *Escherichia coli*-enteroinvasive (EIEC); *Ehrlichia* spp. such as *Ehrlichia chaffeensis*; *Francisella tularensis*; *Legionella pneumophilia*; *Liberobacter africanus*; *Liberobacter asiaticus*; *Listeria monocytogenes*; miscellaneous enterics such as *Klebsiella, Enterobacter, Proteus, Citrobacter, Aerobacter, Providencia*, and *Serratia*; *Mycobacterium bovis*; *Mycobacterium tuberculosis*; *Mycoplasma capricolum*; *Mycoplasma mycoides* ssp *mycoides*; *Peronosclerospora philippinensis*; *Phakopsora pachyrhizi*; *Plesiomonas shigelloides*; *Ralstonia solanacearum* race 3, biovar 2; *Rickettsia prowazekii*; *Rickettsia rickettsii*; *Salmonella* spp.; *Schlerophthora rayssiae* varzeae; *Shigella* spp.; *Staphylococcus aureus*; *Streptococcus*; *Synchytrium endobioticum*; *Vibrio cholerae* non-O1; *Vibrio cholerae* O1; *Vibrio parahaemolyticus* and other *Vibrios*; *Vibrio vulnificus*; *Xanthomonas oryzae*; *Xylella fastidiosa* (citrus variegated chlorosis strain); *Yersinia enterocolitica* and *Yersinia pseudotuberculosis*; and *Yersinia pestis*.

A non-limiting list of pathogens with known drug-resistance properties that can be detected and analyzed with the methods and devices disclosed herein include *Clostridium difficile*, carbapenem-resistant Enterobacteriaceae (CRE), drug-resistant *Neisseria gonorrhoeae*, multidrug-resistant *Acinetobacter*, drug-resistant *Campylobacter*, fluconazole-resistant *Candida* (a fungus), extended spectrum β-lactamase producing Enterobacteriaceae (ESBLs), vancomycin-resistant *Enterococcus* (VRE), multidrug-resistant *Pseudomonas aeruginosa*, drug-resistant Non-typhoidal *Salmonella*, drug-resistant *Salmonella Typhi*, drug-resistant *Shigella*, methicillin-resistant *Staphylococcus aureus* (MRSA), drug-resistant *Streptococcus pneumoniae*, drug-resistant *M. tuberculosis*, vancomycin-resistant *Staphylococcus aureus* (VRSA), erythromycin-resistant Group A *Streptococcus*, and clindamycin-resistant Group B *Streptococcus*.

Antimicrobial/Antibiotic Compounds

Organisms are incubated with a drug to determine a response to indicate their resistance or susceptibility to the drug. In some embodiments, the drug includes compounds for the treatment of a tumor. In some embodiments, the drug is an antibiotic compound or an antimicrobial compound. As used herein, the term antimicrobial is meant to include any substance of natural, semisynthetic or synthetic origin that is used to kill or inhibit the growth of a microorganism. In preferred embodiments, antimicrobials do not harm a host of the microorganism. As used herein, the term "antimicrobial" and the term "antibiotic" are interchangeable. Examples of antimicrobial or antibiotic compounds include, but are not limited to: Amikacin, Gentamicin, Kanamycin, Neomycin, Netilmicin, Tobramycin, Paromomycin, Streptomycin, Spectinomycin(Bs), Geldanamycin, Herbimycin, Rifaximin, Loracarbef, Ertapenem, Doripenem, Imipenem/Cilastatin, Meropenem, Cefadroxil, Cefazolin, Cefalotin/Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Dalbavancin, Oritavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin(Bs), Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic), Demeclocycline, Doxycycline, Minocycline, Oxytetracycline, Tetracycline, Clofazimine, Dapsone, Capreomycin, Cycloserine, Ethambutol(Bs), Ethionamide, Isoniazid, Pyrazinamide, Rifampicin (Rifampin in US), Rifabutin, Rifapentine, Streptomycin, Arsphenamine, Chloramphenicol(Bs), Fosfomycin, Fusidic acid, Metronidazole, Mupirocin, Platensimycin, Quinupristin/Dalfopristin, Thiamphenicol, Tigecycline(Bs), Tinidazole, and Trimethoprim(Bs).

Different antibiotics or antimicrobials may have different mechanisms of action and can affect replication propagation and replication re-initiation differently. Some bacteriostatic antibiotics (such as aminoglycosides, cephalosporins, tetracyclines, sulfonamides, and macrolides) inhibit protein synthesis, while bactericidal antibiotics can act on the cell wall (eg, vancomycin and β-lactams), or bacterial DNA (eg, fluoroquinolones). Some antibiotics, such as trimethoprim and sulfamethoxazole interfere with a metabolic pathways and affect DNA replication indirectly, and some (nitrofurantoin) affect multiple process in a cell, including DNA replication.

In some embodiments, treatment conditions will be adjusted to intensify an effect of antibiotics on DNA replication for every antibiotics group. In some embodiments, treatment conditions will be adjusted to speed up observation of an effect of antibiotics on DNA replication for every antibiotics group. In some embodiments, the method described in this disclosure tests for antibiotic susceptibility though relative gene quantification.

Targets/Target Analytes

In some embodiments the methods and devices provided herein target analytes (e.g., markers) indicative of growth of the microorganism in response to the presence or absence of an antimicrobial. In some embodiments, the change in expression and in copy numbers of the of genes close to OriC (such as for example competence genes) is measured. Our methods and devices enable rapid and sensitive quantification of total gene copy number proximal to ori for each bacterial species of interest.

Slowly growing cells can replicate their chromosomes more slowly, allowing the differentiation between cells effected by the antibiotic, and those killed by it. In addition, cells with impaired metabolism can generate more or less of specific RNA targets. Selection and quantification of these targets is described herein.

In some embodiments, the target analyte of interest is DNA. In some embodiments, DNA regions, such as those represented in multiple copies in published bacterial genomes, are selected as targets (such as rDNA). In some embodiments, more than one target (such as a DNA fragment or gene) is selected for simultaneous quantification; these targets can be located close to the origin of replication and/or can involve both directions of replication. In some embodiments, more than one target (such as a DNA fragment or gene) is selected for simultaneous quantification; one or more of these targets is located close to the origin of replication and one or more targets is far from the origin of replication. By measuring the ratio of these targets at certain times (in some cases, before replication is complete), replication can be detected rapidly in some embodiments without the need to measure the number of cells independently. This becomes valuable when very few cells are present in the sample, and or when very few cells are analyzed, and or when the accuracy with which the number of cells present in each part of a split sample is limited by Poisson statistics.

In some embodiments, detecting gene duplications due to antimicrobial treatment would allow detection of susceptible strains. In some embodiments, targets for a gene dosage approach can include Ori or genes positioned in proximity to OriC (such as e.g. within 50 kb, within 100 kb, within 150 kb, within 200 kb, and/or within 300 kb from OriC. In some embodiments the DNA/gene dosage in drug-susceptible cells will increase rather than decrease.

In some embodiments, DNA targets represented in single or in multiple copies in published bacterial genomes are selected as targets (such as e.g. rDNA, feoB gene, rpoB gene, competence genes, among others). In some embodiments, more than one target (such as a DNA fragment or gene) is selected for simultaneous quantification; these can be preferentially located close to the origin of replication in both directions In some embodiments, the target of interest is ribosomal DNA, rDNA, sequence. Ribosomal gene sequences, while being well conserved among bacteria, can be used as a target for identification and/or group identification, such as by selecting specific probes and/or primers In some rapidly growing bacterial species, it has been shown that ribosomal genes (and many genes associated with transcription and translation) tend to be preferentially located close to the origin of replication, suggesting the presence of evolutionary pressure, which is shown to be relevant to genome stability (Etienne Couturier, Eduardo P. C. Rocha. Replication-associated gene dosage effects shape the genomes of fast-growing bacteria but only for transcription and translation genes, 2006, Molecular microbiology, Volume 59, Issue 5, Pages 1506-1518, DOI: 10.1111/j.1365-2958.2006.05046.).). These genes can be used as targets for quantification of replication, thus enabling the detection of organisms exposed to growth conditions over short time periods, such as a time period that is shorter than the cell replication period. Using these genes as targets for digital quantification, even incomplete DNA replication (that happens before cells divide) can be detected.

For example, in a subset of 11 available genome-sequenced E. coli strains linked to UTI infections the position of rDNA genes relative to the origin of replication were mapped. FIG. 1 shows the relative distance of rDNA from oriC in UTI E. coli isolates. Red dots (top and bottom row) illustrate the genome size by showing the distance from OriC to termination of replication in a circular chromosome for both replichores. The rare examples of having ribosomal genes at different distribution belong to the genomes of bacteria which underwent artificial selection in laboratory conditions, such as the genome fifth from the left on the graph, which is not a UTI clinical isolate but E. coli from UTI patient gut selected for nitrofurantoin resistance (GenBank: CP007265.1). These show a trend of rDNA genes being clustered near the origin of replication.

Figure 2:
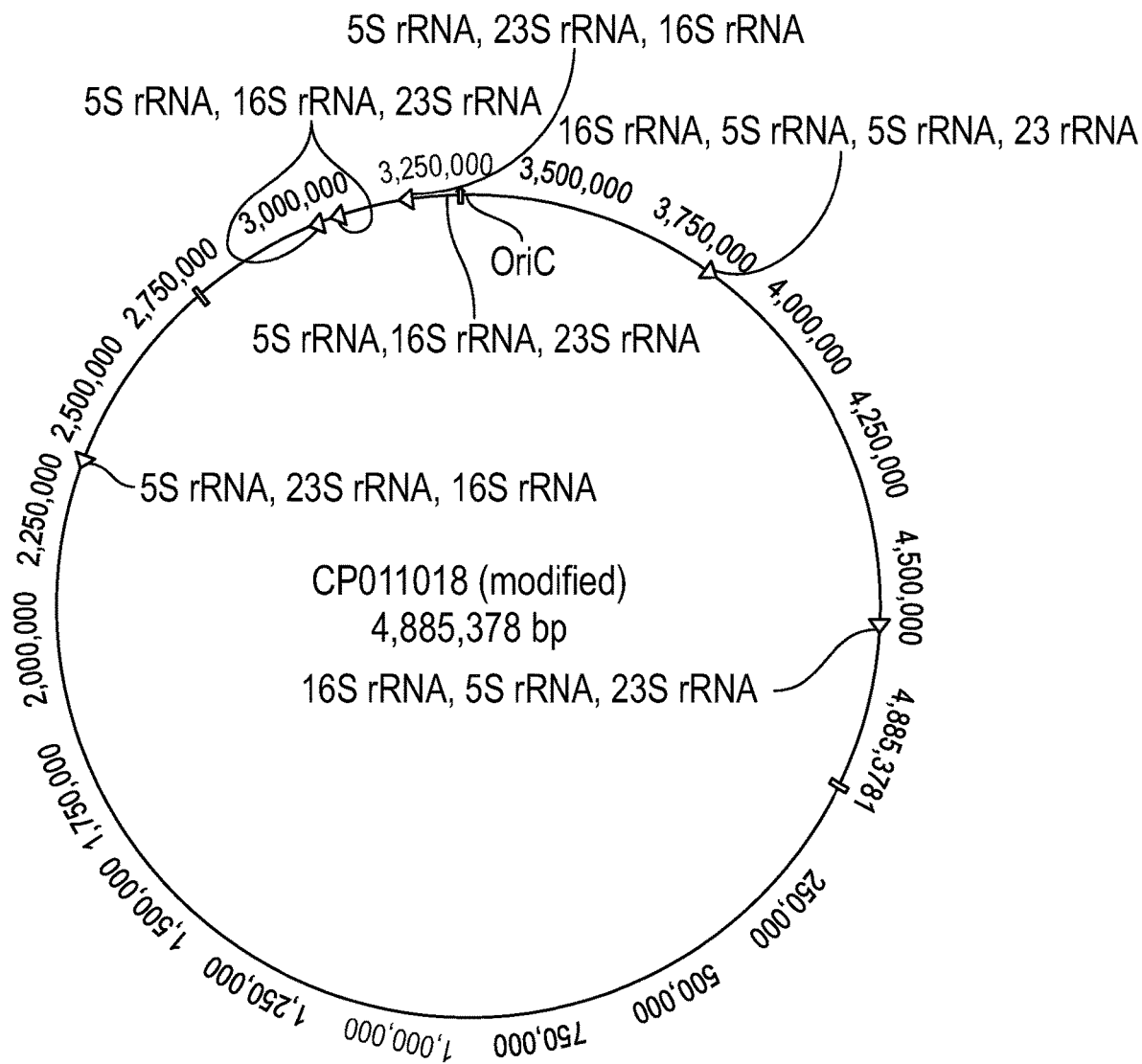
FIG. 2 shows circular representation of an example genome sequenced from an *E. coli* isolate from a UTI patient and the location of rRNA genes on the genome.

Another example of rDNA clustering near the origin of replication is shown in FIG. 2, showing a circular representation of an example genome sequenced from a UTI patient. Ribosomal RNA coding regions of the genome are marked with red. The origin of replication (OriC) is marked at the top of FIG. 2. rDNA is preferentially clustered near the origin of replication.

In some embodiments, the method disclosed herein takes advantage of the fact that in at least some cells of interest, there can be a specific time order of chromosomal splitting. For example, in E. coli, chromosome dynamics determines splitting of the certain parts of the chromosomes in a specific time order. In some embodiments the quantification of gene targets that are replicated earlier will allow higher resolution or faster determination of resistant versus susceptible bacteria. In addition, the origin and terminus of replication divide the genome into replichores, having different strands as leading strands. In some embodiments, target genes on the leading and lagging strands can be selectively targeted to measure their different transcription levels when replication is impaired versus non-impaired.

In some embodiments, quantification of DNA fragments and genes located in proximity to the origin of replication (e.g., the origin itself or proximate genes such as gln udhA dnaB or some rDNA) is performed. In some embodiments, the difference in copy number per cell between antibiotic treated and non-treated cells can be detected by the methods and devices described herein (e.g., digital amplification).

In some embodiments, DNA targets located in proximity to the termination site of replication (ter) are quantified. Because they are the last parts of the genome to replicate, these regions tend to show lesser variation in copy number based on cell growth state, or the presence of antibiotics. In some embodiments, measurement of replication of DNA targets near ter can be used to standardize data obtained from other targets. For example, in some embodiments, at short drug exposure times, not sufficient to replicate the entire genome, these ter-proximal regions can be used as a measure of the loaded cell numbers while regions closer to ori can be used to access DNA replication and resistance to the drug; this is useful for example when the number of cells loaded is low (for example, less than 100 or less than 10) and therefore difficult to measure. In some embodiments, variations in copy number of these regions with and/or without treatment with a drug are used to distinguish resistant from susceptible bacteria. Drugs, such as antimicrobials, that cause the replication fork to fail can further amplify this effect. In some embodiments, replication of a target nucleic acid sequence can be used to determine the resistance profile of genes in cells (such as bacteria) incubated in the presence of a drug (such as an antibiotic).

In some embodiments, the relative quantification of these targets with and/or without treatment with antibiotics will be used to determine antibiotic susceptibility. This can enable the very rapid differentiation between resistant and susceptible strains.

In some embodiments, such as when a cell's new replication fork starts from origin of replication, other older replication forks can continue replication independently on re-initiation event. (Fossum, S., E. Crooke, et al. (2007). "Organization of sister origins and replisomes during multifork DNA replication in *Escherichia coli*." The EMBO Journal 26(21): 4514-4522. Mohan C. Joshi, et al, 2010, "*Escherichia coli* sister chromosome separation includes an abrupt global transition with concomitant release of late-splitting intersister snaps", PNAS, vol. 108 no. 7,2765-2770). Thus, in some embodiments, a gene target used for drug resistance/susceptibility testing can be located distantly from the origin (e.g. oriC would still be replicated fast enough for determination of drug resistance/susceptibility).

Figure 3:
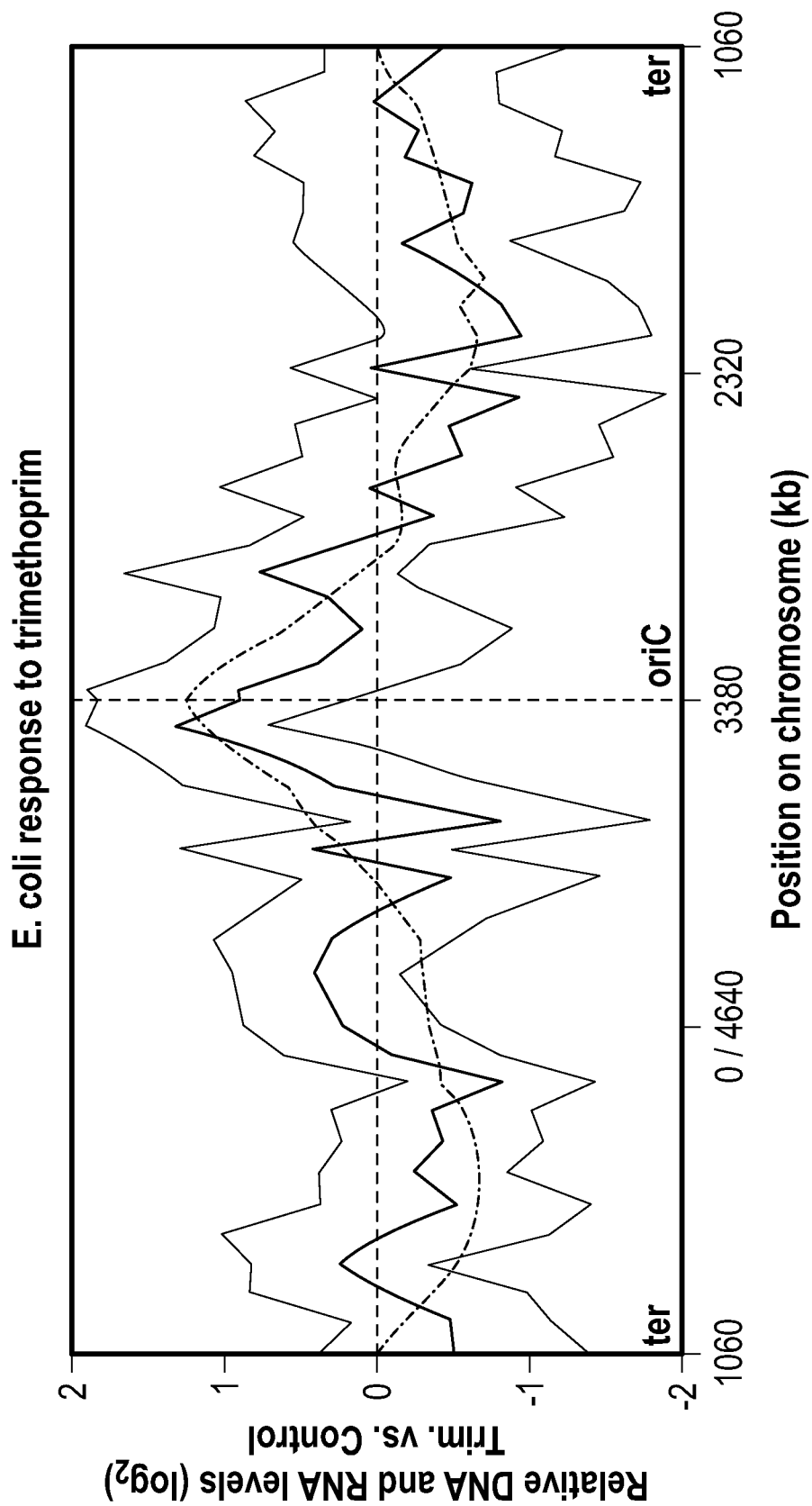
FIG. 3 illustrates the effect of a drug on DNA and RNA levels based on proximity to the origin of replication in susceptible cells.

By using targets close to the origin of replication, the relative copies number of those genes in total genetic material in the cells can be quantified to identify susceptible and resistant cells under antibiotic treatment earlier prior to completion of DNA replication or prior to completion of cell division. In some embodiments, the copy number of the target genes of the susceptible organism treated with a drug is less than the copy number of the target genes of the resistant organism or the non-treated organism as exposure to the drug in a susceptible organism decreases replication. However, some antibiotics cause certain regions of chromosomal DNA to increase in copy number in susceptible cells. FIG. 3 illustrates the effect of susceptible cells to antibiotic dosing, specifically the relative DNA copy number in *E. coli* after treatment with trimethoprim as compared to the distance from the origin of replication (oriC), shown as the line that intersects with 0 at both ter regions. (Slager, J., M. Kjos, et al. (2014). "Antibiotic-Induced Replication Stress Triggers Bacterial Competence by Increasing Gene Dosage near the Origin." Cell 157(2): 395-406). FIG. 3 shows that DNA copy number peaks close to the origin of replication after exposure to trimethoprim as compared to baseline level of zero.

Figure 4:
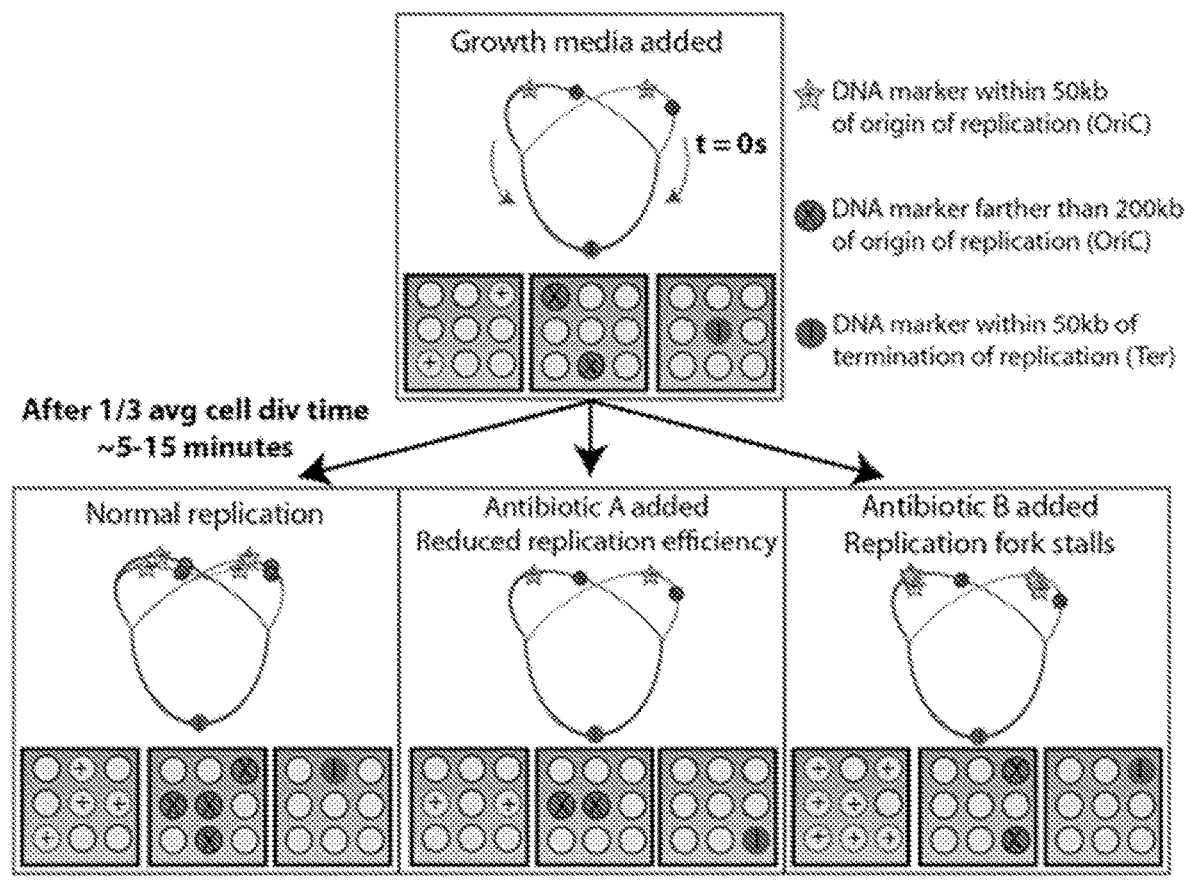
FIG. 4 depicts the effects of no antibiotic, Antibiotic A, and antibiotic B on replication efficiency, replication fork stalls, and digital detection results for targets with different distances from the origin of replication from a single cell.

Many antibiotics (such as quinolones) induce a replication fork stalling. As a direct consequence of replication fork stalling while DNA replication initiation continues, all antibiotics targeting DNA replication up-regulate origin-proximal genes copy number and induce a global changes in transcription in bacteria. This produces a result contrary to those antibiotics that slow DNA replication in susceptible organisms treated with a drug, providing an increase in the number of positive results. Predicted results of the digital assay described herein for antibiotics that slow growth, and those that induce a replication fork stalling are shown in FIG. 4. In FIG. 4, "Antibiotic A" represents antimicrobials that result in a reduced replication efficiency in susceptible cells, thus lowering the number of gene copy near the origin of replication compared to resistant cells. "Antibiotic B" represents antimicrobials that result in a replication fork stalling in a cell, resulting in an increase in initiation of new replication near the origin of replication, thus increasing the copy number of genes near the origin of replication in susceptible cells as compared to resistant cells.

"Antibiotic A," as represented in FIG. 4, includes bacteriostatic antibiotics (such as aminoglycosides, cephalosporins, tetracyclines, sulfonamides, and macrolides) that inhibit protein synthesis, and bactericidal antibiotics that act on the cell wall (eg, vancomycin and β-lactams). For these antibiotics that slow DNA replication, in some embodiments, the antibiotic exposure is altered to induce oxidation stress in the cells, e.g., by controlling concentrations of Ferrous iron, pH and Magnesium ions, and ensuring aerobic conditions.

"Antibiotic B," as represented in FIG. 4, includes antibiotics that cause certain regions of chromosomal DNA to increase in copy number in susceptible cells. For example, oriC-ter ratios are known to be affected by some antibiotics treatment (e.g., HPUra, hydroxyurea, trimethoprim, ciprofloxacin, and MMC) in *B. cereus, S. aureus*, and *E. coli* and *S. pneumoniae*. These antibiotics are known to impair chromosome replication, as trimethoprim affects DNA replication indirectly. Nitrofurantoin directly impairs many cell processes including replication. 6(p-Hydroxyphenylazo)-uracil (HPUra) is a selective inhibitor of gram-positive bacteria DNA. Hydroxycarbamide decreases the production of deoxyribonucleotides. Ciprofloxacin is a fluoroquinolone that stalls the replication fork and causes DNA fragmentation due to its interactions with DNA gyrase and topoisomerase. (Slager, J., M. Kjos, et al. (2014). "Antibiotic-Induced Replication Stress Triggers Bacterial Competence by Increasing Gene Dosage near the Origin." Cell 157(2): 395-406, and Tamayo M, Santiso R, Gosalvez J, Bou G, Fernandez J L. Rapid assessment of the effect of ciprofloxacin on chromosomal DNA from *Escherichia coli* using an in situ DNA fragmentation assay. BMC Microbiology. 2009; 9:69).

The resistance or susceptibility of a call to either type of antibiotic can be detected using the methods and devices described herein. Furthermore, digital PCR will provide a different result depending upon whether or not the genes copied before the replication fork stall are fragmented from the chromosomal or plasmid DNA. If they are not fragmented, they cannot separate into distinct wells, thus providing an additional level of resolution to characterize the cells. The DNA fragments liberated from the nucleoid under different antibiotics treatment are estimated to be of 50 to 100 kb size (Tamayo M, Santiso R, Gosalvez J, Bou G, Fernandez J L. Rapid assessment of the effect of ciprofloxacin on chromosomal DNA from *Escherichia coli* using an in situ DNA fragmentation assay. BMC Microbiology. 2009; 9:69) similar to the presumed size of the DNA loops of the nucleoid and to the prominent DNA gyrase-mediated cleavage sites (Snyder M, Drlica K. DNA gyrase on the bacterial chromosome: DNA cleavage induced by oxolinic acid. J Mol Biol. 1979; 131(2):287-302, Condemine, Smith C L. Transcription regulates oxolinic acid-induced DNA gyrase cleavage at specific sites on the *E. coli* chromosome. Nucleic Acids Res. 1990; 18(24):7389-7396, and Hsu Y-H, Chung M-W, Li T-K. Distribution of gyrase and topoisomerase IV on bacterial nucleoid: implications for nucleoid organization. Nucleic Acids Res. 2006; 34(10):3128-3138.).

In some embodiments, the method disclosed herein is used to detect genes and gene fragments that are locally amplified in short timeframes to distinguish drug resistant from drug susceptible cells. In some embodiments, the method makes use of the fact that some antibiotics cause the preferential amplification of DNA fragments located near origin of replication, such as some competence genes and the origin of replication itself. In some embodiments DNA fragments or genes located within 50-200 kb from the origin of replication in both replichores will be quantified in digital format from a small number of cells to determine their drug susceptibility. In some embodiments, the method makes use of the fact that some antibiotics cause accumulation of DNA fragments. This has been shown to be caused by antibiotics that cause the replication fork to stall. This can be analyzed through quantification of genes inside the accumulated region, outside the accumulated region, or a ratio between both.

In some embodiments, the change in the relative replication rates for selected positions on the chromosome can be detected in susceptible isolates after less than 20 minutes of exposure to a drug. In some embodiments, the difference in in the relative replication rates for selected positions on the chromosome can be discernable only after a certain time point, which can differ for different antibiotics types, organisms, cells and/or drugs. In some embodiments, the change in relative replication rates for selected positions on the bacterial chromosome can be detected in susceptible isolates after less than 5, 10, 15, 20, 25, 30, 45, 60, 90, 120, 150, or 180 minutes of exposure to a drug.

In some embodiments shift up protocol (for example one that adds nutrients and signaling molecules to stimulate growth and gene expression and DNA replication), can be used to ensure some control over the time of re-initiation of replication.

In some embodiments, changes in gene expression are used as markers of antimicrobial susceptibility or resistance in an organism. In some embodiments, drug susceptibility testing is based on RNA, such as by comparing transcription levels. In some embodiments, drug susceptibility testing is based on RNA, such as by comparing transcription levels using digital quantification. In some embodiments, markers associated with a resistance or susceptibility in response to an antimicrobial can be measured.

in some embodiments, genes differently regulated in response to a drug or antibiotic can be used. The genes can include for example, the recA and LexA (Barczak, et al, 2012, Proceedings of the National Academy of Sciences, 6217-6222) genes induced by OxyR and SoxS in response to antibiotic-induced oxidative stress (Dwyer, et al 2014, Proceedings of the National Academy of Sciences, E2100-E2109).

In susceptible bacteria, many RNA targets have been shown to be either upregulated or downregulated in response to drug exposure over a short time. Many such genes also show significant changes in expression level as a response to variations in culture conditions and from isolate to isolate. Some genes expression (e.g., recA, involved in the SOS response) are upregulated in several species in response to multiple antibiotics, whereas other transcriptional changes are organism and/or mechanism specific.

Changes in RNA targets RNA levels (through qPCR, micro arrays, RNAseq) can be difficult to detect using existing methods after a short time of drug/antibiotic treatment in bulk (such as by routine reverse transcription and isothermal or PCR amplification) due to the presence of non-specific nucleic acids from the host's cells or from other microorganisms, as well as due to the presence of inhibitors from the clinical sample, and due to the short time of treatment. In some embodiments, binary, digital and multi-volume digital formats can be used to isolate targets in volumes where local concentration is high, enabling the fast and reliable quantification even in such samples.

In some embodiments, DNA targets with a higher copy number present in cells will be used to enable the detection of resistance profiles even in very low numbers of cells (such as in blood or cerebral spinal fluid). For example, while in genome of most of the *E. coli* strains and isolates there are ~7 copies of rDNA, due to the presence of at least two, but potentially numerous replication forks, one could expect to have, in some cases, from 12 to 35 rDNA copies per cell, depending on its growth rate (*E. coli* and *Salmonella*, cellular and molecular biology. Frederic C. Neidhardt, editor in Chief. v2. ASM press, Washington D.C. 1996). In some embodiments, using genes with higher copy number in the cell will enable the increased statistical resolution of quantification to determine antibiotic resistance when very low numbers of cells are present. In some embodiments, this is quantification is performed by amplification. In some embodiments, this quantification makes use of digital amplification methods.

In some embodiments, additional targets are evaluated from publically available studies such as those published by the Broad Institute. In some embodiments, targets for analysis are generated from analysis of DNA/RNA-seq data. In some embodiments, quantification strategies (such as e.g. NASBA, qRT-PCR, sequencing, nanostring, among others) can be used. In some embodiments RNA from cells obtained from samples in a digital format is quantified. In some embodiments gene target expression levels in each individual cell is quantified through single cell measurements.

An exemplary list of RNA targets that can be used for multiplexed and/or individual use for evaluating a cells' response to a drug (e.g., ciprofloxacin) are provided in Table 1

TABLE 1

| Gene | Response to Ciprofloxacin |
| --- | --- |
| EcHS_A0999_dmsA_anaerobic_dimethyl_sulfoxide_reductase,_A_subunit | Same or Downregulated |
| EcHS_A1247_pepT_peptidase_T | Same or Downregulated |
| EcHS_A1333_narK_nitrite_extrusion_protein_1 | Same or Downregulated |
| EcHS_A1334_narG_nitrate_reductase,_alpha_subunit | Same or Downregulated |
| EcHS_A1335_narH_nitrate_reductase,_beta_subunit | Same or Downregulated |
| EcHS_A1557_fdnG_formate_dehydrogenase,_nitrate_inducible,_alpha_subunit,_selenocysteine-containing | Same or Downregulated |
| EcHS_A1755_-_hypothetical_protein | Same or Downregulated |
| EcHS_A1987_flhC_transcriptional_activator_FlhC | Same or Downregulated |
| EcHS_A1988_flhD_transcriptional_activator_FlhD | Same or Downregulated |
| EcHS_A2346_napF_ferredoxin-type_protein | Same or Downregulated |
| EcHS_A2342_napH_quinol_dehydrogenase_membrane_component | Significantly Downregulated |
| EcHS_A2343_napG_quinol_dehydrogenase_periplasmic_component | Significantly Downregulated |

TABLE 1-continued

| Gene | Response to Ciprofloxacin |
|---|---|
| EcHS_A2380_glpT_sn-glycerol-3-phosphate_transporter | Significantly Downregulated |
| EcHS_A2381_-_hypothetical_protein | Significantly Downregulated |
| EcHS_A2382_glpA_sn-glycerol-3-phosphate_dehydrogenase_subunit_A | Significantly Downregulated |
| EcHS_A2597_aegA1_oxidoreductase_Fe—S_binding_subunit | Significantly Downregulated |
| EcHS_A3117_ansB_L-asparaginase_II | Significantly Downregulated |
| EcHS_A3561_nirB_nitrite_reductase_[NAD(P)H],_large_subunit | Significantly Downregulated |
| EcHS_A3562_nirD_nitrite_reductase_small_subunit | Significantly Downregulated |
| EcHS_A3605_feoA_ferrous_iron_transport_protein_A | Significantly Downregulated |
| EcHS_A3606_feoB_ferrous_iron_transport_protein_B | Significantly Downregulated |
| EcHS_A3607_-_hypothetical_protein | Significantly Downregulated |
| EcHS_A3616_malT_transcriptional_regulator_MalT | Significantly Downregulated |
| EcHS_A4395_frdD_fumarate_reductase_subunit_D | Significantly Downregulated |
| EcHS_A1940_-_DNA_damage-inducible_protein_YebG | Significantly Upregulated |
| EcHS_A2835_recA_recombinase_A | Significantly Upregulated |
| EcHS_A4283_lexA_LexA_repressor | Significantly Upregulated |
| EcHS_A4284_dinF_DNA-damage-inducible_SOS_response_protein | Significantly Upregulated |
| EcHS_A4300_uvrA_excinuclease_ABC_subunit_A | Significantly Upregulated |
| EcHS_A2341_napB_citrate_reductase_cytochrome_c-type_subunit | Requires Evaluation |
| EcHS_A2344_napA_nitrate_reductase_catalytic_subunit | Requires Evaluation |
| EcHS_A3610_gntX_gluconate_periplasmic_binding_protein | Requires Evaluation |
| EcHS_A3612_-_hypothetical_protein | Requires Evaluation |
| EcHS_A3821_secB_preprotein_translocase_subunit_SecB | Requires Evaluation |
| EcHS_A4404_rsgA_ribosome-associated_GTPase | Requires Evaluation |
| EcHS_A4424_-_23S_rRNA_(guanosine-2'-O)-methyltransferase | Requires Evaluation |
| 23S rRNA | Requires Evaluation |
| EcHS_A3544_-_hypothetical_protein | Requires Evaluation |
| EcHS_A0467_phoB_transcriptional_regulator_PhoB | Requires Evaluation |
| EcHS_A0468_phoR_phosphate_regulon_sensor_protein | Requires Evaluation |
| EcHS_A1067_sulA_SOS_cell_division_inhibitor | Requires Evaluation |
| EcHS_A3855_DNA-damage-inducible protein D_DinD | Requires Evaluation |
| EcHS_A2357_two-component response regulator RscB | Requires Evaluation |
| EcHS_A1184_dinI_DNA_damage-inducible_protein_I | Requires Evaluation |
| EcHS_A4417_FtsH_protease_regulator_HflC | Requires Evaluation |

In some embodiments of the devices, reactive species can be used to detect an oxidative stress in every single cell. Because non-viable cells cannot maintain a reducing environment in the cytoplasm, oxidation-sensitive dyes make up the majority of viability assays.

In some embodiments the devices and methods disclosed herein can be used to detect an increase in expression of genes up-regulated by OxyR and SoxR transcription factors as an evidence of antibiotic-induced oxidative stress response. These genes examples are such as for example sodA (encoding Mn— cofactored superoxide dismutase) and acrAB (encoding a multidrug efflux pump), soxS (secondary transcription factor), and KatG and Ahp genes, OxyS, RecA.

In some embodiments RNA targets and/or their genes involved in Fe ions transport and regulation are selected. In some embodiments, RNA targets and/or their genes involved in oxidation stress response are selected.

FeoB is a ferrous iron uptake system belonging to the Ferrous Iron Uptake (FeoB) transporter family (Kammler M, Schon C, Hantke K. Characterization of the ferrous iron uptake system of Escherichia coli. Journal of Bacteriology. 1993; 175(19):6212-6219). FeoB is one of the numerous genes which transcription is reported to be down-regulated in response to ciprofloxacin treatment in RNAseq analysis of E. coli isolates total RNA expression. (Shishkin, A. A., G. Giannoukos, et al. (2015). "Simultaneous generation of many RNA-seq libraries in a single reaction." Nat Meth 12(4): 323-325). FeoB transcription is known to be under repression by Fur. In some embodiments, targets are selected out of those genes activated or repressed by Fur.

FeoB expression is also activated by RstAB two component system. In some embodiments, targets will be selected out of those genes activated or repressed by the RastAB two component system.

In some embodiments, the pH and Mg2+ concentrations of medium used to expose cells to antibiotic will be increased or decreased in conjunction with methods described herein to enhance the cellular response to antibiotics. In some embodiments bacterial cells are treated in relatively low Mg 2+, low pH (mild acidic conditions), and different selected controlled levels of Fe, to increase amplitude of changes in FeoB expression in response to antibiotics.

In some embodiments, the methods described herein comprise the steps of 1) pre-incubating cells in low Mg and low Fe (2+) and low pH (mild acidic conditions), and 2) adding antibiotic together with high Fe(2+). In some embodiments, the method comprises 1) pre-incubating cells low Mg and high Fe (2+) and low pH (mild acidic conditions), and 2) adding antibiotic.

In some embodiments, tuning of dissolved oxygen, PH, Fe2+, silver ions concentrations, Mg2+ concentrations, and other salts concentrations is performed to optimize conditions for the fastest/most reliable AST through measuring FeoB expression levels. These variations can be combined with the gene expression targets mentioned in this document. This will enable the higher resolution determination of antibiotic susceptibility by quantification of these targets. In some embodiments air/oxygen is provided to the bacteria incubated in a presence of antibiotics. In some embodiments, oxidative stress is enhanced in the bacteria via addition of peroxides.

In some embodiments, the target analyte can comprises an individual target or a group of targets, e.g. RNA from a group of genes coding for the proteins with the similar function (such as group of genes mentioned above and linked to iron metabolism) responding to pH, $Mg^{2+}$ and oxidative stress. In some embodiments, the target analyte will comprise RNA from a group of genes relevant to oxidative stress (oxidation stress).

In some embodiments the recA gene and/or recA RNA are quantified to determine antibiotic susceptibility. In some embodiments, other genes in the SOS response are used as targets for quantification to determine antibiotic susceptibility. In some embodiments FeoB RNA and/or recA RNA are quantified to determine antibiotic susceptibility. In some embodiments FeoB RNA and recA RNA are quantified, detecting their ratio to determine antibiotic susceptibility and resistance. In some embodiments other genes up regulated and down regulated in response to antibiotics are quantified together and their ratio is detected to determine antibiotic susceptibility or resistance in a microorganism.

In some embodiments, the devices use a combination of precursor rRNA and ribosomal RNA markers for detecting resistant and susceptible cells or microorganisms with real-time RT-PCR on single cells. In some embodiments, the devices can integrate a combination of markers for universal drug-susceptibility and/or specific drug-resistance detection.

Sample Processing

In some embodiments, the microorganism is exposed to a drug to assay its response to the drug and determine whether the microorganism is resistant or susceptible to the drug. In some embodiments, isolates can be pre-cultured in or pre-exposed to a variety of matrices (such as for example bacterial culture media or human urine, among others), and can be subsequently incubated in the presence or absence of various drugs (e.g. antibiotics, such as ciprofloxacin, nitrofurantoin, trimethoprim, tetracycline, and sulfamethoxazole, and others.) where exposure to multiple drugs and/or multiple additives is performed on the same device substantially simultaneously. In some embodiments, microorganisms do not substantially divide during exposure to a drug. In some embodiments, microorganisms confined as single cells, or being in the small group and/or aggregate of cells, respond to a drug faster than an average population.

Devices and methods described herein can include those when some of the microorganisms confined as single cells, or as a small group and/or aggregate of cells, such as for example fewer than 3 cells, fewer than 10 cells, fewer than 30 cells, fewer than 100 cells in the same compartment. The volume of the compartment can be in the range of 100 fL to 1 nL, 1 nL to 100 nL, or 100 nL to 500 nL.

In some embodiments, digital assays can use the confinement of single cells from a sample into clonal isolation regions. In some embodiments, each of the isolated cells are cultured in the clonal isolation regions to generate a plurality of clonal populations from the sample. In some embodiments, the isolated cells are treated with a drug before or after expansion. In some embodiments, after culture and expansion from an isolated cell, the clonal population is divided into two or more treatment regions. As such, at least one portion of the clonal population can be treated with a drug, while another portion of the clonal population is not treated with a drug. Then, the assays described herein can be performed to determine whether the cells in the clonal population are susceptible or resistant to one or more drugs.

In some embodiments, specific culturing conditions are used to speed up a microorganism's response to a drug (e.g. quorum sensing molecules, gas partial pressures, temperature, etc). In some embodiments, the microorganism is exposed gases or gas mixtures, e.g., containing $H_2S$, CO, and NO. Such gases are known, for example, to affect susceptibility of microorganisms to antibiotics. Such gases can be diluted with a gas mixture which could be anaerobic, aerobic, or microoxic. Such gas mixture can contain $CO_2$.

In some embodiments, co-culturing of the microorganism with eukaryotic cell and/or other microorganism is used to speed up a microorganism's response to a drug.

In some embodiments, measures to control the average number and/or location and/or time of initiation of replication in culture are performed. For example, cells can be placed into high- or low-nutrient conditions prior to exposure to antibiotics. In some embodiments, the acclimatization of cells to changes in growing conditions (such as, for example, mixing infected blood with nutrient rich media) will cause variation in the rate of DNA replication. In some embodiments, this effect can be mitigated by the modification of growth media. In some embodiments, data analyses can allow the capture of changes in replication rates over this noise. In some embodiments, the effects of media on replication can be used to enhance the effect of a drug treatment.

In some embodiments, cells are exposed to antibiotics as follows: Cells are pre-cultured at 37° C. to a density of up to $10^9$ cells/mL in various matrices including Bacto Brain-Heart Infusion broth (BHI), a mix of BHI and pooled human urine, and whole human urine before being diluted and incubated with or without antibiotics. The antibiotics used for treatment include ciprofloxacin, nitrofurantoin, trimethoprim, tetracycline, and sulfamethoxazole. Incubations were performed at 37° C. at starting concentrations ranging from $10^5$-$10^8$ cells/mL, and then treated with concentrations of antibiotics ranging from 0.75 ug/mL-156 ug/mL depending on the treatment. Cells were incubated with and without antibiotics for a period of time including 10 minutes, 15 minutes, 20 minutes, 30 minutes, 45 minutes, or 60 minutes before an aliquot of the culture was used for nucleic acid extraction.

In some embodiments, the microorganism is exposed to a drug for a time less than 4 hours, less than 3 hours, less than 2 hours, less than 1 hour, less than 30 minutes, less than 15 minutes, less than 10 minutes, less than 5 minutes, less than 3 minutes, or less than 1 minute.

The nucleic acids can be extracted before analysis. The exact protocol used to extract nucleic acids depends on the sample and the exact assay to be performed. Extracting nucleic acids from target bacteria usually involves a cell lysis step followed by nucleic acid purification. The cell lysis step disrupts the cell and nuclear membranes, releasing the genetic material. This is often accomplished using a lysis detergent, such as sodium dodecyl sulfate, which also denatures the large amount of proteins present in the cells.

The nucleic acids can then be purified with an alcohol precipitation step, usually ice-cold ethanol or isopropanol, or via a solid phase purification step, typically on a silica matrix in a column, resin or on paramagnetic beads in the presence of high concentrations of a chaotropic salt, prior to washing and then elution in a low ionic strength buffer. An optional step prior to nucleic acid precipitation is the addition of a protease which digests the proteins in order to further purify the sample.

In some embodiments, nucleic acids are extracted using standard methods including a one-step DNA extraction buffer or a one-step RNA extraction buffer (available from Epicentre). Following extraction, nucleic acids were quantified using nucleic acid amplification techniques including quantitative PCR and digital PCR.

In some embodiments, the microorganisms of the sample are lysed. In some embodiments, inhibitors are removed from the sample. In some embodiments, inhibitors in the sample are inactivated. In some embodiments, the sample is exposed to conditions or reagents for preventing degradation of the nucleic acid. In some embodiments, the sample undergoes ribosomal RNA depletion. IN some embodiments, unwanted RNA is removed from the sample. IN some embodiments, microorganisms in the sample are treated with a reagent that binds to and prevents amplification of free nucleic acids, such as PMA and EMA. In some embodiments, the sample is irradiated to initiate photochemical reaction to prevent the amplification of unwanted nucleic acids. In some embodiments, extracted nucleic acids are further purified prior to quantification.

In some embodiments sample preparation before the quantification reaction takes less than two hours, less than one hour, less than 30 minutes, less than 15 minutes, less than 10 minutes, less than 5 minutes, less than 3 minutes, less than 1 minute, or less than 30 seconds In some embodiments techniques such as denaturation, restriction digestion, fragmentation, digestion of replicated DNA fragments are used before digital quantification. This enables enhanced isolation of individual genes into individual volumes for detection and amplification. In some embodiments, a restriction digest in between genes is used to facilitate isolation into individual volumes of DNA molecules carrying target genes. For example, in some embodiments, using as the target rDNA in E. coli with 7 copies per genome, a digital experiment can only show one positive volume per large genome fragment. When the genome is denatured, fragmented, and/or digested, each gene could be isolated into individual volumes, giving 24 to 70 template-positive volumes for analyses in a device from a single genome.

In some embodiments agents inhibiting amplification of nucleic acids from dead cells will be used (e.g., propidium monoazide (PMA) or ethidium monoazide). In some embodiments, cells will be treated with such agents inhibiting amplification of nucleic acids from dead cells prior to incubation with antibiotics. In some embodiments, cells will be treated with such agents inhibiting amplification of nucleic acids from dead cells after incubation with antibiotics.

In some embodiments, a restriction digest of chromosomal DNA is done prior to quantification, such as to separate fragments of DNA containing multiple replicated copies of the target gene while preserving the fragments of interest to be suitable for detection and quantification.

In some embodiments, one or more denaturation steps are done, such as to duplicate the number of positive templates (for example if in a given sample E. coli cells could have from 12 to 35 copies of rDNA genes under certain conditions (depending on a growth rate, individual ages and individual states)—and yield for example 24-70 fragments after denaturation; this can in some cases improve visualization in digital approaches.)

In some embodiments, denaturation or digestion can be used to separate DNA at replication forks—pieces of newly replicated DNA can partition into different wells—such as to increase the resolution between inhibited cells and actively replicating cells.

In some embodiments, digital assays can use the confinement of a few or single target nucleic acid molecules into individual reaction volumes. Prior to the completion of replication, denaturing agents (such as e.g. heat, urea, Guanidinium Chloride, acids, bases, mechanical strain, enzymes, restriction enzymes, among others) can be used to enhance the separation of target DNA strands into independent volumes. This can be of particular use for example in cases where multiple target regions are present within a single genome.

In some embodiments, denaturation of a whole chromosomal DNA is performed before performing digital quantification.

Amplification

In some embodiments, a nucleic acid amplification reaction is performed to amplify the target analyte (e.g., a target nucleic acid). Amplification reaction can include polymerase chain reaction (PCR), nucleic acid sequence based amplification (NASBA), self-sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR or ligation mediated PCR. Amplification or detection methods for nucleic acids can include but are not limited to PCR, RT-PCR, or other methods including isothermal amplification methods. Isothermal nucleic acid amplification methods can include but are not limited to strand displacement amplification (SDA), transcription mediated amplification, nucleic acid sequence based amplification (NASBA), recombinase polymerase amplification (RPA), rolling circle amplification, ramification amplification, helicase-dependent isothermal DNA amplification, loop mediated isothermal amplification (LAMP), methods based on both signal amplification and target amplification such as branched-DNA-based detection methodologies, hybridization chain reaction, or nucleic acid-based logic gates and DNA circuits (see, e.g., Qian and Winfree, Scaling Up Digital Circuit Computation with DNA Strand Displacement Cascades, Science 2011; 6034: 1196-1201).

The amplification reaction assay can be PCR. PCR is well known in this field and comprehensive description of this type of reaction is provided in E. van Pelt-Verkuil et al., Principles and Technical Aspects of PCR Amplification, Springer, 2008.

PCR is a powerful technique that amplifies a target DNA sequence against a background of complex DNA. If RNA is to be amplified (by PCR), it must be first transcribed into cDNA (complementary DNA) using an enzyme called reverse transcriptase. Afterwards, the resulting cDNA is amplified by PCR.

PCR is an exponential process that proceeds as long as the conditions for sustaining the reaction are acceptable. The components of the reaction are:
1. pair of primers—short single strands of DNA with around 10-30 nucleotides complementary to the regions flanking the target sequence
2. DNA polymerase—a thermostable enzyme that synthesizes DNA
3. deoxyribonucleoside triphosphates (dNTPs)—provide the nucleotides that are incorporated into the newly synthesized DNA strand
4. buffer—to provide the optimal chemical environment for DNA synthesis.

In embodiments using PCR, the components of the reaction can be in contact with sample. The components of the reaction can be added to a container that holds the sample. The components of the reaction can be present in a container, and the sample can be added. In some embodiments, a kit can comprise a plurality of small containers, at least one container holding the components of a PCR reaction. A kit can comprise a SlipChip and the components of the reaction.

PCR typically involves placing these reactants in a small tube (10-50 microlitres) containing the extracted nucleic acids. The tube is placed in a thermal cycler; an instrument that subjects the reaction to a series of different temperatures for varying amounts of time. The standard protocol for each thermal cycle involves a denaturation phase, an annealing phase, and an extension phase. The extension phase is sometimes referred to as the primer extension phase. In addition to such three-step protocols, two-step thermal protocols can be employed, in which the annealing and extension phases are combined. The denaturation phase typically involves raising the temperature of the reaction to 90-95° C. to denature the DNA strands; in the annealing phase, the temperature is lowered to ~50-60° C. for the primers to anneal; and then in the extension phase the temperature is raised to the optimal DNA polymerase activity temperature of 60-72° C. for primer extension. This process is repeated cyclically around 20-40 times, the end result being the creation of millions of copies of the target sequence between the primers.

The amplification reaction assay can be a variant of PCR. The amplification reaction assay can be selected from the group of variants to the standard PCR protocol such as multiplex PCR, linker-primed PCR, direct PCR, tandem PCR, real-time PCR and reverse-transcriptase PCR, amongst others, which have been developed for molecular diagnostics.

The amplification reaction assay can be multiplex PCR. Multiplex PCR uses multiple primer sets within a single PCR mixture to produce amplicons of varying sizes that are specific to different DNA sequences. By targeting multiple genes at once, additional information can be gained from a single test-run that otherwise would require several experiments.

In some embodiments, a multiplexed PCR reaction is performed where a plurality of primer sets are added to a reaction mixture and each amplify their specified target within the same volume, for example. In other embodiments a sample is split into a plurality of smaller volumes into which single primer sets are introduced.

The amplification reaction assay can be linker-primed PCR, also known as ligation adaptor PCR. Linker-primed PCR is a method used to enable nucleic acid amplification of essentially all DNA sequences in a complex DNA mixture without the need for target-specific primers. The method firstly involves digesting the target DNA population with a suitable restriction endonuclease (enzyme). Double-stranded oligonucleotide linkers (also called adaptors) with a suitable overhanging end are then ligated to the ends of target DNA fragments using a ligase enzyme. Nucleic acid amplification is subsequently performed using oligonucleotide primers which are specific for the linker sequences. In this way, all fragments of the DNA source which are flanked by linker oligonucleotides can be amplified.

The amplification reaction assay can be direct PCR. Direct PCR describes a system whereby PCR is performed directly on a sample without any, or with minimal, nucleic acid extraction. With appropriate chemistry and sample concentration it is possible to perform PCR with minimal DNA purification, or direct PCR. Adjustments to the PCR chemistry for direct PCR include increased buffer strength, the use of polymerases which have high activity and processivity, and additives which chelate with potential polymerase inhibitors.

The amplification reaction assay can be tandem PCR. Tandem PCR utilizes two distinct rounds of nucleic acid amplification to increase the probability that the correct amplicon is amplified. One form of tandem PCR is nested PCR in which two pairs of PCR primers are used to amplify a single locus in separate rounds of nucleic acid amplification. The amplification reaction assay can be nested PCR. The first pair of primers hybridize to the nucleic acid sequence at regions external to the target nucleic acid sequence. The second pair of primers (nested primers) used in the second round of amplification bind within the first PCR product and produce a second PCR product containing the target nucleic acid, that can be shorter than the first one. The logic behind this strategy is that if the wrong locus were amplified by mistake during the first round of nucleic acid amplification, the probability is very low that it would also be amplified a second time by a second pair of primers and thus increases specificity.

The amplification reaction assay can be real-time PCR. The amplification reaction assay can be quantitative PCR. Real-time PCR, or quantitative PCR, is used to measure the quantity of a PCR product in real time. By using a fluorophore-containing probe or fluorescent dyes along with a set of standards in the reaction, it is possible to quantify the starting amount of nucleic acid in the sample. This is particularly useful in molecular diagnostics where treatment options can differ depending on the pathogen load in the sample.

The amplification reaction assay can be reverse-transcriptase PCR (RT-PCR). Reverse-transcriptase PCR (RT-PCR) is used to amplify DNA from RNA. Reverse transcriptase is an enzyme that reverse transcribes RNA into complementary DNA (cDNA), which is then amplified by PCR. RT-PCR can be used in expression profiling, to determine the expression of a gene or to identify the sequence of an RNA transcript, including transcription start and termination sites. It can be used to amplify RNA viruses such as human immunodeficiency virus or hepatitis C virus.

The amplification reaction assay can be isothermal. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. A number of isothermal nucleic acid amplification methods have been developed, including but not limited to Strand Displacement Amplification (SDA), Transcription Mediated Amplification (TMA), Nucleic Acid Sequence Based Amplification (NASBA), Recombinase Polymerase Amplification (RPA), Rolling Circle Amplification (RCA), Ramification Amplification (RAM), Helicase-Dependent Isothermal DNA Amplification (HDA), Circular Helicase-Dependent Amplification (cHDA), Loop-Mediated Isothermal Amplification (LAMP), Single Primer Isothermal Amplification (SPIA), Signal Mediated Amplification of RNA Technology (SMART), Self-Sustained Sequence Replication (3SR), Genome Exponential Amplification Reaction (GEAR) and Isothermal Multiple Displacement Amplification (IMDA). Further examples of such amplification chemistries are described in, for example, ("Isothermal nucleic acid amplification technologies for point-of-care diagnostics: a critical review, Pascal Craw and Wamadeva Balachandrana Lab Chip, 2012, 12, 2469-2486, DOI: 10.1039/C2LC40100B,") incorporated here in its entirety by reference. Isothermal amplification methods that operate at temperatures lower than PCR operating temperatures can be used, e.g., to improve compatibility of restriction enzymes with the amplification process if the restriction enzyme is not sufficiently stable under typical PCR operating temperatures.

Furthermore, detection methods based on both signal amplification and target amplification, such as branched-DNA-based detection methodologies, can be used in this approach. For example, for branched-DNA-based detection methodologies, using an enzyme that can cleave the target in a position located between two positions used for binding of the capture extender and the label extender (e.g., as described in Tsongalis, Branched DNA Technology in Molecular Diagnostics, Am J Clin Pathol 2006; 126: 448-453), can reduce the signal obtained in the assay when a restriction enzyme recognizes and cleaves the target.

The amplification reaction assay can be Strand Displacement Amplification (SDA). Strand Displacement Amplification (SDA) can rely on the ability of certain restriction enzymes to nick the unmodified strand of hemi-modified DNA and the ability of a 5'-3' exonuclease-deficient polymerase to extend and displace the downstream strand. Exponential nucleic acid amplification can then achieved by coupling sense and antisense reactions in which strand displacement from the sense reaction serves as a template for the antisense reaction. The use of nickase enzymes which do not cut DNA in the traditional manner but produce a nick on one of the DNA strands, such as N. Alw1, N. BstNB1 and Mly1, for example, can be used in this reaction. SDA has been improved by the use of a combination of a heat-stable restriction enzyme (Ava1) and heat-stable Exo-polymerase (Bst polymerase). This combination has been shown to increase amplification efficiency of the reaction from $10^8$ fold amplification to $10^{10}$ fold amplification so that it is possible using this technique to amplify unique single copy molecules.

The amplification reaction assay can be Transcription Mediated Amplification (TMA). The amplification reaction assay can be Nucleic Acid Sequence Based Amplification (NASBA). Transcription Mediated Amplification (TMA) and Nucleic Acid Sequence Based Amplification (NASBA) can use an RNA polymerase to copy RNA sequences but not corresponding genomic DNA. The technology can use two primers and two or three enzymes, RNA polymerase, reverse transcriptase and optionally RNase H (if the reverse transcriptase does not have RNase activity). One primer can contain a promoter sequence for RNA polymerase. In the first step of nucleic acid amplification, this primer hybridizes to the target ribosomal RNA (rRNA) at a defined site. Reverse transcriptase can create a DNA copy of the target rRNA by extension from the 3' end of the promoter primer. The RNA in the resulting RNA:DNA duplex can be degraded by the RNase activity of the reverse transcriptase if present or the additional RNase H. Next, a second primer binds to the DNA copy. A new strand of DNA is synthesized from the end of this primer by reverse transcriptase, creating a double-stranded DNA molecule. RNA polymerase recognizes the promoter sequence in the DNA template and initiates transcription. Each of the newly synthesized RNA amplicons re-enters the process and serves as a template for a new round of replication.

The amplification reaction assay can be Recombinase Polymerase Amplification (RPA). In Recombinase Polymerase Amplification (RPA), the isothermal amplification of specific DNA fragments is achieved by the binding of opposing oligonucleotide primers to template DNA and their extension by a DNA polymerase. Heat is not always required to denature the double-stranded DNA (dsDNA) template. Instead, RPA can employ recombinase-primer complexes to scan dsDNA and facilitate strand exchange at cognate sites. The resulting structures are stabilized by single-stranded DNA binding proteins interacting with the displaced template strand, thus preventing the ejection of the primer by branch migration. Recombinase disassembly leaves the 3' end of the oligonucleotide accessible to a strand displacing DNA polymerase, such as the large fragment of *Bacillus subtilis* Pol I (Bsu), and primer extension ensues. Exponential nucleic acid amplification is accomplished by the cyclic repetition of this process.

The amplification reaction assay can be Helicase-dependent amplification (HDA). Helicase-dependent amplification (HDA) mimics the in vivo system in that it uses a DNA helicase enzyme to generate single-stranded templates for primer hybridization and subsequent primer extension by a DNA polymerase. In the first step of the HDA reaction, the helicase enzyme traverses along the target DNA, disrupting the hydrogen bonds linking the two strands which are then bound by single-stranded binding proteins. Exposure of the single-stranded target region by the helicase allows primers to anneal. The DNA polymerase then extends the 3' ends of each primer using free deoxyribonucleoside triphosphates (dNTPs) to produce two DNA replicates. The two replicated dsDNA strands independently enter the next cycle of HDA, resulting in exponential nucleic acid amplification of the target sequence.

The amplification reaction assay can be Rolling Circle Amplification (RCA). Other DNA-based isothermal techniques include Rolling Circle Amplification (RCA) in which a DNA polymerase extends a primer continuously around a circular DNA template, generating a long DNA product that consists of many repeated copies of the circle. By the end of the reaction, the polymerase generates many thousands of copies of the circular template, with the chain of copies tethered to the original target DNA. This allows for spatial resolution of target and rapid nucleic acid amplification of the signal. Up to $10^{12}$ copies of template can be generated in 1 hour. Ramification amplification is a variation of RCA and utilizes a closed circular probe (C-probe) or padlock probe and a DNA polymerase with a high processivity to exponentially amplify the C-probe under isothermal conditions.

The amplification reaction assay can be Loop-mediated isothermal amplification (LAMP). LAMP offers high selectivity and employs a DNA polymerase and a set of four specially designed primers that recognize a total of six distinct sequences on the target DNA. An inner primer containing sequences of the sense and antisense strands of the target DNA initiates LAMP. The following strand displacement DNA synthesis primed by an outer primer releases a single-stranded DNA. This serves as template for DNA synthesis primed by the second inner and outer primers that hybridize to the other end of the target, which produces a stem-loop DNA structure. In subsequent LAMP cycling one inner primer hybridizes to the loop on the product and initiates displacement DNA synthesis, yielding the original stem-loop DNA and a new stem-loop DNA with a stem twice as long. The cycling reaction continues with accumulation of many copies of target in less than an hour. The final products are stem-loop DNAs with several inverted repeats of the target and cauliflower-like structures with multiple loops formed by annealing between alternately inverted repeats of the target in the same strand.

In some embodiments, the amplification is a one-step digital reverse-transcription loop-mediated isothermal amplification (dRT-LAMP) reaction for quantifying mRNA with all reactions performed. LAMP produces a bright fluorescence signal through replacement of manganese with magnesium in calcein. In some embodiments, this fluorescence can then be detected and counted using a commercial cell phone camera.

Nucleic acid-based logic gates and DNA circuits can be used for nucleic acid amplification. The use of restriction enzymes with nucleic acid-based logic gates and DNA circuits can reduce or stop the intrinsic leakage problem for DNA networks. Combining the molecular recognition ability of both restriction enzymes and DNA networks, restriction enzyme logic gates can be highly active components for the design and construction of biocomputational devices (see e.g., Qian and Winfree, Scaling Up Digital Circuit Computation with DNA Strand Displacement Cascades, Science 2011; 6034: 1196-1201).

In some embodiments the amplification employed can take place in a variety of different mediums, such as for example, aqueous solution, polymeric matrix, solid support, etc Detection Assay results can comprise a readout or detection mechanism chosen from a range of readouts used to detect progress or results of reactions, including but not limited to optical techniques, electrical techniques or magnetic techniques. Examples include but are not limited to electrochemical readouts, optical readouts, including for example fluorescence readouts, colorimetric readouts, chemiluminescence, electrical signals, quenching, probe binding, probe hybridization, metal labeling, contrast agent labeling, absorbance, mass spectrometry, sequencing, lateral flow strips, and the generation of a heterogeneous substance (e.g., precipitation, gas bubble).

A readout mechanism can comprise fluorescence. For example fluorescent dye can be used to label nucleic acids; reactions with more nucleic acid product can yield more fluorescence signal. Fluorescent dyes can include but are not limited to ethidium bromide, berberine, proflavine, daunomycin, doxorubicin, thalidomide, YOYO-1, SYBR Green I, SYBR Green II, oxazole yellow (YO), thiazole orange (TO), PicoGreen (PG), TOTO, TO-PRO, SYTOX, SYTO, other cyanine dyes, and calcein. The fluorescence intensity can be measured at an end-point or in real-time, allowing measurement of the reaction progress. For example, a given level of fluorescence can be set as the threshold for a positive signal from a digital or quasi-digital compartment.

In some cases, signal can be generated from molecules with reporter moieties and affinity moieties that are applied to digital units to bind to captured target analyte. The reporter molecule or reporter moiety can be fluorescent. The digital units or capture regions can be washed to remove unbound reporter. In some cases, the reporter molecule can be calcein or calcein with cetyl trimethyl ammonium bromide (calcein-CTAB). In some cases, the reporter can be an intercalating dye. Target analytes can be labeled with enzymes which can produce an electrical signal, for example by electro-activating a substrate molecule which can be oxidized and reduced. Labeling can occur by binding with an affinity agent, for example as in a sandwich assay. Labeling can occur by intercalating dyes.

A readout mechanism can comprise mass spectrometry. For example, nucleic acids of different sizes (e.g. from restriction digestion or ligation) can be distinguished and/or counted by mass spectrometry. Alternatively, a readout mechanism can operate without mass spectrometry.

A readout mechanism can comprise electrophoresis, including gel electrophoresis. For example, nucleic acids of different sizes (e.g. from restriction digestion or ligation) can be identified or distinguished by electrophoresis. Alternatively, a readout mechanism can operate without electrophoresis.

A readout mechanism can comprise sequencing. Sequencing, or sequence determination techniques, can be performed by methods including but not limited to Sanger sequencing, Illumina (Solexa) sequencing, pyrosequencing, next generation sequencing, Maxam-Gilbert sequencing, chain termination methods, shotgun sequencing, or bridge PCR; next generation sequencing methodologies can comprise massively parallel signature sequencing, polony sequencing, SOLiD sequencing, Ion Torrent semiconductor sequencing, DNA nanoball sequencing, Heliscope single molecule sequencing, single molecule real time (SMRT) sequencing, nanopore DNA sequencing, tunneling currents DNA sequencing, sequencing by hybridization, sequencing with mass spectrometry, microfluidic Sanger sequencing, microscopy-based techniques, RNA polymerase sequencing or in vitro virus high-throughput sequencing.

The signal can be electromagnetic. The signal can comprise the presence or absence of a physical object, such as a bead. Captured target analytes can be labeled with a fluorescent agent or a contrast agent. Target analytes can be labeled with enzymes which can produce a fluorescent signal. Target analytes can be labeled with enzymes which can produce a color change in a substrate, producing a colorimetric signal. In some cases, signal can be generated from reporter molecules that are bound to affinity molecules and applied to digital units to bind to captured target analyte.

Sequencing reads can be used to identify reaction products, and the number of sequencing reads generated for a given nucleic acid product can be used to evaluate the reaction. For example, a given number of sequencing reads can be set as the threshold for a positive signal from a digital or quasi-digital compartment. Alternatively, a readout mechanism can operate without sequencing.

Multiplexed signal detection ensure that in multiplexed signal detection there is the ability to distinguish the amplification of many signals within the same volume as well as the ability to distinguish different signals from different volumes.

Binary Quantification/Digital Amplification

In some embodiments, the methods and assays described herein use digital and binary quantification methods; digital methods enable quantification of targets in samples containing low concentrations of cells (such as for example, when a sample (e.g. blood) has low concentrations of a pathogen (e.g. 1 bacterial cell per mL or 10 cells/mL) in a range that is still clinically relevant or even represent a life threatening illness). In some embodiments, the digital methods described herein can be used to ensure reliable quantification resolution between susceptible and resistant cells.

The process of binary quantification begins with a sample that can contain a target analyte. The target analyte can be a molecule to be quantified or searched for, for instance a particular nucleic acid, a particular nucleic acid sequence, a gene, or a protein, for example. The sample can be partitioned into many separate reaction volumes. In some embodiments, the reaction volumes are separate analysis regions. In some embodiments, the separate reaction volumes are physically separated in separate wells, chambers, areas on the surface of a slide, droplets, beads, or aliquots, for example. In some embodiments, the separate reaction volumes can be in the same container, for instance, the target analyte can be affixed to a substrate or attached to a bead. The reaction volumes can be on beads, on the surface of a slide, or attached to a substrate. The sample is distributed to many separate reaction volumes such that some, but not all of the reaction volumes generate a positive signal.

The sample is distributed to many separate reaction volumes such that each individual reaction volume contains a number of target analytes either below or above the threshold value for generating a positive signal. Generation of a positive signal from a reaction volume can depend on the number or concentration of target analytes captured, trapped, or bound by that reaction volume. In some cases, a threshold number of target analytes captured, trapped, or bound by a reaction volume allows a positive signal to be generated from that reaction volume. The threshold number of target analytes to allow positive signal generation can be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more target analytes. The threshold number of target analytes to allow positive signal generation can be at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 target analytes. In some cases, the threshold number of target analytes to allow positive signal generation can be from 1 to 19 target analytes. In some cases, the threshold number of target analytes to allow positive signal generation can be from 2 to 19 target analytes. In some cases, the threshold number of target analytes to allow positive signal generation can be from 3 to 19 target analytes. In some cases, the threshold number of target analytes to allow positive signal generation can be from 4 to 19 target analytes. In some cases, the threshold number of target analytes to allow positive signal generation can be from 5 to 19 target analytes. In some cases, the threshold number of target analytes to allow positive signal generation can be from 6 to 19 target analytes. In some cases, the threshold number of target analytes to allow positive signal generation can be from 7 to 19 target analytes. In some cases, the threshold number of target analytes to allow positive signal generation can be from 8 to 19 target analytes. In some cases, the threshold number of target analytes to allow positive signal generation can be from 9 to 19 target analytes. In some cases, the threshold number of target analytes to allow positive signal generation can be from 10 to 19 target analytes. In some cases, a threshold concentration of analytes captured, trapped, or bound by a reaction volume allows a positive signal to be generated from that reaction volume. The threshold concentration of target analytes to allow positive signal generation can be at least about zero zeptomolar (zM), 1 zM, 10 zM, 100 zM, 1 attomolar (aM), 10 aM, 100 aM, 1 femtomolar (fM), 10 fM, 100 fM, 1 pM, 10 pM, 100 pM, 1 nM, 10 nM, 100 nM, 1 µM, 10 µM, 100 µM, 1 mM, 10 mM, 100 mM, 1 M, or more. The threshold concentration of target analytes to allow positive signal generation can be at most about 1, fM, 10 fM, 100 fM, 1 pM, 10 pM, 100 pM, 1 nM, 10 nM, 100 nM, 1 µM, 10 µM, 100 µM, 1 mM, 10 mM, 100 mM, 1 M, or less. The threshold number or concentration of target analytes to allow positive signal generation from a reaction volume can be controlled. Inhibitors can be used with reaction volumes to control the threshold number or concentration. For example, the number or concentration of target analytes can be required to be higher than the number or concentration of inhibitors in a reaction volume in order for a signal to be produced from that reaction volume.

In some cases, the probability of a positive signal being generated from a reaction volume depends on the number or concentration of target analytes captured, trapped, or bound by that reaction volume. The probability of a positive signal being generated from a reaction volume can be controlled. For example, the efficiency of a signal generating reaction can be controlled, thereby controlling the probability of signal generation; a lower efficiency reaction can result in a lower probability of signal generation for a given number or concentration of target analytes.

In some embodiments, the sample is distributed to many separate reaction volumes such that each individual reaction volume contains either zero individual occurrences of the target analyte, or one or more individual occurrences of the target analyte. One or more molecules can mean a non-zero number of molecules. One or more molecules can mean one molecule. In some embodiments, one or more molecules can mean one molecule, two molecules, three molecules, four molecules . . . etc. In some embodiments, each separate reaction volume is contained in a well. In some embodiments, the sample is distributed such that each reaction volume, on average comprises less than one individual molecule of the target analyte. In some embodiments, the sample is distributed such that most reaction volumes comprise either zero or one molecules of the target analyte. Next, a qualitative "yes or no" test can be done to determine whether or not each reaction volume contains one or more target analytes by reading the pattern of discrete positive and negative reaction volumes. A positive reaction volume can be a reaction volume determined to contain one or more target analytes. A positive reaction volume can be a reaction volume determined to have a signal that correlates to the presence of one or more target analytes. A positive reaction volume can be a reaction volume determined to have a signal above a threshold that correlates to the presence of one or more target analyte. In some embodiments, a positive reaction volume is quantified as 1, or a simple multiple of 1 such as 2, 3, etc. while a negative reaction volume is quantified as 0, or less than a threshold. In some embodiments, a positive reaction volume is quantified as 1 and a negative reaction volume is quantified as 0. A negative reaction volume can be a reaction volume determined to contain zero target analyte. A negative reaction volume can be a reaction volume that does not have a signal that correlates to the presence of one or more target analyte. A negative reaction volume can be a reaction volume that does not have a signal above the threshold that correlates to the presence of one or more target analyte. The determination and/or designation of each reaction volume as a positive or a negative reaction volume can be referred to as a binary assay or a digital assay.

This "yes or no test" or test like this can be referred to as a binary assay. This qualitative analysis of which reaction volume are negative reaction volume and which reaction volume are positive reaction volume can then be translated into a quantitative concentration of target analyte in the sample using Poisson analysis. A high dynamic range can be achieved through using many reaction volumes. A high dynamic range can be achieved by using a device that has reaction volume of different sizes. A high dynamic range can be achieved by partitioning the sample into many wells and/or into wells of different sizes.

This overall process can be called binary quantification of nucleic acids. This process can be called counting numbers of target analyte. In some embodiments, binary quantification is the process of partitioning a sample into a plurality of reaction volume such that each reaction volume contains either zero or a non-zero number of target analyte; determining and/or designating which reaction volume are positive reaction volume and which reaction volume are negative reaction volume with respect to the target analyte; and translating the information about positive and negative reaction volume into information about the quantity or concentration of the target analyte in the sample. In some embodiments, the absolute number of target analyte is determined. In some embodiments, the translation of the information about which reaction volume are positive reaction volume and which reaction volume are negative reaction volume to information about the amount, absolute number of molecules, or concentration of the target analyte in the sample is called digital quantification of the target analyte. In some embodiments, the target analyte is a nucleic acid. In some embodiments, the binary quantification of nucleic acids is achieved. In some embodiments, binary quantification of a nucleic acid target analyte is determined wherein the sample is partitioned into several reaction volumes, wherein the reaction volumes are on a SlipChip.

In some embodiments, a binary quantification of target analyte in a sample can be achieved without spatially separating the sample into multiple reaction volumes. In these embodiments, the target analyte can be counted by informational separation. In some embodiments, target analyte in the sample undergo a binary quantification through a process wherein the target analyte are tagged with a pool of information-carrying molecules, amplified or copied, and the number of distinct information-carrying molecules that were amplified or copied is counted in to get a quantification of the starting number of target analyte (see e.g. WO 2012148477). In some embodiments, the information-carrying molecule can be a pool of chemical barcodes. In some embodiments, the information-carrying molecule can be a set of nucleic acid sequences.

Digital analyses can be achieved using the polymerase chain reaction (PCR), recombinant polymerase amplification (RPA), and loop mediated amplification (LAMP) as a way of quantifying RNA or DNA concentrations. Amplifications such as RPA and LAMP, which can use isothermal chemistries, can be well suited for home and limited-resource setting use. LAMP chemistry in particular is an attractive candidate for use in a home or limited-resource setting platform as it can have a relatively broad temperature tolerance range, can work with simple and cheap chemical-based heaters and phase-change materials, and can have a fluorescence gain with positive wells.

Robustness

Robustness can be the degree to which a series of repeated quantitative measurements provides a set of similar measurements under varying experimental conditions. For example a cell phone camera can be used to successfully perform similar measurements on a SlipChip under a variety of conditions found in the real world. Similar measurements can be identical measurements. Similar measurements can be the same diagnosis. Similar measurements can be the same answer. Similar measurements can mean more than one measurement within experimental error of each other. Similar measurements can yield a consistent outcome with statistical significance. Similar measurements can be of similar numerical size, for instance within 5%, 10%, 15%, 20%, 25%, 30%, 40%, 50%, 60%, 70%, 80%, 90%, 100%, 200%, 1,000% of each other. Robust assays can produce similar measurements more often than 25%, 30%, 40%, 50%, 60%, 70%, 80%, 85%, 90%, 95%, 96%, 97%, 98%, 99%, 99.5%, 99.9%, 99.99%, for example, of instances measured under a given set of conditions.

Different types of assays can be robust assays. A nucleic acid amplification and quantification assay can be robust. An assay to detect a protein or other target such as a cell, exosome, liposome, bacteria, virus, etc. can be robust. A LAMP assay can be robust. A RT-LAMP assay can be robust. A dRT-LAMP assay can be robust. A binary LAMP reaction can be robust. A binary, two-step LAMP reaction can be robust. A PCR reaction can be robust. A qPCR assay can be robust. A quantitative nucleic acid amplification reaction can be robust. A qualitative nucleic acid amplification reaction can be robust. A method to diagnosis a health outcome based on the amplification of a nucleic acid sequence can be robust. A process within a SlipChip can be robust. The imaging and analysis of a SlipChip after a LAMP reaction can be a robust process.

The absolute efficiency of dRT-LAMP can be increased over 10-fold, e.g. from ~2% to ~28%, by i) using a more efficient reverse transcriptase, ii) introducing RNase H to break up the DNA-RNA hybrid, and iii) adding only the BIP primer during the RT step. dRT-LAMP can be compatable with a plastic SlipChip device and used this two-step method to quantify HIV RNA. The dRT-LAMP quantification results were in some cases very sensitive to the sequence of the patient's HIV RNA.

Assays can be robust with respect to experimental variables. An assay can be robust with respect to a given temperature range. An assay can be robust of over a temperature range. Some non-limiting ranges, over which an assay can be robust include 1° C., 2° C., 3° C., 4° C., 5° C., 6° C., 7° C., 8° C., 9° C., 10° C., 11° C., 12° C., 16° C., 20° C., 24° C., 28° C., 32° C., 40° C., 50° C., 60° C., 80° C., 100° C., 150° C., 200° C., 250° C., or 300° C., for example. The temperature range of which an assay is robust can be centered on temperature on an absolute temperature scale. Some non-limiting temperatures that could be the center of the temperature range that an assay is robust to include −40° C., −30° C., −20° C., −10° C., 0° C., 10° C., 20° C., room temperature, 25° C., 30° C., 35° C., body temperature, 37° C., 40° C., 45° C., 50° C., 55° C., 60° C., 65° C., 70° C., 80° C., 90° C., 100° C., 110° C., 150° C., or 200° C., for example. In some embodiments, a binary LAMP assay is used to amplify and subsequently image and quantify a nucleic acid sequence in a sample. In these embodiments, the assay can be a robust quantification of a nucleic acid sequence with over a temperature range of 9° C. centered at about 60° C. A binary LAMP assay used to amplify and subsequently image and quantify a nucleic acid sequence in a sample can be robust over the temperature range from about 55° C. to about 66° C. In some embodiments, a SlipChip can be imaged and the data can be processed to give robust findings over a range of a temperature from about 5° C. to about 70° C.

An assay can be robust with respect to time. An assay can give consistent results over a range of time points. An assay can require only end-point readout. A binary DNA amplification experiment can require only end-point readout. The endpoint read out can be obtained near the completion of amplification, or at a time after this time point. A robust DNA amplification assay can give consistent results at a time point near the end of the reaction and/or at a timepoint after the reaction is complete. A non-limiting range of reaction time that an assay could be robust over includes 0.01 min, 0.1 min, 0.5 min, 1 min, 2 min, 3 min, 4 min, 5 min, 6 min, 7 min, 8 min, 9 min, 10 min, 12 min, 14 min, 16 min, 20 min, 24 min, 28 min, 32 min, 40 min, 45 min, 50 min, 1.0 hour, 2 hour, 3 hour, 4 hour, 5 hour, 6 hour, 8 hour, 10 hour, 12 hour, 16 hour, 18 hour, 1 day, 2 day, 3 day, 7 days, 1 month, or 1 year, for example. In some cases, binary DNA amplification experiments do not require exact knowledge of time. The output of a binary DNA amplification can be robust to variation in reaction time beyond the optimal reaction time. In some embodiments, a d-LAMP assay on a SlipChip is robust over a 20 minute time period between 40 minutes and 60 minutes after the LAMP reaction begins, for example.

An assay can be robust with respect to variations in atmospheric humidity. In some embodiments, an assay can be robust regardless of the atmospheric humidity. In some embodiments, an assay can be robust over a range of atmospheric humidity. The range of humidity can be from about 0% to 100% relative humidity. The range of atmospheric humidity at which an assay can be robust can be from about 0 to about 40 grams water per cubic meter of air at about 30° C. In some embodiments, an assay can be robust from about 0% humidity to about 40%, 50%, 60%, 70%, 80%, 90%, or 100% humidity, for example. In some embodiments, an assay can be robust over a humidity range of about 40%, 50%, 60%, 70%, 80%, 90%, or 100% humidity. In some embodiments, a d-LAMP assay run in a SlipChip can be imaged and analyzed as a robust assay over a range of humidity from about 0% to about 100% atmospheric humidity.

In some embodiments, the assay provides a quantitative analytical measurement. For instance, the invention can measure and display the amount and/or the concentration of a nucleic acid sequence within a sample as a quantitative amount. This measurement can be robust with respect to the experimental conditions present during the chemical amplification of the nucleic acid sequence, during the measurement of the optical data, and/or during the processing of the data, for instance.

In some embodiments, small differences in the concentration of a target can be resolved with greater statistical significance by quantifying the response of two or more genes to antibiotic treatment. For example, in a scenario in which two genes experience a 1.2-fold change in concentration when comparing samples treated with a drug versus samples that are untreated. If quantification yields this 1.2-fold difference with a p-value of around 0.10, then the difference will not be statistically significant when analyzed independently. However, using Fisher's method to combine the results from several independent tests that have the same overall null hypothesis (that the treated and untreated bacterial nucleic acids are the same) will result in a lower p-value than each individual test. The test statistic used to combine the p-values from separate tests is $\chi^2$ and the formula is $$\chi^2_{2k} = -2\sum_{i=1}^{k} \ln(p_i)$$

For example, if two independent tests with p-values of 0.10 each are combined using this method, the overall p-value will now be 0.05, which is significant at the 95% confidence level. In some embodiments, digital NA (nucleic acid) quantification is more amenable to POC diagnostics In some embodiments, a ratio of the RNA from multiple genes is used to determine drug susceptibility. In some embodiments, this approach can include the use of housekeeping genes to measure relative changes in gene expression. In some embodiments, this includes the use of a ratio between genes upregulated and genes downregulated in response to drug treatment. In some embodiments, ratios of genes are used to enable higher sensitivity of quantification of responses when few cells are present in the sample, in some embodiments as few as 1 cells.

Analysis

It is to be understood that the exemplary methods and systems described herein can be implemented in various forms of hardware, software, firmware, special purpose processors, or a combination thereof. These instructions and programs can be executed by and/or stored on non-transitory computer readable media. Methods herein can be implemented in software as an application program tangibly embodied on one or more program storage devices. The application program can be executed by any machine, device, or platform comprising suitable architecture. It is to be further understood that, because some of the systems and methods described herein are implemented in software, the actual connections between the system components (or the process steps) can differ depending upon the manner in which the present invention is programmed.

The number or concentration of target analytes in a sample can be calculated based on the signal generated from the reaction volumes. The number, location, type, or a combination thereof of positive reaction volumes can be used to calculate the number or concentration of target analytes in a sample. The number, location, type, or a combination thereof of positive capture regions can be used to calculate the number or concentration of target analytes in a sample.

Assay results can be determined by comparison of results to theoretical models. For example, Poisson statistical analysis can be applied to quantify the number of fluorescent and non-fluorescent regions. Combining the results from wells of different volumes fully minimizes the standard error and provides high-quality analysis across a very large dynamic range.

The computer components, software modules, functions, data stores and data structures described herein can be connected directly or indirectly to each other in order to allow the flow of data needed for their operations. It is also noted that the meaning of the term module includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality can be located on a single computer or distributed across multiple computers depending upon the situation at hand. In yet another aspect, a computer readable medium is provided including computer readable instructions, wherein the computer readable instructions instruct a processor to execute the methods described herein. The instructions can operate in a software runtime environment. In yet another aspect, a data signal is provided that can be transmitted using a network, wherein the data signal includes data calculated in a step of the methods described herein. The data signal can further include packetized data that is transmitted through wired or wireless networks. In an aspect, a computer readable medium comprises computer readable instructions, wherein the instructions when executed carry out a calculation of the probability of a medical condition in a patient based upon data obtained from the sample. The computer readable instructions can operate in a software runtime environment of the processor. In some embodiments, a software runtime environment provides commonly used functions and facilities required by the software package. Examples of a software runtime environment include, but are not limited to, computer operating systems, virtual machines or distributed operating systems although several other examples of runtime environment exist. The computer readable instructions can be packaged and marketed as a software product, app, or part of a software package. For example, the instructions can be packaged with an assay kit.

The computer readable medium can be a storage unit. Computer readable medium can also be any available media that can be accessed by a server, a processor, or a computer. The computer readable medium can be incorporated as part of the computer-based system, and can be employed for a computer-based assessment of a medical condition.

In some embodiment, the calculations described herein can be carried out on a computer system. The computer system can comprise any or all of the following: a processor, a storage unit, software, firmware, a network communication device, a display, a data input, and a data output. A computer system can be a server. A server can be a central server that communicates over a network to a plurality of input devices and/or a plurality of output devices. A server can comprise at least one storage unit, such as a hard drive or any other device for storing information to be accessed by a processor or external device, wherein the storage unit can comprise one or more databases. In an embodiment, a database can store hundreds to millions of data points corresponding to a data from hundreds to millions of samples. A storage unit can also store historical data read from an external database or as input by a user. In an embodiment, a storage unit stores data received from an input device that is communicating or has communicated with the server. A storage unit can comprise a plurality of databases. In an embodiment, each of a plurality of databases corresponds to each of a plurality of samples. An individual database can also comprise information for a plurality of possible sample containment units. Further, a computer system can comprise multiple servers. A processor can access data from a storage unit or from an input device to perform a calculation of an output from the data. A processor can execute software or computer readable instructions as provided by a user, or provided by the computer system or server. The processor can have a means for receiving patient data directly from an input device, a means of storing the subject data in a storage unit, and a means for processing data. The processor can also include a means for receiving instructions from a user or a user interface. The processor can have memory, such as random access memory. In one embodiment, an output that is in communication with the processor is provided. After performing a calculation, a processor can provide the output, such as from a calculation, back to, for example, the input device or storage unit, to another storage unit of the same or different computer system, or to an output device. Output from the processor can be displayed by data display. A data display can be a display screen (for example, a monitor or a screen on a digital device), a print-out, a data signal (for example, a packet), an alarm (for example, a flashing light or a sound), a graphical user interface (for example, a webpage), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In some embodiments, an output device is the same device as the input device. Example output devices include, but are not limited to, a telephone, a wireless telephone, a mobile phone, a PDA, a flash memory drive, a light source, a sound generator, a computer, a computer monitor, a printer, and a webpage. The user station can be in communication with a printer or a display monitor to output the information processed by the server.

A client-server, relational database architecture can be used in embodiments of the invention. A client server architecture is a network architecture in which each computer or process on the network is either a client or a server. Server computers are typically powerful computers dedicated to managing disk drives (file servers), printers (print servers), or network traffic (network servers). Client computers include PCs (personal computers), cell phones, or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

Subject data can be stored with a unique identifier for recognition by a processor or a user. In another step, the processor or user can conduct a search of stored data by selecting at least one criterion for particular patient data. The particular patient data can then be retrieved. Processors in the computer systems can perform calculations comparing the input data to historical data from databases available to the computer systems. The computer systems can then store the output from the calculations in a database and/or communicate the output over a network to an output device, such as a webpage, a text, or an email. After a user has received an output from the computer system, the user can take a course of medical action according to the output. For example, if the user is a physician and the output is a probability of cancer above a threshold value, the physician can then perform or order a biopsy of the suspected tissue. A set of users can use a web browser to enter data from a biomarker assay into a graphical user interface of a webpage. The webpage is a graphical user interface associated with a front end server, wherein the front end server can communicate with the user's input device (for example, a computer) and a back end server. The front end server can either comprise or be in communication with a storage device that has a front-end database capable of storing any type of data, for example user account information, user input, and reports to be output to a user. Data from each user can be then be sent to a back end server capable of manipulating the data to generate a result. For example, the back end server can calculate a corrections for similar cell phones or compile data generated from similar sample collection units. The back end server can then send the result of the manipulation or calculation back to the front end server where it can be stored in a database or can be used to generate a report. The results can be transmitted from the front end server to an output device (for example, a computer with a web browser or a cell phone) to be delivered to a user. A different user can input the data and receive the data. In an embodiment, results are delivered in a report. In another embodiment, results are delivered directly to an output device that can alert a user.

The information from the assay can be quantitative and sent to a computer system of the invention. The information can also be qualitative, such as observing patterns or fluorescence, which can be translated into a quantitative measure by a user or automatically by a reader or computer system. In an embodiment, the subject can also provide information other than sample assay information to a computer system, such as race, height, weight, age, gender, eye color, hair color, family medical history, identity, location and any other information that can be useful to the user.

In some embodiments additional information is provided by sensors associated with the device. For example global positioning data, acceleration data, air pressure, or moisture levels can be measured by a device comprising the image sensor. This additional information can be used by the computer systems of the invention.

Information can be sent to a computer system automatically by a device that reads or provides the data from image sensor. In another embodiment, information is entered by a user (for example, the subject or medical professional) into a computer system using an input device. The input device can be a personal computer, a mobile phone or other wireless device, or can be the graphical user interface of a webpage. For example, a webpage programmed in JAVA can comprise different input boxes to which text can be added by a user, wherein the string input by the user is then sent to a computer system for processing. The subject can input data in a variety of ways, or using a variety of devices. Data can be automatically obtained and input into a computer from another computer or data entry system. Another method of inputting data to a database is using an input device such as a keyboard, touch screen, trackball, or a mouse for directly entering data into a database.

In an embodiment, a computer system comprises a storage unit, a processor, and a network communication unit. For example, the computer system can be a personal computer, laptop computer, or a plurality of computers. The computer system can also be a server or a plurality of servers. Computer readable instructions, such as software or firmware, can be stored on a storage unit of the computer system. A storage unit can also comprise at least one database for storing and organizing information received and generated by the computer system. In an embodiment, a database comprises historical data, wherein the historical data can be automatically populated from another database or entered by a user.

In an embodiment, a processor of the computer system accesses at least one of the databases or receives information directly from an input device as a source of information to be processed. The processor can perform a calculation on the information source, for example, performing dynamic screening or a probability calculation method. After the calculation the processor can transmit the results to a database or directly to an output device. A database for receiving results can be the same as the input database or the historical database. An output device can communicate over a network with a computer system of the invention. The output device can be any device capable delivering processed results to a user.

Communication between devices or computer systems of the invention can be any method of digital communication including, for example, over the internet. Network communication can be wireless, ethernet-based, fiber optic, or through fire-wire, USB, or any other connection capable of communication. In an embodiment, information transmitted by a system or method of the invention can be encrypted.

It is further noted that the systems and methods can include data signals conveyed via networks (for example, local area network, wide area network, internet), fiber optic medium, carrier waves, wireless networks for communication with one or more data processing or storage devices. The data signals can carry any or all of the data disclosed herein that is provided to or from a device.

Additionally, the methods and systems described herein can be implemented on many different types of processing devices by program code comprising program instructions that are executable by the device processing subsystem. The software program instructions can include source code, object code, machine code, or any other stored data that is operable to cause a processing system to perform methods described herein. Other implementations can also be used, however, such as firmware or even appropriately designed hardware configured to carry out the methods and systems described herein.

A computer system can be physically separate from the instrument used to obtain values from the subject. In an embodiment, a graphical user interface also can be remote from the computer system, for example, part of a wireless device in communication with the network. In another embodiment, the computer and the instrument are the same device.

An output device or input device of a computer system can include one or more user devices comprising a graphical user interface comprising interface elements such as buttons, pull down menus, scroll bars, fields for entering text, and the like as are routinely found in graphical user interfaces known in the art. Requests entered on a user interface are transmitted to an application program in the system (such as a Web application). In one embodiment, a user of user device in the system is able to directly access data using an HTML interface provided by Web browsers and Web server of the system.

A graphical user interface can be generated by a graphical user interface code as part of die operating system or server and can be used to input data and/or to display input data. The result of processed data can be displayed in the interface or a different interface, printed on a printer in communication with the system, saved in a memory device, and/or transmitted over a network. A user interface can refer to graphical, textual, or auditory information presented to a user and can also refer to the control sequences used for controlling a program or device, such as keystrokes, movements, or selections. In another example, a user interface can be a touch screen, monitor, keyboard, mouse, or any other item that allows a user to interact with a system of the invention.

Use of Antibiotic Susceptibility Data

In yet another aspect, a method of taking a course of medical action by a user is provided including initiating a course of medical action based on sample analysis. The course of medical action can be delivering medical treatment to said subject. The medical treatment can be selected from a group consisting of the following: a pharmaceutical, surgery, organ resection, and radiation therapy. The pharmaceutical can include, for example, a chemotherapeutic compound for cancer therapy. The course of medical action can include, for example, administration of medical tests, medical imaging of said subject, setting a specific time for delivering medical treatment, a biopsy, and a consultation with a medical professional. The course of medical action can include, for example, repeating a method described above. A method can further include diagnosing the medical condition of the subject by said user with said sample. A system or method can involve delivering a medical treatment or initiating a course of medical action. If a disease has been assessed or diagnosed by a method or system of the invention, a medical professional can evaluate the assessment or diagnosis and deliver a medical treatment according to his evaluation. Medical treatments can be any method or product meant to treat a disease or symptoms of the disease. In an embodiment, a system or method initiates a course of medical action. A course of medical action is often determined by a medical professional evaluating the results from a processor of a computer system of the invention. For example, a medical professional can receive output information that informs him that a subject has a 97% probability of having a particular medical condition. Based on this probability, the medical professional can choose the most appropriate course of medical action, such as biopsy, surgery, medical treatment, or no action. In an embodiment, a computer system of the invention can store a plurality of examples of courses of medical action in a database, wherein processed results can trigger the delivery of one or a plurality of the example courses of action to be output to a user. In an embodiment, a computer system outputs information and an example course of medical action. In another embodiment, the computer system can initiate an appropriate course of medical action. For example, based on the processed results, the computer system can communicate to a device that can deliver a pharmaceutical to a subject. In another example, the computer system can contact emergency personnel or a medical professional based on the results of the processing. Courses of medical action a patient can take include self-administering a drug, applying an ointment, altering work schedule, altering sleep schedule, resting, altering diet, removing a dressing, or scheduling an appointment and/or visiting a medical professional. A medical professional can be for example a physician, emergency medical personnel, a pharmacist, psychiatrist, psychologist, chiropractor, acupuncturist, dermatologist, urologist, proctologist, podiatrist, oncologist, gynecologist, neurologist, pathologist, pediatrician, radiologist, a dentist, endocrinologist, gastroenterologist, hematologist, nephrologist, ophthalmologist, physical therapist, nutritionist, physical therapist, or a surgeon.

Once the number of positive wells or reaction chambers has been determined, that number is processed using Poisson statistics and prior knowledge about the chip in question to determine the original concentration of sample in the chip. This information is then automatically sent via email to any valid email account and is then received by the original person who took the image regardless of where they are in the world relative to the computer that performs the image analysis. The time that elapses between the taking of the image and the receipt of email confirmation has been performed in well under 1 minute, although actual time is subject to the upload speed on the network of the cell phone and download speed on the network of the computer. This is important, because if an error is detected in the course of an analysis, such as not being able to find all 4 spots, the user needs to be quickly alerted that another image must be taken. The software has been programmed to do such, and the user typically knows in under 1 minute to take another image. Having the ability to notify by email can give the ability to notify via text. Cell phone providers can have a service that will send the body of an email as a text to specific users. Other servers that can be leveraged as SMS messengers. The analysis process can use computer automation to notify a user if the image can be used. The notification can be an SMS message, email message, phone call, web posting, or electronic message for example. In some embodiments, the amount of time from the uploading of the image until the user is notified can be referred to as the analysis process. The analysis process can take less than 5 min, 4 min, 3 min, 2 min, 1 min, 50 sec, 45 sec, 40 sec, 30 sec, 20 sec, 10 sec, 9 sec, 8 sec, 7 sec, 6 sec, 5 sec, 4 sec, 3 sec, 2 sec, 1 sec, 0.5 sec, 0.4 sec, 0.3 sec, 0.2 sec, or 0.1 sec, for example. In some embodiments, the analysis process takes less than 1 min.

At least one calibration source for providing a calibration emission, and at least one calibration photodiode for sensing the calibration emission wherein the control circuitry has a differential circuit for subtracting the calibration photodiode output from each of the detection photodiode outputs can be provided in some embodiments.

A communication interface can be a universal serial bus (USB) connection such that the outer casing is configured as a USB drive.

In some instances the information is transmitted back to the mobile device which was used for imaging. For example an image can be obtained, send to a separate computer for analysis, and then the image or date related to the image can be transmitted back to the mobile device. In some embodiments an image and/or a processed image and/or resulting data the user is transmitted to a separate device, e.g. a physician's mobile device can receive the information. In some instances two or sets of information are transmitted to two or more devices. The two or more sets of information can be the same information, or in some embodiments, separate data is sent to each user. For example a patient can receive some information related to an image while the patient's doctor receives information more suitable for a physician's analysis.

While offloading the analysis of images to "the cloud" provides a number of benefits, including traceability and archiving of raw data, global access, and compatibility with virtually all smartphone operating systems, it requires a wireless data connection of sufficiently high bandwidth; thus, direct on-phone analysis could be preferable in some scenarios.

Platforms/Devices

Provided herein are devices (e.g., microfluidic devices) and methods that can rapidly identify a cell, including a cancer cell, or microorganism, including a pathogen, quantify their load, and diagnose their susceptibility or resistance to drugs, such as antibiotics. In some embodiments the devices can enable phenotypic detection and metabolic profiling of drug susceptibility or drug resistance using individual microorganisms or cells which can originate from various sample types, including clinical or environmental samples. These sample types can include, but are not limited to, blood, cerebral spinal fluid (CSF), saliva and urine and can also include environmental samples, such as from water or a hospital surface. In some embodiments, the devices enable incubation of cells with drugs, such as antibiotics, and then rapidly extract and quantify nucleic acids or other molecules in a contamination-free platform. The devices can use digital single-molecule measurements in microfluidics devices, which provide ultra-sensitive measurements that improve detection limits while providing quantitative data, important for differentiating pathogens from contaminants and enabling earlier differentiation between drug-resistant and susceptible organisms or cells. In some embodiments, these devices can differentiate the state of individual microorganisms or cells from a clinical sample, and understand the timing of their individual responses to drugs, such as for example antibiotics, providing ultra-fast drug-susceptibility measurements.

In some embodiments the devices and methods can be used in assessing gene duplications measurements for each given cells, as in response to antibiotic stress some microbes can replicate antibiotic resistant genes (like lactamases) to 100 s of copies, allowing them to undergo evolution.

In some embodiments, the devices and methods allow identification of drug-resistant bacteria from a pool of bacteria, such as a clinical sample, that can include drug-susceptible bacteria and/or drug-resistant bacteria and/or contamination with pathogenic and/or nonpathogenic bacteria—or some combination of these types. In some embodiments the devices can be used to incubate cells with drugs and then rapidly extract and quantify nucleic acids, such as for example RNA, in a contamination-free platform to determine drug susceptibility. In some embodiments, the methods and devices provided herein enable microbial and cell identification and drug susceptibility testing outside of CLIA clinical laboratories Devices can comprise channels and flowpaths, such as microfluidic channels. Devices can comprise inlets, outlets, or any combination thereof. Devices can comprise wells, reservoirs, or any combination thereof. Devices can comprise reaction volumes. Devices can comprise preloaded reagents. In some cases, the microfluidic device comprises a SlipChip device, as described for example in U.S. patent application Ser. No. 13/257,811, in PCT Application No. PCT/US2010/028361, in US Patent Publication No. 20120329038 A1, and in International Patent Publication No. WO 2013072069 A1, each of which is hereby incorporated by reference in its entirety. In some embodiments, the samples are contacted with a reagent for performing a reaction. As used herein, "contacting" refers to introducing a substance or maintaining a substance in an area or in a solution comprising the entity the substance is to be contacted to. For example, contacting a region for the amplification of a target nucleic acid with a reagent for performing the reaction can include flowing the reagent into the chamber, either separately or already together with the target nucleic acid, or having the reagent already preloaded into the region for amplification. Contacting can occurs when two substances are interacting under conditions to bind, touch, facilitate a reaction, or otherwise maintain proximity under desired conditions.

Platforms can comprise fluid handling mechanisms enabling loading, unloading, mixing, and other handling of sample volumes, reagent volumes, and other fluids. For example, a microfluidic device can be used comprising channels for loading fluids into wells or droplets, for mixing contents of wells or droplets, or for off-loading of contents of wells or droplets.

Some platforms are useful for conducting assays in a digital or quasi-digital format, as described herein. For example, wells, well plates, microwells, microfluidic droplets, emulsions, beads, and microarrays can provide a useful platform for conducting a digital or quasi-digital assay. In such an assay, the compartments can comprise individual wells, droplets, beads, or microarray spots.

In some embodiments, devices described herein incorporate SlipChip digital amplification technology and SlipChip sample preparation technology (Shen, et al., 2010, Analytical Chemistry, 4606-4612, Shen, et al., 2010, Lab on a Chip, 2666-2672, Shen, et al., 2011, Analytical Chemistry, 3533-3540, Shen, et al., 2011, J Am Chem Soc, 17705-47712) and can perform rapid single-molecule identification, and quantification of nucleic acids from cells and microorganisms, such as for example *Klebsiella pneumonia, Pseudomonas aeruginosa*, and extra-intestinal pathogenic *E. coli*. Samples can be obtained from a variety of human bodily fluids, such as for example blood, plasma, saliva, CSF or urine, or a variety of environmental samples, such as for example water or hospital surfaces. In some embodiments, this can enable clinical validation of workflow that in some embodiments provides a differential diagnosis of an infection, such as for example a UTI. In some embodiments, this device can provide quantification of total cell load and species and/or strain identification. In some embodiments, the results of the assay can be available in less than 45 minutes, less than 30 minutes, less than 20 minutes, less than 10 minutes, less than 5 minutes, less than 3 minutes, or less than 1 minute.

In some embodiments, the technology described here enables identification and quantification of nucleic acids, such as for example bacterial DNA and RNA extracted from urine samples spiked with a cell culture of reference strains. Reference strains are those are used routinely in clinical labs as part of their quality control protocol, such as for example *K. pneumoniae* (ATCC 700603), *P. aeruginosa* (ATCC 27853), and *E. coli* (ATCC 25922). (Institute., 2012, M07-A09) In some embodiments the technology and devices described in this disclosure can be integrated with standard bench methods and kits (Qiagen Qiamp DNA kit) to extract nucleic acids, and previously published universal primers can be used to target genes, such as for example the conserved region of the 16S gene, in order to quantify nucleic acid concentration (Clifford, et al., 2012, PLoS ONE, e48558, Nadkarni, et al., 2002, Microbiology, 257-266). For example, the technology can be used to target hyper-variable regions of the 16S gene to quantify and identify microorganisms (Baker, et al., 2003, Journal of Microbiological Methods, 541-555, Hansen, et al., 2013, PLoS ONE, e61439, Spilker, et al., 2004, Journal of Clinical Microbiology, 2074-2079).

In some embodiments, the devices described herein allow identification of drug-resistant bacteria from a pool of bacteria, such as a clinical sample, that can include drug-susceptible bacteria and/or drug-resistant bacteria and/or contamination with pathogenic and/or nonpathogenic bacteria, or any combination thereof.

In some embodiments, the technology can be used for bacterial DNA and RNA amplification assays using the digital SlipChip over a dynamic range of, for example, 1,000 to $1 \times 10^7$ copies/mL with, for example, three-fold resolution and a 95% confidence interval. This dynamic range is well covered by the digital SlipChip that is commercially manufactured, which contains 10,240 of 0.84 nL wells with a dynamic range of 450 to $9.7 \times 10^7$ copies/mL and a detection limit of 120 copies/mL.

Figure 5:
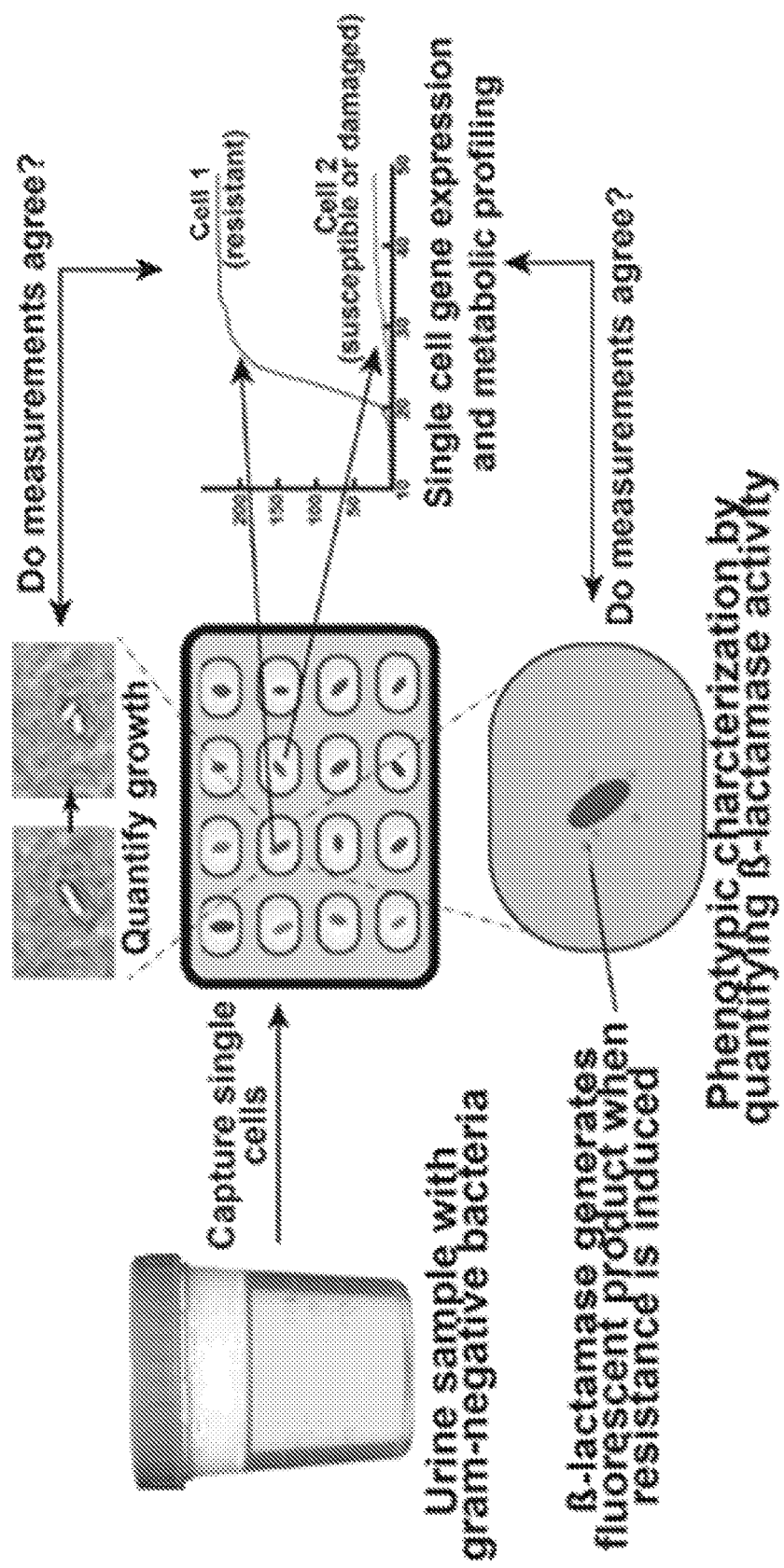
FIG. 5 depicts workflow of determining the resistance or susceptibility of a cell in a sample of urine to a drug according to an embodiment of the invention.

A workflow of determining the resistance or susceptibility of a cell in a sample of urine to a drug according to an embodiment of the invention is shown in FIG. 5. In some embodiments, the device enables assays that perform both sample prep (e.g., exposure of organism in the sample to a drug and extraction of target nucleic acids from the sample) and digital amplification (e.g., distributing and amplifying target nucleic acids to quantify the target nucleic acids present in the sample to determine a susceptibility or resistance of the organism to the drug).

Integrated Devices

Figure 6A:
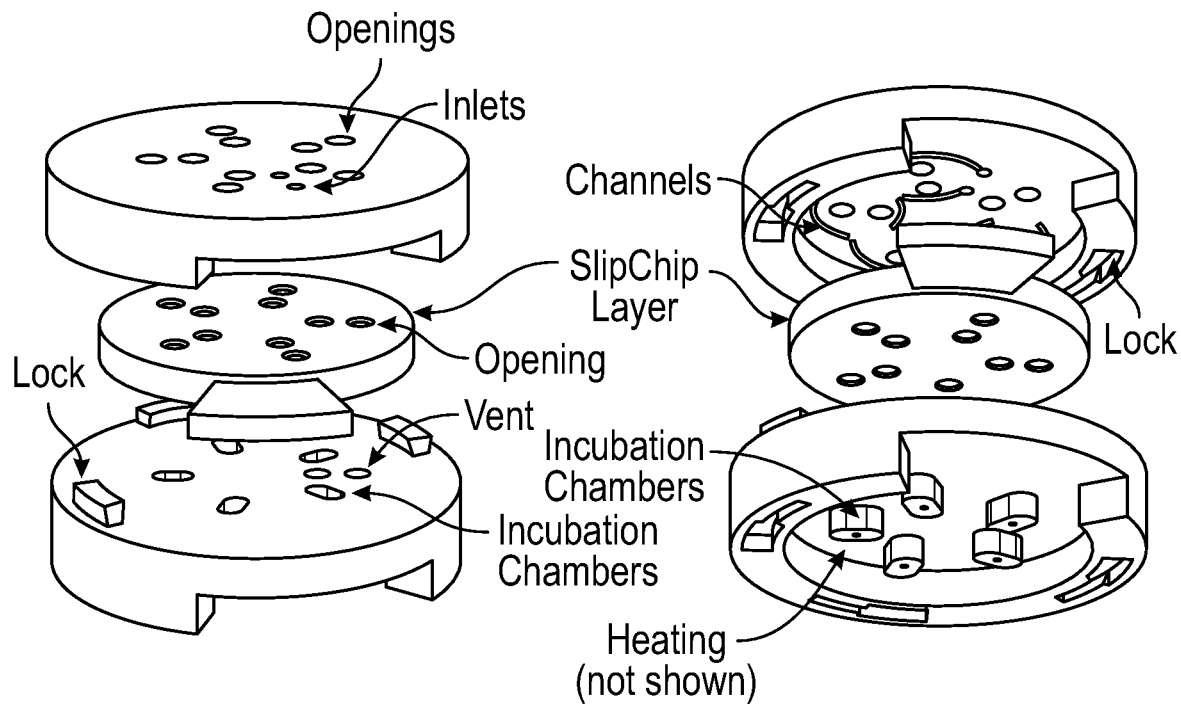
Figure 6B:
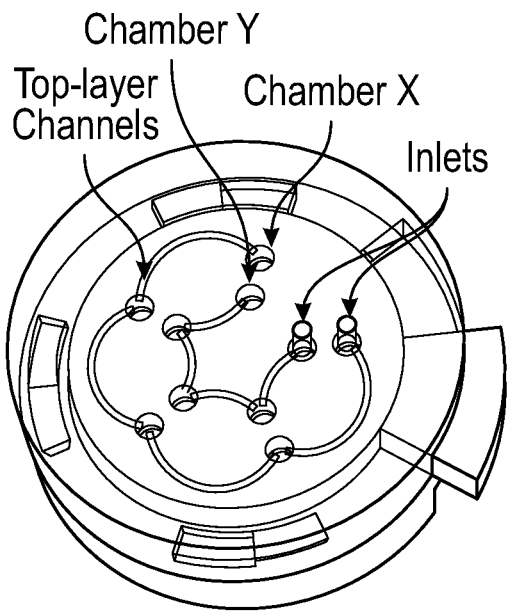
Figure 6B:
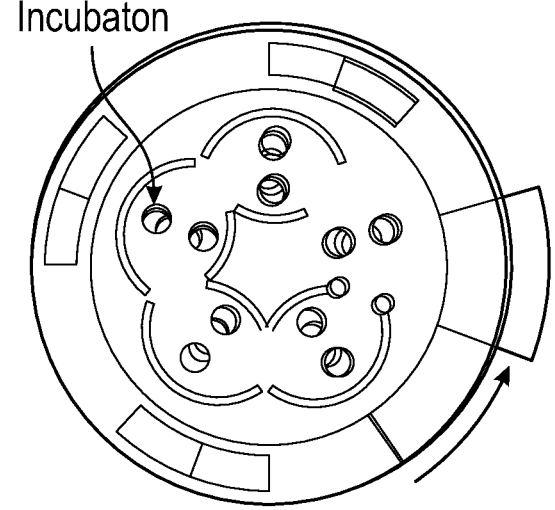

In some embodiments, the devices provided herein are integrated devices comprising one or more modules. These modules include, but are not limited to, an incubation module, a sample preparation module, an amplification module, and a readout module. Each of these modules is described herein. In some embodiments, the integrated device combines 2 or more modules to provide a simplified processing flow for detecting the properties of an organism in a cell in response to a drug. An example of an integrated device comprising an incubation chamber and devices to regulate flow of the sample into the incubation chamber is depicted in FIGS. 6A, 6B, and 6C.

Incubation Module

In some embodiments, the integrated device comprises an incubation module. The incubation module can contain an incubation chamber for, e.g., exposing a microorganism to a drug (see FIGS. 6A, 6B, and 6C). In some embodiments, the incubation module contains inlets allowing for the inserting of fluids, such as sample, media, reagents, or other solutions. These solutions are pushed into the SlipChip-like device through some means, an example being positive pressure from a pumping lid or plunger as shown in FIG. 6C. In some embodiments, the layer adjacent to the SlipChip layer contains channels through which the sample can flow. In some embodiments, the uppermost layer has one or more openings for venting and controlling pressures. In some embodiments, the openings of the SlipChip layer are filled with solution, splitting the sample into different volumes. This layer is then slipped, the openings of the SlipChip layer are moved to form a connection with a separate layer, for example an opening to incubation chambers. The samples can be transported from the central SlipChip layer and mixed with solution, such as media or antibiotics, contained within the incubation chambers. In some embodiments, the incubation chambers can be sitting in a heated bath or otherwise in contact with heating elements for incubation. In some embodiments, membranes such as hydrophobic films are used for venting. In some embodiments, one or more openings are present in one or more layers of the device for controlling pressures. In some embodiments, the layer containing the incubation chamber can also be slipped. In some embodiments, fluids from the incubation chambers are transported to a separate module, such as the amplification module. In some embodiments, one or more SlipChip layers are used, for example, below the incubation chambers with openings to the sample prep or other module. In some embodiments, the integrated device has additional incubation modules.

In some embodiments, the incubation chamber in the incubation module is used for antibiotic susceptibility testing. In some embodiments, cells are pre-sorted through a filter. In some embodiments, a filter is used to capture bacterial cells. In some embodiments, mammalian cells are lysed selectively without lysing bacterial cells of interest. In some embodiments, selective lysis and filtration steps are combined. In some embodiments, the incubation chamber comprises an array of sub-chambers for confinement of cells.

In some embodiments, the incubation chamber is a module configured to perform one or more of the following: (i) partitioning the sample, (ii) partitioning the drug/antibiotic, (iii) combining the sample with the drug/antibiotic, (iv) mixing, (v) incubating the sample, or (vi) transporting the fluids to a separate chamber.

In some embodiments, digital assays can use the confinement of cells from a sample into an incubation chamber or a clonal isolation regions. In some embodiments, the isolated cells are cultured in individual incubation chamber to generate a plurality of clonal populations from the sample. In some embodiments, the isolated cells are treated with a drug before or after expansion. In some embodiments, after culture and expansion from an isolated cell, the clonal population is divided into two or more treatment regions. As such, at least one portion of the clonal population can be treated with a drug, while another portion of the clonal population is not treated with a drug. Then, the assays described herein can be performed to determine whether the cells in the clonal population are susceptible or resistant to one or more drugs.

In some embodiments, splitting is performed through a SlipChip design utilizing dead-end filling. In some embodiments, to achieve dead-end channel filling with an aqueous solution, a hydrophobic membrane can be used at the end of the channel which blocks the flow of aqueous solution but allows non-aqueous liquid and gas to flow through.

In some embodiments, slipping (i.e., movement of the layers) can be actuated automatically using a rotating shaft. In some embodiments, this shaft can be controlled by a motor, optionally encoded or programmed to specific speeds, directions, and/or rotation angles.

In some embodiments, combination and mixing of the sample with the drug/antibiotic is performed by pressurization of a chamber which transports one or more of the solutions into the other solution. In some embodiments, pressurization of chambers is generated by a pumping lid which creates a seal and changes the volume in that compartment; this can be actuated manually or through a rotating shaft, among other actuations. In some embodiments, transport of fluids into or out of the growth chamber module can be performed by pressurization of the chamber, such as for example by a pumping lid (either manually or automatically), the opening of a valve, or by other methods, such as e.g. pipetting.

In some embodiments, the incubation chamber module contains a heating element. Some examples of heating element control include a circuit board with a means to control the temperature and timing or phase change material In some embodiments, the incubation chamber is designed to process between 1 mL and 10 mL. In some embodiments, the incubation chamber is designed to process between 100 µL and 3 mL. In some embodiments, the incubation chamber is designed to process between 10 µL and 100 mL. In some embodiments, the incubation chamber is designed to process samples likely containing single cells.

Sample Preparation Module

In some embodiments, the device comprises a sample preparation module. In some embodiments, samples can be split into different compartments that may or may not contain a drug of interest (such as an antibiotic). In some embodiments, after incubation of the sample with/without antibiotic drug, the cells of interest (such as for example those of a bacterial pathogen) are lysed (such as by lysis buffer) in order to extract RNA and/or DNA. In some embodiments, the sample-preparation module can be used to automatically extract nucleic acids from urine. In some embodiments, for sample preparation, a filter column can be used to capture RNA/DNA from a lysed sample and wash away cell debris or other components present in the lysed sample.

In some embodiments, an automated or semi-automated sample preparation module is provided. In some embodiments, the automated or semi-automated sample preparation module generates pressure to the lysed sample in a sealed environment, forcing the lysed sample through a filter column (e.g., a nucleic acid-binding column, such as a glass fiber column).

In some embodiments, the sample prep module is designed to process between 1 mL and 10 mL. In some embodiments, the sample prep module is designed to process between 100 μL and 100 mL. In some embodiments, the sample prep module is designed to process between 10 μL and 1 L. In some embodiments, the sample prep module is designed to process between 1 μL and 1 mL. In some embodiments, the sample preparation module can be made of plastic and in some embodiments does not require external power or active user intervention.

Digital Quantification Module

In some embodiments, devices contain digital (or binary) quantification modules, such as modules containing multiple detection elements in which 0, 1, or more target (e.g. RNA/DNA) molecules are captured per each detection element and are suitable for integration.

In some embodiments, enriched target (e.g. DNA/RNA) are recovered from the device for use in subsequent or parallel experiments. In some embodiments, the integrated device has a plurality of quantification modules.

In some embodiments, the quantification module is designed to process between 30 μL and 60 μL. In some embodiments, the quantification module is designed to process between 1 μL and 100 μL. In some embodiments, the quantification module is designed to process between 100 nL and 1 mL. In some embodiments, the quantification module is designed to process between 10 nL and 10 mL.

Reagent Storage

Figure 7:
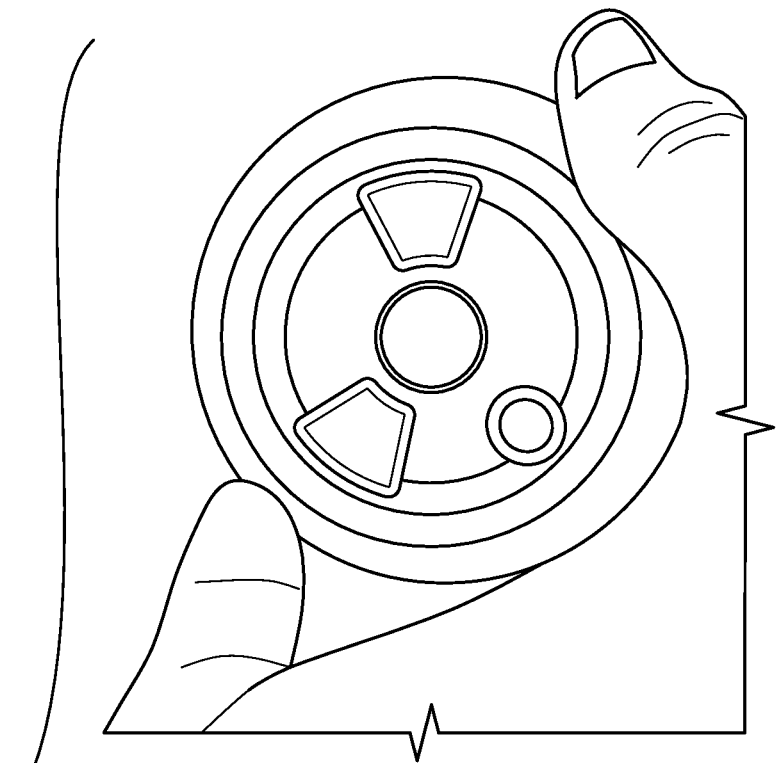
FIG. 7 shows a photograph of blister packs, reagent packs, or other types of containers to be used with the integrated device, according to an embodiment of the invention.
Figure 7:
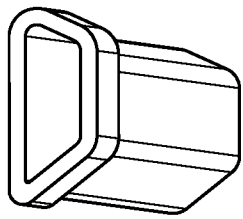
Figure 7:
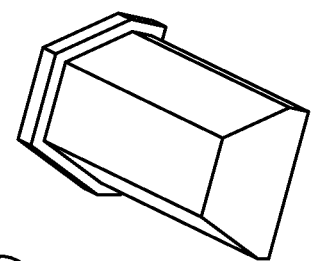
Figure 7:
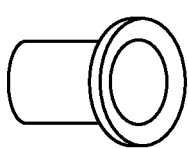

In some embodiments, the integrated device comprises stored reagents. In some embodiments, the liquids in the devices (including those described above) can be stored, such as in blister packs, reagent packs, or other types of containers in which they are sealed (FIG. 7).

In some embodiments, the device comprises a reagent pack suitable for preparing nucleic acid of the cell or microorganism for nucleic acid quantification reaction. In some embodiments, the device comprises a reagent pack suitable for nucleic acid quantification reaction. In some embodiments, the reagent pack comprises enzymes for performing a nucleic acid quantification reaction. In some embodiments, the reagent pack comprises primers for performing a nucleic acid quantification (e.g., for PCR or isothermal amplification)

Exemplary reagents in the reagent pack can include, but are not limited to, lysis solutions, wash solutions, elution solutions, rehydration solutions, enzyme solutions (e.g., nucleic acid amplification enzymes, polymerase enzymes, restriction enzymes), buffers, liquid, powder, pellets, a gel, microbeads, probes, primers, nucleic acids, DNA, RNA, polypeptides, nucleoside triphosphates (NTPs), antibodies, a sacrificial reagent or any combination thereof. A sacrificial reagent can comprise an aqueous solution, a lubricant, an oil, an aqueous-immiscible liquid, a gel, a gas, a fluorocarbon oil, a surfactant, gas, air, or any combination thereof. For example, the air can be used to generate air bubble for mixing. As another example, air and immiscible liquid can be used to remove leftover solution (dead volume) in the matrix. Reagents can be mixed to change their composition. For example, one type of buffer can be mixed with another buffer or a dry reagent to change its composition to another buffer.

In some embodiments, the device comprises a reagent pack for assaying enzyme presence and/or activity, such as, for example, monobromobimane, 7-Diethylamino-3-(4'-Maleimidylphenyl)-4-Methylcoumarin, N-(7-Dimethylamino-4-Methylcoumarin-3-yl))Maleimide), NiWa blue (1-Benzyl 4-methyl 5-(tert-butoxycarbonylamino)-2-(2,5-dioxo-2,5-dihydropyrrol-1-yl)terephthalate), NiWa Blue II (Dimethyl 5-acetamido-2-(2,5-dioxo-2,5-dihydropyrrol-1-yl)terephthalate), NiWa orange (Dimethyl 2-amino-5-((2,5-dioxo-2,5-dihydro-1H-prrol-'-yl)ethyl)amino)terephthalate), Ellman's reagent/DTNB (5,5'-dithiobis-(2-nitrobenzoic acid)), Umbelliferone-derived cephalosporins, Fluorescein-derived cephalosporins, Resorufin-derived cephalosporins, Rhodamine-derived cephalosporins, Imipenem, and p-nitrophenol releasing substrates In some embodiments, the device comprises a reagent pack containing one or more drugs at one or more concentration. In some embodiments, the device comprises a reagent pack containing one or more antibiotics at one or more concentration. In some embodiments, the device comprises a reagent pack containing components suitable for accelerating response of a cell or microorganism to a drug (e.g. quorum sensing molecules, etc.). In some embodiments, the device comprises a reagent pack containing culture media to enhance cell growth.

In some embodiments, the device comprises a reagent pack containing gases or gas mixtures, containing $H_2S$, CO, and NO. Such gases are known, for example, to affect susceptibility of microorganisms to antibiotics. Such gases can be diluted with a gas mixture which could be anaerobic, aerobic, or microoxic. Such gas mixture can contain $CO_2$. In some embodiments, the device comprises a reagent pack containing lysis reagents to expose intercellular components.

In some embodiments, these containers avoid evaporation of solutions. In some embodiments, reagents can be released from one or more container by piercing certain regions of the containers, or by selectively opening parts of the containers at the appropriate times. In some embodiments, the generated pressure in the device can release the contents of the blisters/containers; in some embodiments these fluids are transported to other parts of the device. In some embodiments, reagents (such as e.g. amplification reagents) are stored as dried reagents, on device, in blister packs, or in containers (or some combination thereof). The reagents can be lyophilized, stored with sugars (e.g. sucrose, trehalose, among others), and/or stored with beads.

Operation Module

In some embodiments, the device contains an operation module, such as for example a module to operate devices (including integrated devices). In some embodiments, an operation module can perform one or more of the following functions: motor control, shaft rotation, heating, image capture, and image processing. In some embodiments, an operation module can use one or more motors and shafts. In some embodiments, an operation module can use one or more rotary valves.

Figure 8:
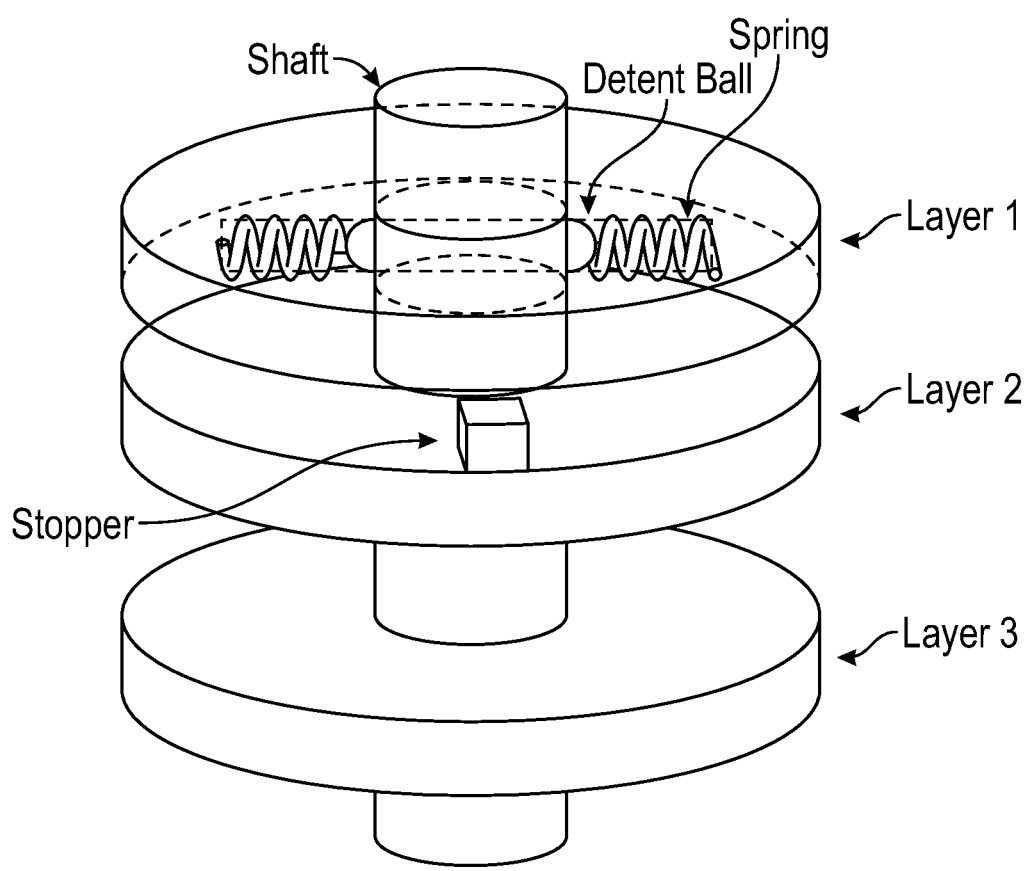
FIG. 8 is a diagram of an operation module with one or more layers to be driven by a spring or motor, according to an embodiment of the invention.

In some embodiments, an operation module consists of one or multiple components, of which one or multiple components can be driven/rotated by a spring or motor (FIG. 8). In some embodiments, a spring or motor can be used to rotate a threaded part, which can be connected to a separate lid/plunger with the inverse thread of the former part (as described in pumping lid patent application). In some embodiments, as the spring or motor rotates the first threaded part, the plunger/lid can move and change the volume and pressure present in one or more cavities. In some embodiments, the lid/plunger forms a hermetic seal within one or more cavities. In some embodiments, the generated pressure can be used to flow a liquid sample that is present in the cavity through a filter column.

Fluid Management

In some embodiments, the device is configured to transport a volume of lysed samples out of device for a separate or parallel experiment. In some embodiments, valves for generating pressure to control the flow of solutions through the device (such as in which different solutions are flowed through the column or temporarily prevented from flowing through the column) are incorporated into the device. In some embodiments, negative pressures are utilized during device operation. In some embodiments, chambers within the device can be pressurized or depressurized prior to the initiation of the device.

In some embodiments, a one-step or multistep process can be controlled, such as by placing a filter column in the rotating layer of the device. In some embodiments, as the filter column is rotated in the device, the sample can be moved to different chambers in the device that can contain different reagents; these fluids can flow sequentially or nonsequentially through the filter column. In some embodiments, the liquid present in one or more chambers will be moved (such as via the generated pressure of a pumping lid) and a solution will flow through the filter column. In some embodiments, when a filter column in the device is in the first position, a solution can be pumped out of a first cavity; in some embodiments when the device is moved into a second position, a second solution is pumped. Devices can contain one or more overlaps of the filter column and one or more chambers containing liquid. In some embodiments, the distance and/or angle among different overlap positions can be programmed by the device design.

In some embodiments, a lysed sample can be flowed through a filter column to capture a target (e.g. DNA or RNA) on a filter column. In some embodiments, subsequent steps involve washing—e.g. the captured DNA or RNA specific to resistant or susceptible cells can be washed, such as with a washing buffer, and eluted off the column with elution buffer to be released from the column.

In some embodiments, after the target (e.g. DNA/RNA) is enriched and eluted off the column, the eluted DNA/RNA can be transported from the column into the next chamber or module, also called quantification module or device, that in some embodiments is suitable for quantification of target (e.g. DNA/RNA) molecules.

Other Modules and Elements

In some embodiments, the device contains an operation module, such as for example a module to operate devices (including integrated devices). In some embodiments, an operation module is configured to perform one or more of the following functions: motor control, shaft rotation, heating, image capture, and image processing. In some embodiments, an operation module comprises one or more motors and shafts. In some embodiments, an operation module comprises one or more rotary valves. In some embodiments, one or more layers are connected to a shaft and are capable of rotation. In some embodiments, one or more layers are configured to disconnect from the shaft. In some embodiments, one or more layers comprise a detent ball and remain connected to the shaft at low torques but disconnect at high torques (i.e. when the layer is physically stopped).

In some embodiments, one or more layers are preprogrammed to rotate a specified degree. In some embodiments, the operation module comprises a stopping component to stop one or more layers physically.

In some embodiments, the device contains an enrichment or pre-concentration module. In some embodiments, the enrichment module concentrates the number of organisms. In some embodiments, these devices contain a threshold module. In some embodiments, the cutoff module limits the number of organisms to a threshold value. In some embodiments, the enrichment and threshold module are combined. In some embodiments, the enrichment module is designed to process between 1 mL and 10 mL. In some embodiments, the enrichment module is designed to process between 100 µL and 100 mL. In some embodiments, the enrichment module is designed to process between 100 µL and 1 L.

In some embodiments, the device contains an incubation chamber and at least one detection chamber in proximity, such as within 10 cm of each other. In some embodiments, the device contains an incubation chamber and at least one detection chamber in proximity, such as within 20 cm of each other. In some embodiments, the device contains an incubation chamber and at least one detection chamber in proximity, such as within 1 m of each other.

In some embodiments, the integrated device integrates one or more of the following: enrichment module, cutoff module, incubation module, sample prep module, quantification module, and operation module. In some embodiments, the integrated device integrates the incubation module, with the autonomous device and digital SlipChip. In some embodiments, modules have interlocking features. In some embodiments, modules are interchangeable. In some embodiments, modules useful for sample preparation and handling are included in the device.

In some embodiments, an integrated device has dimensions smaller than 10×10×10 cm, or integrated device has dimensions smaller than 20×20×20 cm.

In some embodiments, the device comprises flexible materials such as, but not limited to PDMS, Tango+(a 3D-printable soft material), or rubber. The flexible materials enable the device to perform leak-proof liquid movement of a sample among modules (e.g., between the sample preparation module to the amplification module). In some embodiments, the device comprises channels/microchannels to interface modules. In some embodiments, the device comprises syringe pumps/teflon tubing. In some embodiments, the device comprises embedded channels in 3D-printed parts. In some embodiments, the device comprises 3D-printed valves. These components can also enable the device to perform leak-proof liquid movement of a sample among modules.

In some embodiments, a quantification device has a series of compartments with varying volumes. In some embodiments, a quantification device incorporates a series of on-chip dilutions before loading a series of single volume compartments. In some embodiments, these devices enable a large dynamic range without abnormally large compartment sizes As an example, a sample can be diluted 1:10 four consecutive times. Each dilution is loaded into a series of single volume digital compartments. 400 compartments can quantify and resolve 1.5-fold differences in concentration with a 1-log dynamic range. Thus, the example device consists of four sets of 400 compartments each. The four 10× dilutions can be loaded into these four sets of single volume compartments and will enable 1.5-fold resolution with 4-log dynamic range and antibiotic susceptibility testing.

In some embodiments, the devices comprise a readout module or mechanism to generate a readout. Platforms can be compatible with one or more readout or detection mechanisms. For example, a platform can be transparent or translucent in part or in total, allowing fluorescent measurement, detection of precipitate or gas bubble, or other visual observation. A platform can comprise visual detectors, such as CCDs, CMOS sensors, cameras, photon detectors, and other sensors. In another example, a platform can comprise electrical sensors, such as electrodes positioned within microwells. Platforms can be compatible with off-loading of samples for analysis. For example, a platform can permit unloading of droplets or contents of wells for mass spectrometry, sequencing, or electrophoresis.

In some embodiments, the method of reading the quantification module include, but are not limited to, fluorescence microscopy, brightfield microscopy, a camera, a digital camera, or a cell phone camera, among others. In some embodiments, a base station with an camera is used to capture the image. Image processing can be integrated in the base station or the image file can be transferred to a computer. In some embodiments, a cell-phone picture is taken. Phone software can be utilized to process the image or the image can be uploaded to a server for image processing.

In some embodiments, heating elements are embedded in the device, such as those into which an incubation module can be inserted, such as for example a bath containing high thermal conductivity materials. In some embodiments, amplification and detection of a target (e.g. RNA/DNA) can include heating elements on the device. Examples of heating elements can include, but are not limited to, heating by using electrical power, chemical reaction, or phase change materials. In some embodiments, transparent thermally conductive materials can be used such that images of the amplification region can be captured through the heating unit.

In some embodiments, these devices incorporate mixing methods. In some embodiments, jet macro-mixing can be used to mix solutions (Nealon, A. J., O'Kennedy, R. D., Titchener-Hooker, N. J., & Lye, G. J. (2006). Quantification and prediction of jet macro-mixing times in static microwell plates. Chemical engineering science, 61(15), 4860-4870). In such an approach, one or more solutions are pressurized and an opening between them allows one solution to flow into the other, or for both solutions to collide. In some embodiments, one or more solutions are gaseous mixtures, and generate bubbles to form a bubble mixer. In some embodiments, mixing is used to mix liquid samples and dry reagents. Alternating positive and negative pressures can be applied to improve mixing. In some embodiments, mixing can be accomplished mechanically, for example by an impeller, magnetic bead agitation, gravity, passive structures, etc., or combination of such methods.

In some embodiments, these devices contain a chamber or array of chambers for combining or mixing reagents.

In some embodiments, these devices contain special materials. In some embodiments, one or more materials in the device are compatible with organisms (e.g. materials that do or do not negatively affect viability). In some embodiments, a material or surface coating can be added to materials for one or more of the following purposes: to enhance thermal conductive properties, control surface chemistry/ surface tension (hydrophobicity), enhance organism viability, alter diffusive properties, prevent adsorption, sealing, prevent leeching (i.e. plastics), alter rigidity, among others.

In some embodiments, these devices utilize one or more manual steps—such as but not limited to addition of sample, insertion of reagents, adjusting settings, slipping, rotation, attaching pumping lid, actuating pumping, inserting materials, connecting modules, initiating the device, initiating heating, transferring fluids, removing modules capturing images, etc.

In some embodiments, devices can be fabricated by a number of methods including 3D printing, injection molding, embossing, wet etching, and other methods known in the art.

Device Uses

The digital platform in some embodiments of the device allows for detection of lower abundance bacteria than in current nucleic acid-based technologies, which enables more robust analysis of blood and CSF samples. The increased precision of digital technology improves monitoring of patient response to therapy.

The sample-prep module can provide rapid nucleic acid extraction and purification within 5 min, reducing degradation of unstable RNA.

The point-of-care module can allow for broad-based testing in clinical populations across a wide range of infections, and in both clinical trials and surveillance.

The digital amplification module can allow for a clearer understanding of low-level infection in a more proximate timeframe than culture methods and can inform on the heterogeneity of response to antimicrobials.

In one embodiment, the devices can be used with sample preparation technology to isolate bacterial DNA and RNA rapidly and in high yield from target microorganisms or cells, such as for example *Klebsiella pneumoniae, Pseudomonas aeruginosa*, and extra-intestinal pathogenic *E. coli* and can include clinical samples and can include a variety of bodily fluids, such as for example urine. Sample-prep SlipChip for bacterial DNA and RNA extraction and purification from urine samples containing *Chlamydia trachomatis* has previously been validated. Viral RNA extraction and purification from plasma samples containing HCV or HIV viral particles has also been validated. In one embodiment, the devices can be used to perform sample preparation in less than 5 min and with samples handling a range of volumes, such as for example up to 0.5 mL. In some embodiments, the device can be used for rapid detection of samples containing low bacterial loads.

In some embodiments, the devices can be used to extract and purify nucleic acids, such as bacterial DNA and RNA from samples (e.g. a urine sample) spiked with a bacterial target (such as for example *K. pneumoniae, P. aeruginosa*, or *E. coli*) in some cases in an extremely short period of time (such as for example less than 5 minutes) and in some cases with a yield above 80% compared to standard bench methods, and at a quality suitable for both digital and real-time quantification.

Bacterial RNA is known to be unstable and expression levels can change rapidly. In cases where the quantity and quality of purified RNA can be compromised, the devices described in this disclosure can be used to further shorten the sample preparation protocol, such as for example to less than 3 min. This time frame has previously been demonstrated for isolation of viral RNA from blood plasma. In some embodiments, the lysis step can be modified by adding additional detergents or inhibitors to minimize the activity of RNase.

In some embodiments, the device can combine SlipChip sample preparation and digital quantification technologies for rapid, reproducible and quantitative measurements of nucleic acids, such as for example bacterial RNA levels in a sample, (e.g. a clinical urine sample) spiked with, for example, *K. pneumoniae, P. aeruginosa*, and *E. coli* from 100 CFU/mL to $1 \times 10^6$ CFU/mL with 3-fold resolution. In some embodiments, the devices described herein have a performance greater than 99% specificity.

In some embodiments, the device or platform combines more than one module to quantify and identify the target microorganisms in for example, clinical urine samples.

In some embodiments, the devices will enable assays that perform both sample prep and digital amplification. In some embodiments, the total assay time can be less than 60 min, less than 30 minutes, less than 15 minutes. Current PCR protocols can be shortened by optimizing denaturation time, denaturing temperature, or by combining the annealing and extension steps (Bio-Rad). Using optimized amplification enzymes or fast thermal cyclers, 10 minute amplification can be achieved. (Wheeler, et al., 2011, Analyst, 3707-3712, Neuzil, et al., 2006, Nucleic Acids Research, e77). In some embodiments, these devices can perform sample prep in less than 5 min, a reverse transcription step of less than 5 min, and a digital SlipChip workflow less than 35 min, to achieve for example a less than 45 min workflow. In another embodiment, this RT digital PCR instrument can be used to help optimize the chip thermal cycling protocol.

In some embodiments, the devices can enable rapid diagnosis of drug resistance using small numbers of cells originating directly from clinical samples. The devices described here can in some embodiments be used to answer the following questions, which are essential to the design of rapid AST assays that don't rely on many rounds of cell division, and essential for doing AST assays when a limited number of cells is available, as is often the case for blood and CSF: (i) What are the single-cell growth, phenotypic, and gene expression profiles of drug-susceptible and drug-resistant microbial populations or cells shortly upon drug exposure? (ii) Are there "sentinel" cells that can very rapidly (within less than 15 or even 7 minutes) predict the susceptibility or resistance of the population or cells? (iii) How many cells are necessary for reliable prediction of the drug susceptibility or resistance of the clinically relevant bacterial population? (iv) What is the gene expression signature and the shortest drug exposure that reliably predicts antibiotic susceptibility and resistance when the measurement is performed on pooled cells, and how closely can this measurement approximate the performance of the single-cell assays?

In some embodiments, the devices described herein can be used to monitor single cells from the target organisms or cells in response to drug exposure. In some embodiments, these devices have the capability to monitor growth, metabolic activity, phenotypic variation, and levels of gene expression at the single cell level.

In some embodiments, the devices enable measurement of the distribution of growth rates and doubling times of susceptible strains or cells in the presence of standard dilutions of a drug, such as for example ciprofloxacin (a fluoroquinolone) or ampicillin (such as a (3-Lactam). Ciprofloxacin is regarded by clinicians as having the ability to prevent growth immediately (Barcina, et al., 1995, Journal of Microbiological Methods, 139-150), while ampicillin's mode of action is believed to allow as many as 5 generations of cell division before lysis occurs (Rolinson, 1980, Journal of General Microbiology, 317-323). It is well known that antibiotics can be rapidly lost in plastic devices, such as PDMS used for Fluidigm chips. Therefore, in some embodiments our devices can be composed of glass and in some embodiments they can be used to recover fluids (Ma, et al., 2014, PNAS, Ma, et al., 2014, Integrative Biology) to measure post-assay antibiotic concentrations.

In some embodiments the devices can measure gene expression by quantifying RNA present in single cells. The SlipChip device can analyze DNA from live bacteria from individual wells (Ma, et al., 2014, PNAS, Ma, et al., 2014, Integrative Biology) and can quantify the number of RNA copies in each well. In some embodiments, the devices can combine these applications to create single-cell gene expression assays.

In some embodiments, the devices can use genes reported to be differently regulated in response to antibiotic, such as recA and LexA (Barczak, et al., 2012, Proceedings of the National Academy of Sciences, 6217-6222), genes induced by OxyR and SoxS in response to antibiotic-induced oxidative stress (Dwyer, et al., 2014, Proceedings of the National Academy of Sciences, E2100-E2109), and measure genes near the origin of replication (oriC) that become amplified after treatment with antibiotics targeting DNA replication (Burgess, 2014, Nat Rev Genet, 362-362, Slager, et al., 2014, Cell, 395-406).

In one embodiment, the devices can be used for specific quantification of gene expression markers (such as for example 16S RNA and pre-rRNA), to identify drug susceptibility (Mach, et al., 2011, The Journal of Urology, 148-153, Rolain, et al., 2004, Journal of Antimicrobial Chemotherapy, 538-541). In another embodiment the devices can be used to establish the smallest change detectable in gene expression with at least 20 clinical isolates under a variety of incubation conditions and times (such as for example less than 10 min, or around 10 min, 20 min, or 30 min).

The technology described herein may, in some embodiments, optimize and/or accelerate these methods for resistance quantification of clinical samples. In some embodiments, the results of assays done on the devices described herein will be available in minutes rather than hours. In some embodiments, the invention enables a diverse set of manipulations on diverse volume scales (such as for example sample preparation to single-cell manipulation, single-molecule quantification, and cell-phone readout).

In some embodiments, the invention uses digital single molecule measurements to address antimicrobial susceptibility and provide ultra-sensitive measurements that can radically improve detection limits and can provide quantitative data, which is important for differentiation of pathogens from contamination and enabling earlier differentiation between drug-resistant and susceptible organisms. In some embodiments, this invention can be used for phenotypic, metabolic, and gene-expression profiling measurements in response to antibiotics and can use individual bacterial cells and can use samples originating from a clinical setting.

In some embodiments, this invention uses high-throughput single-bacterial-cell measurements in the clinic to determine antibiotic susceptibility. In some embodiments, this invention allows differentiation of the state of individual microorganisms or cells, such as for example samples obtained from a clinical human sample or from an environmental sample, and can allow temporal quantification of their individual responses to antibiotics and therefore ultrafast drug-susceptibility measurements.

In some embodiments, the devices can be used to rapidly identify cells, quantify their load, and provide their susceptibility profile. In some embodiments the devices can be used to incubate cells with drugs and then rapidly extract and quantify nucleic acids, such as for example RNA, in a contamination-free platform to determine drug susceptibility. In some embodiments, this invention enables microbial and cell identification and drug susceptibility testing outside of CLIA clinical laboratories.

In some embodiments, the devices enable handling of large sample volumes over multiple steps, enabling fast, efficient nucleic acid extraction. Sample preparation SlipChip has been validated previously for extraction and purification of bacterial RNA from urine spiked with *C. trachomatis* and viral RNA from blood plasma spiked with HCV viral particles. This device can process a 0.5 mL clinical sample, and the entire workflow, from raw sample to purified nucleic acid, can be completed within 5 minutes with no user intervention. This device has been validated for analyzing bacterial DNA from urine samples spiked with *C. trachomatis*, viral RNA from blood plasma spiked with HIV viral particles, and viral RNA from culture of influenza viruses.

In some embodiments, this invention includes a device for determining drug resistance of a cell or microorganism that incorporates nucleic acid quantification. In some embodiments this invention includes a device in which a sample derived from an organism pre-incubated with a drug is introduced into the devices described above.

In some embodiments, the devices measure the change in expression or in copy numbers of genes, such as for example genes close to OriC (such as for example, competence genes), after a sublethal dose of drug exposure. In some embodiments, gene expression, such as expression of the OriC-proximal genes, can be compared to the expression of household genes or to selected genes, such as genes located at the terminator (ter) site.

In some embodiments, the devices can assess cell competence itself in response to sublethal doses of a drug as an assay for drug susceptibility.

In some embodiments, the devices can assay bacterial susceptibility, such as for example susceptibility to β-lactam antibiotics, by compartmentalizing cells or microorganisms in small volumes via stochastic confinement (e.g. via droplets or wells of small size, such as picoliter or nanoliter). In some embodiments, these samples are taken from blood or urine or CSF. In some embodiments the cells are in the presence of an antibiotic and a fluorogenic reporter. In some embodiments, the devices can detect persisters and genotypically resistant, but phenotypically silent, cells, such as for example by induction of a resistant phenotype.

In some embodiments, the devices and methods herein can be used to analyze a time course of gene expression of microorganisms in a sample. For example, this analysis can monitor a change of gene expression in response to a drug. For example, time points of gene expression immediately prior to treatment with a drug and at one or more time intervals after addition of the drug to the microorganisms could be used (such time intervals can include one or more of about 3 minutes, about 5 minutes, about 7 minutes, about 10 minutes, about 15 minutes, about 20 minutes).

In some embodiments, the devices and methods herein can include incubation of microorganisms at a controlled temperature, such as for example 35° C., 37° C., 38° C., 39° C., or 40° C.

Using single cell analysis will enable observation of stochastic response times, enabling outlier cells that respond quickly to provide earlier-than-average results.

Figure 9:
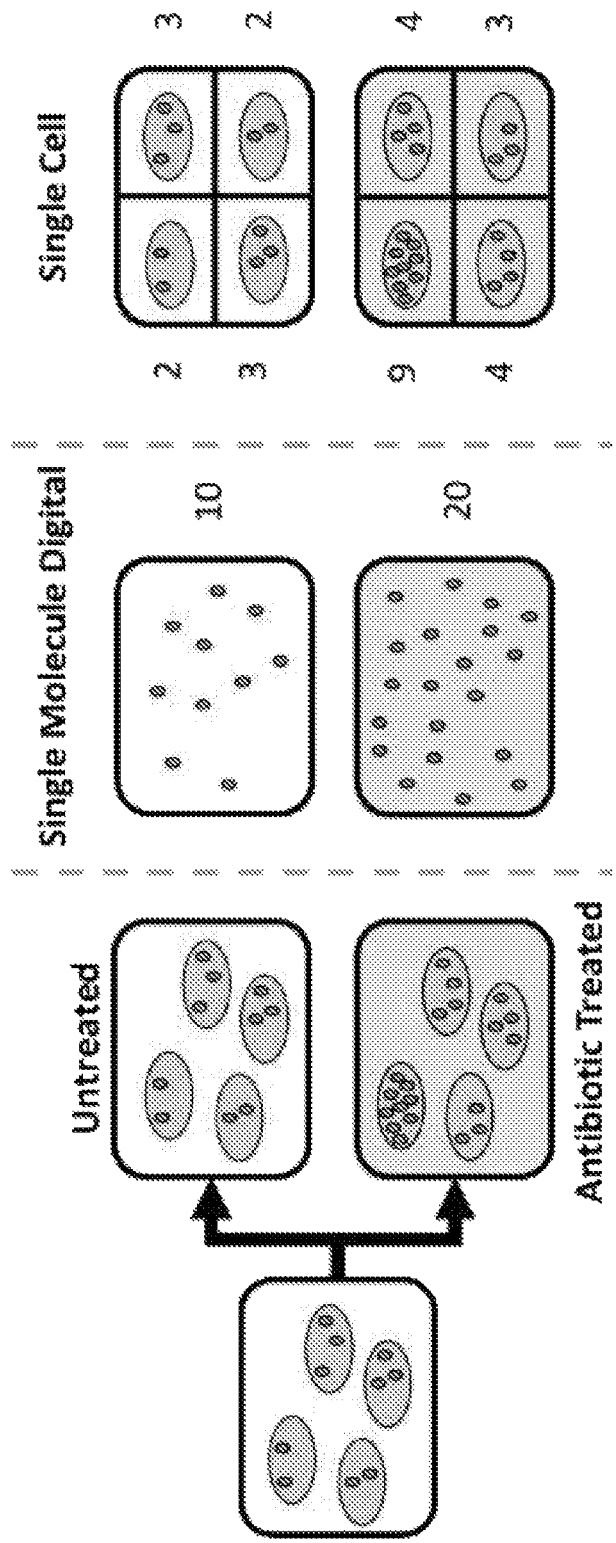
FIG. 9 shows a flowchart for performing single-molecule and single-cell measurements to detect changes in individual cells from a heterogeneous population in response to drug treatment.

In some embodiments, the device provides a mechanism to perform single-molecule and single-cell measurements to detect small changes in relative nucleic acid concentrations and heterogenous cellular response to antibiotic treatment in pathogenic bacteria (FIG. 9). First, a group of cells are subjected to antibiotic treatment, then changes in a selected gene's expression are quantified by two methods. For single-molecule digital amplification, cells are lysed together then RNA is quantified with high resolution to detect small overall changes. For single-cell measurements, cells are confined to individual wells in a microfluidic device and qPCR on each cell is used to take advantage of large, early responses in "sentinel" cells.

In some embodiments, the device can be used to assay bacteria from isolates and clinical samples in our devices and evaluate whether single cell analysis reveals "sentinel cells" that predict susceptibility or resistance earlier than possible in pooled-cell analysis (FIG. 9). In some embodiments, the device can be used to optimize the media and growth conditions within a device to determine the minimum amount of time required to ensure that all vigorous cells have shown signs of growth. In some embodiments, the devices can be used to design and optimize rapid assays to determine drug susceptibility and drug resistance, for example antibiotic susceptibility and resistance of *Klebsiella pneumonia, Pseudomonas aeruginosa*, or extra-intestinal pathogenic *Escherichia coli*. In some embodiments the devices can detect heteroresistance (where the tested sample contains both a susceptible strain or cell and a resistance strain or cell). This phenomenon is well documented for Gram-positive bacteria (Musta, et al., 2009, Journal of Clinical Microbiology, 1640-1644, Kim, et al., 2002, Journal of Clinical Microbiology, 1376-1380, Wong, et al., 1999, Clinical Infectious Diseases, 760-767, Ariza, et al., 1999, The Lancet, 1587-1588, Editors, 2001, Journal of Medical Microbiology, 1018-1020) and some Gram negatives (Pournaras, et al., 2007, Journal of Medical Microbiology, 66-70) and is relevant to patient treatment and outcome, although detection of heteroresistance is not viewed as a frequent clinical problem for Gram-negative bacteria. In some embodiments, when heteroresistance is observed, the devices disclosed herein can be used to identify heteroresistance by sample types so that they can be targeted for analysis, such as for example by the single-cell platform.

In some embodiments, the devices can be used to incubate a microorganism or cell, such as for example incubating isolates of *K. pneumoniae* with antibiotic samples of, for example, Cefazolin, Ceftriaxone, Ciprofloxacin, Piperacillin-Tazobactam, Trimethoprim-Sulfamethoxazole, and Meropenem and *P. aeruginosa* with Ciprofloxacin, Piperacillin-Tazobactam, and Meropenem.

Figure 10:
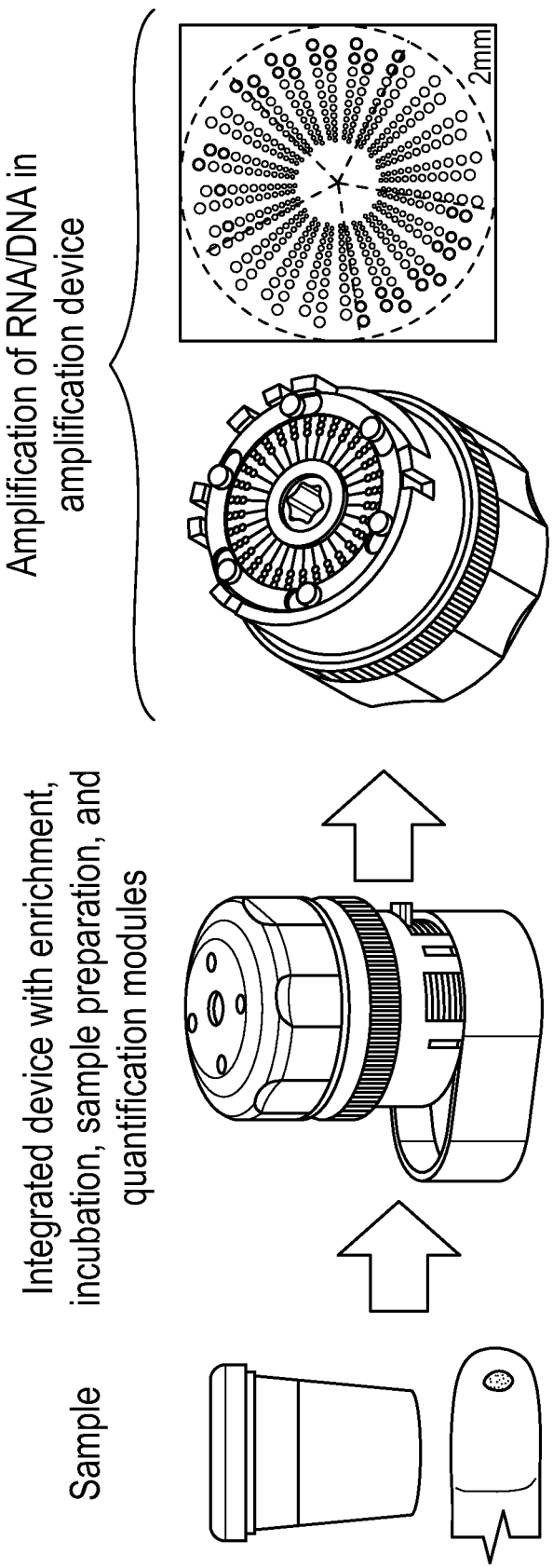
FIG. 10 depicts a flow chart for a point of care device that provides an assay and results from the assay on a sample in a single integrated device.

In some embodiments the devices can be integrated, so that for example the sample-prep SlipChip and the digital SlipChip are integrated to improve workflow/efficiency and avoid contamination. Integration of the two chips can prevent RNA degradation and eliminate contamination and simplify workflow. In some embodiments the devices can be integrated, so that for example the devices combine the identification device and the AST device to identify the pathogen, its load, and its antibiotic susceptibility (FIG. 10).

In some embodiments, the invention identifies and quantifies bacteria and assesses antimicrobial susceptibility. In some embodiments, the platform leverages existing thermocyclers found in most laboratories, enabling a low-cost digital PCR capability to even the smallest of clinical laboratories in an "open" format that would allow for expansion of the test menu. In some embodiments of the device, sample preparation can be performed on a macrofluidic, disposable chip that does not require external power.

In some embodiments, the invention incorporates the capability to quantify and assess antimicrobial susceptibility into a CLIA-waived structure in order to provide access to the technology in primary care and global health settings. In some embodiments, the invention uses isothermal enzymes, which have been well studied on the SlipChip platform, and can allow for equipment-free testing under a range of environmental conditions. In addition, in some embodiments the results are cell phone readable and can be obtained by a minimally trained user.

In some embodiments, the device can be modified for use with blood and can also include *Acinetobacter baumannii* in the test suite. In some embodiments the device can be used with low-abundance specimens and has RT PCR capability, which allows for more accurate testing of antimicrobial susceptibility even in low-abundance specimens. These capabilities offer significant clinical value in hospital settings.

In some embodiments, the device can rapidly diagnose an infection, such as for example a urinary tract infection (UTI), through species identification and quantification, and in some embodiments the device can also characterize the drug resistance of the species causing the infection. The device can thus significantly enhance clinicians' ability to provide antibiotic stewardship, and also to avoid inappropriate treatment when a UTI is not present or when bacterial counts do not warrant therapy.

In some embodiments, the device can quantify the number of bacteria that exist at the time of sample collection to determine if the bacterial load warrants therapy, as physicians typically do not treat at lower bacterial concentrations. In some embodiments, validation can also be done on the device. The bacterial concentration from the device can be correlated with the colony counts obtained using the current "gold standard" culture method for bacterial detection and characterization. In some embodiments, the device can be used to identify which bacteria are present using nucleic acid detection on a digital chip format.

In some embodiments, the device can be used to assess antimicrobial resistance of the identified organism to help guide choice of therapy. In some embodiments, samples, such as urine samples, can be incubated with a range of drugs, such as antibiotics, and gene expression tests can determine which drug regimen is best suited to treat the infection (for example by identifying to which drugs the bacteria are susceptible).

In some embodiments, the device can identify bacterial species with greater than 99% specificity and quantify bacterial load in urine over a dynamic range of 100 CFU/mL to 1,000,000 CFU/mL with better than 3-fold resolution.

In some embodiments of the device and methodology, the workflow allows rapid AST (anti-microbial susceptibility testing) for one or more species or strains or cell types against a panel of one or more drugs in less than 95 minutes, less than 30 minutes, less than 15 minutes, less than 5 minutes.

In some embodiments, the device is an integrated device capable of performing sample preparation and digital quantification so that it can be used for both quantification of bacterial load and quantification of gene expression for AST with at least 80% recovery of nucleic acids.

In some embodiments, the device enables a workflow that combines an identification device and an AST device to identify the organisms, quantify their load, and determine their antibiotic susceptibility.

A device for sample preparation from urine that has at least 80% recovery of nucleic acids in comparison to standard nucleic acids in comparison to the existing Qiagen sample preparation kit. In some embodiments, sample preparation can be performed automatically, without centrifugation, in less than 5 min, whereas the Qiagen method takes 30 min.

In some embodiments, bacterial species identification can be performed with greater than 99% specificity for organisms in comparison to culture.

In some embodiments, quantification of live bacterial load, such as in urine, can be performed over a dynamic range of 100 CFU/mL to 1,000,000 CFU/mL with better than 3-fold resolution compared to common culture methods.

In some embodiments, the invention enables a workflow that allows rapid AST (antimicrobial susceptibility testing) for one or multiple species against a drug or a panel of two or more antibiotics in less than 95 min.

In some embodiments, the invention enables a workflow that combines the preparation module or device, identification and quantification module or device and the AST module or device to identify the organisms, quantify their load, and/or determine their antibiotic susceptibility, in less than 2.5 hours, less than 2 hours, less than 1 hour, less than 30 minutes.

In some embodiments, the device provides multiplexed and quantitative diagnostic measurements of nucleic acids or proteins in CLIA-based and Limited Resource Settings (LRS) at a quality that is on par with the equipment typically used in reference laboratories.

In some embodiments, the platform is "open" so that reagents for other/additional bacteria can be added and the scope of measurements expanded.

In some embodiments, the device enables multiplexed and digital nucleic acid-based quantitative measurement of HCV and HIV viral loads with a dynamic range of $10^5$. In some embodiments, the device enables multiplexed detection of pathogens (including bacteria and fungi).

In some embodiments, the device is a microfluidic device, such as a SlipChip, that enables sample preparation with one or more of the following characteristics: a device that meets or exceeds commercial standards for low cost fabrication, a device that ultimately will not require user intervention, a device that ultimately will not require electricity to operate, a sample-prep module or device that enables sample prep for HCV, *chlamydia* and gonorrhea, and influenza in less than 5 min, a device that uses inexpensive plastics and is amenable to mass-production technologies, a device in which operation and imaging can be performed by an untrained child, and a device in which operation and imaging can be performed using automatic cloud-based analysis and data transmission.

In some embodiments, the device can identify bacterial species with greater than 99% specificity and quantification of bacterial load in urine over a dynamic range of 100 CFU/mL to 1,000,000 CFU/mL with better than 3-fold resolution.

In some embodiments, the device can identify and quantitatively measure bacterial DNA and RNA from organisms, such as for example *Klebsiella pneumoniae, Pseudomonas aeruginosa*, and extra-intestinal pathogenic *Escherichia coli* from clinical samples of urine, and can be adapted to also provide a quantitative measure of bacterial load.

In some embodiments, the device is a digital microfluidic device, such as a digital SlipChip, for identification and quantification of bacterial DNA and RNA extracted from a urine sample spiked with *K. pneumoniae, P. aeruginosa* and *E. coli*. In some embodiments, the device can have above 99% specificity for DNA/RNA amplification for organisms or cells, and provide quantification of DNA/RNA extracted over the dynamic range of 1,000 to 1×10⁷ copies/mL with 3-fold resolution.

In some embodiments, the device is a digital microfluidic device, such as a digital SlipChip, can be used for quantification of live bacterial load in urine sample by quantification of 16S rRNA. In some embodiments, the device can incorporate a rapid incubation step (less than 10 min) and can evaluate renormalization of gene expression for different sample types under various storage conditions.

In some embodiments, the device is a digital microfluidic device, such as a digital SlipChip, capable of quantification of RNA markers purified using standard bench method to quantify live bacterial load. In some embodiments, the device is a sample-prep device, such as a sample-prep SlipChip that can have higher than 80% of recovery of both DNA and RNA with reference strains and clinical isolates of *K. pneumoniae, P. aeruginosa* and *E. coli*. In some embodiments, the device can recover a quality of purified DNA and RNA suitable for both digital device applications and real time qPCR In some embodiments, the device can extract and purify bacterial DNA and RNA from urine sample spiked with reference strains of *K. pneumoniae, P. aeruginosa* and *E. coli* with higher than 80% recovery compared to the standard bench method in less than 5 minutes.

In some embodiments, the methods employ an integrated device with multiple functionalities and in other embodiments the methods employ non-integrated devices, such as separate sample-prep devices and digital devices for identification and quantification. In some embodiments, the combination of the integrated sample-prep and digital devices for identification perform with greater than 99% specificity and are capable of quantification of a bacterial load with 3-fold resolution over the dynamic range of 100 CFU/mL to 1,000,000 CFU/mL.

In some embodiments, the device can perform a rapid Antimicrobial Susceptibility Test (AST) for organisms, such as *K. pneumoniae, P. aeruginosa* and *E. coli* by incubating samples with drugs for a short period of time, then quantifying RNA expression markers. In some embodiments, the device can provide a sample to answer turnaround of less than 2.5 hours or less than 2 hours or less than 1 hour. In some embodiments, the device can be used with clinical isolates or clinical samples.

In some embodiments, the device can quantify gene expression markers over a dynamic range of 100 copies/mL to 10,000,000 copies/mL. In some embodiments, the device can be used to identify the detectable minimal difference over the same dynamic range, and this will provide guideline for incubation time and antimicrobial susceptibility test for a particular cell or microorganism.

In some embodiments, the device can be used to incubate samples with at least 20 clinical isolates of *E. coli* in the presence or absence of Ampicillin. In some embodiments of the device, bacterial RNA can be prepared and one or more RNA markers can be quantified. In some embodiments of the device the results will have at least 95% in agreement with standard clinical methods.

In some embodiments, the device can be used to incubate *E. coli* with a drug, such as an antibiotic, including Cefazolin, Ceftriaxone, Ciprofloxacin, Piperacillin-Tazobactam, Trimethoprim-Sulfamethoxazole, and Meropenem. In some embodiments of the device, bacterial RNA can be prepared and expression level of RNA markers quantified using digital methods and in a time frame of less than 95 min, less than 60 minutes, less than 30 minutes, less than 15 minutes.

In some embodiments, the device can be used to incubate negative urine spiked with at least 20 clinical isolates of *E. coli* in the presence and absence of Cefazolin, Ceftriaxone, Ciprofloxacin, Piperacillin-Tazobactam, Trimethoprim-Sulfamethoxazole, and Meropenem. In some embodiments, the device can quantify expression level of RNA markers with a workflow performance of less than 5% major errors, and no very major errors.

In some embodiments, the device can incubate samples of at least one clinical isolate in the presence and absence of a drug of a panel of clinically relevant drugs. In some embodiments, the device can quantify expression level of RNA markers in bacterial DNA to perform AST and has less than 5% major errors, and no very major errors.

In some embodiments, the device integrates sample preparation and digital capabilities. The integration of the devices can prevent degradation and eliminate contamination and enable nucleic acid extraction, purification, and digital quantification with above 99% specificity and in less than 55 minutes, less than 30 minutes, less than 15 minutes.

In some embodiments, the device can provide quantitative measurement of bacterial DNA and RNA, such as from urine samples spiked with *K. pneumoniae* (ATCC 700603), *P. aeruginosa* (ATCC 27853), and *E. coli* (ATCC 25922) with above 99% specificity and in less than 55 minutes. In some embodiments, the device or integrated device can provide quantification of bacterial load at dynamic range of 100 CFU/mL to 1,000,000 CFU/mL with greater than 3-fold resolution.

In some embodiments, the device can be used for quantification of gene expression level for at least 20, at least 50 or at least 100 clinical isolates with incubation in the presence and absence of selected drugs In some embodiments, the device performance, including bacterial load and AST, is comparable to CLSI reference methods. In some embodiments, the error of performance is less than 5% minor errors, less than 2.5% minor errors, less than 1% minor errors.

In some embodiments, the performance has, less than 1% major errors, less than 0.5% major errors, less than 0.1% major errors. In some embodiments, the device has no very major errors.

Kits

A kit can include a SlipChip device, and a supply of a reagent selected to participate in nucleic acid amplification. In some embodiments, the reagent can be disposed in a container adapted to engage with a conduit of the first component, the conduit of the second component, or both. Such a container can be a pipette, a syringe, and the like. In some embodiments, the kit includes a heater.

Some embodiments of the device could be used to detect different biological targets such as, for example, proteins, bacteria, viruses, infectious agents etc., using nucleic acid labels. In some embodiments the target is tagged with an oligonucleotide which can be used for detection. The oligonucleotide tag can be further amplified using any one of a number of different nucleic acid amplification strategies, such as for example, PCR, LAMP, RPA, NASBA, RCA, etc. The oligonucleotide tag could also be visualized using fluorescent probes for example as shown by Chen (Huang, Suxian, and Yong Chen.

"Polymeric Sequence Probe for Single DNA Detection." *Analytical chemistry* 83.19 (2011): 7250-7254.)

EXAMPLES

These examples are provided for illustrative purposes only and not to limit the scope of the claims provided herein.

Example 1: Formation of a SlipChip

The procedure of fabricating desired glass SlipChips using soda lime glass was based on previous work. The two-step exposing-etching protocol was adapted to create wells of two different depths (5 µm for thermal expansion wells, 55 µm for all the other wells). After etching, the glass plates were thoroughly cleaned with piranha acid and DI water, and dried with nitrogen gas. The glass plates were then oxidized in a plasma cleaner for 10 minutes and immediately transferred into a desiccator for 1 hour of silanization. They were rinsed thoroughly with chloroform, acetone, and ethanol, and dried with nitrogen gas before use.

Plastic polycarbonate SlipChip devices were directly oxidized in a plasma cleaner for 15 minutes after they were received from microfluidic ChipShop GmbH, and then transferred into a desiccator for 90 minutes of silanization. They were soaked in tetradecane for 15 minutes at 65° C. and then rinsed thoroughly with ethanol, then dried with nitrogen gas before use. Plastic SlipChip devices were not reused.

The SlipChips were assembled under de-gassed oil (mineral oil: tetradecane 1:4 v/v; Fisher Scientific). Both top and bottom plates were immersed into the oil phase and placed face to face. The two plates were aligned under a stereoscope (Leica, Germany) and fixed using binder clips. Two through-holes were drilled in the top plate to serve as fluid inlets. The reagent solution was loaded through the inlet by pipetting.

Example 2: Digital Amplification in a SlipChip

Digital PCR was performed on a SlipChip according to the protocols described in Shen et al. 2010). Feng Shen, Wenbin Du, Jason E. Kreutz, Alice Fok, and Rustem F. Ismagilov, "Digital PCR on a SlipChip," Lab Chip 2010 10: 2666-2672.

Briefly, in this published method, top and bottom SlipChip plates were etched with microfluidic channels and wells via photolithography and HF etching. The top and bottom plates were aligned in a mixture of 20% mineral oil/80% tetradecane and then clamped to hold in place. DNA from the extractions described above was added to PCR master mix. This solution was loaded into the SlipChip device with a pipette. After loading, a slip broke the channels into 1280 individual 3 nL compartments. Next, the SlipChip was clamped, sealed, and placed on a thermocycler for the following temperatures: 92° C. for 3 minutes, 40 cycles of: 92° C. for 20 seconds, 62° C. for 20 seconds, and 72° C. for 25 seconds. The SlipChip was imaged, positive and negative wells were counted, and the concentration of target DNA was calculated using Poisson statistics.

Example 3: Detection of Differences in rDNA Between Treated/Untreated Susceptible E. coli Over Time In one example, a ciprofloxacin-susceptible E. coli isolate from a patient with a urinary tract infection was pre-cultured in Bacto Brain Heart Infusion (BHI) media to high cell density prior to dilution and treatment with and without 2.5 ug/mL ciprofloxacin for 10, 20, and 30 minutes. DNA from treated and non-treated samples was extracted with Epicentre QuickExtract DNA extraction buffer. Quantitative PCR was performed with primers specific to the target rDNA gene for 23S. The following primers specific for 23S rDNA were used:

```
                                        (SEQ ID NO: 1)
      5'-TGCCGTAACTTCGGGAGAAGGCA-3'

(SEQ ID NO: 2)
      5'-TCAAGGACCAGTGTTCAGTGTC-3'
```

Figure 11:
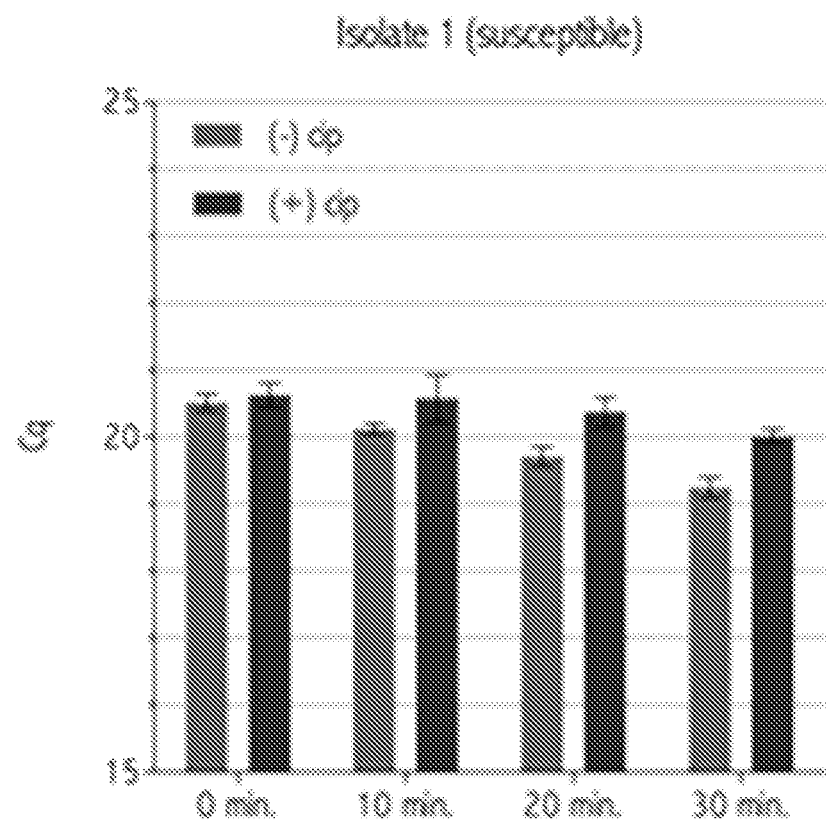
FIG. 11 shows the fold change in rDNA copy number for ciprofloxacin-susceptible *E. coli* treated with 2.5 ug/mL ciprofloxacin (right bar at each timepoint) and non-treated (left bar at each timepoint) samples measured at 10, 20, and 30 minutes as determined by qPCR.

A 1.37, 1.58, and 1.70 fold change in rDNA copy number between the treated (right bar at each timepoint) and non-treated (left bar at each timepoint) samples was measured at 10, 20, and 30 minutes (FIG. 11).

Figure 12A:
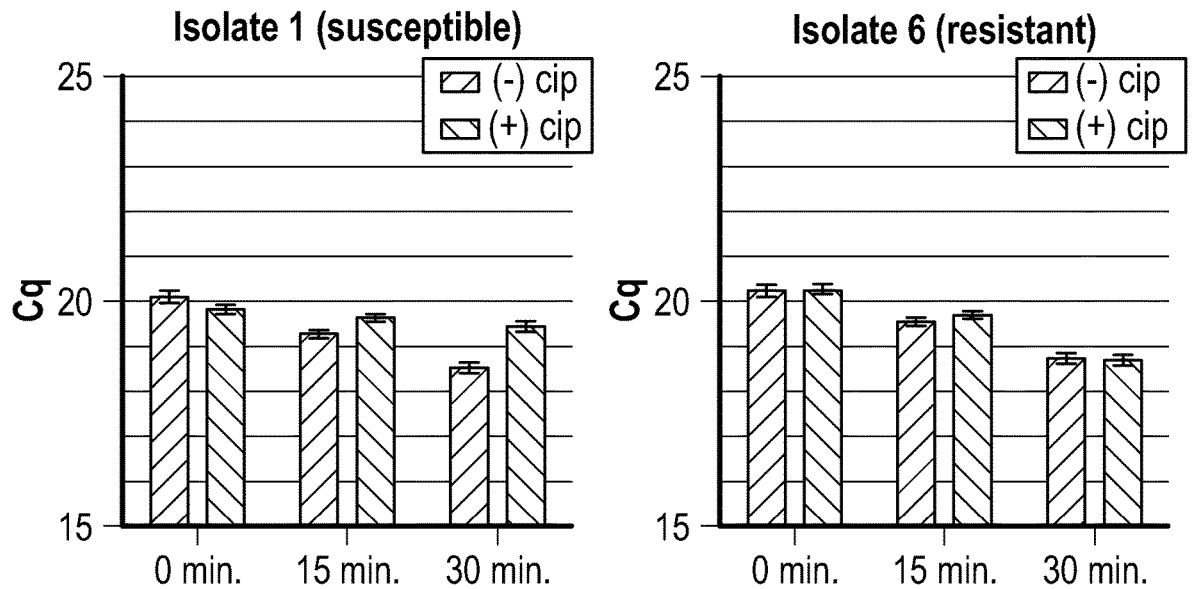
FIG. 12A shows the fold change in rDNA copy number for ciprofloxacin-susceptible *E. coli* treated with 2.5 ug/mL ciprofloxacin (right bar at each timepoint) and non-treated (left bar at each timepoint) samples measured at 0, 15, and 30 minutes as determined by qPCR.

Example 4: Detection of Differences in rDNA Between Treated/Untreated Susceptible and Resistant E. coli Over Time by qPCR and Digital PCR In one experiment, a ciprofloxacin-susceptible E. coli isolate from a patient with a urinary tract infection was pre-cultured in Bacto Brain Heart Infusion media to high cell density prior to dilution and treatment with and without 2.5 ug/mL ciprofloxacin for 30 minutes. DNA from treated and non-treated samples was extracted with Epicentre QuickExtract DNA extraction buffer at 0, 15, and 30 minutes. Quantitative PCR with primers specific to the target 23S rDNA gene as provided in Example 3 was performed on the extracted DNA. At 15 minutes, a 1.27 fold change in rDNA copy number between the treated (right bar at each timepoint) and non-treated (left bar at each timepoint) samples from the susceptible isolate was measured (FIG. 12A).

Figure 12B:
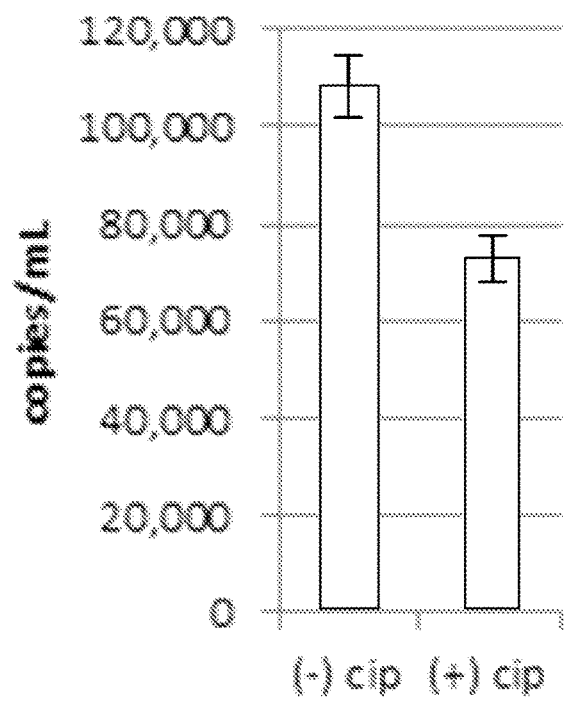
FIG. 12B shows the same as determined by digital PCR on a SlipChip.

Digital with primers specific to the target 23S rDNA gene as provided in Example 3 was performed on the extracted DNA in a SlipChip. One chip contained DNA from the untreated bacteria while the other chip contained DNA from the bacteria treated with antibiotic. The concentrations were compared and a fold-difference was calculated. Digital PCR detected a 1.5 fold change in rDNA copy number. No significant change in rDNA copy number was observed for the resistant isolate (FIG. 12B).

This experiment was repeated for a different E. coli isolate from a patient with a urinary tract infection which was also susceptible to ciprofloxacin. At 15 minutes, qPCR measured a 1.8 fold change in rDNA copy number and digital PCR detected a 1.5 fold change in rDNA copy number.

Figure 13:
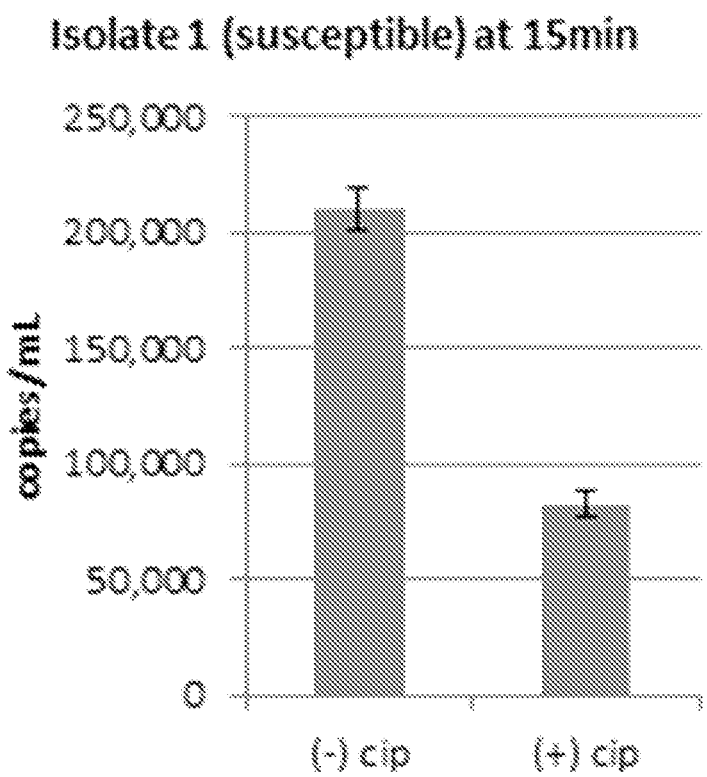
FIG. 13 shows the fold change in rDNA copy number for ciprofloxacin-susceptible *E. coli* treated with 0.75 ug/mL ciprofloxacin and non-treated samples measured at 15 minutes as determined by digital PCR on a SlipChip

Example 5: Detection of Differences in rDNA Between Treated/Untreated Susceptible E. coli Over Time by Digital PCR In one experiment, a ciprofloxacin-susceptible E. coli isolate from a patient with a urinary tract infection was pre-cultured in pooled human urine prior to dilution and treatment in 1:1 BHI:urine with and without 0.75 ug/mL ciprofloxacin for 15 minutes. DNA from treated and non-treated samples was extracted with Epicentre QuickExtract DNA extraction buffer. A 2.61 fold change in rDNA copy number between the treated and non-treated samples was measured using quantitative PCR on the extracted DNA with primers specific to the target 23S rDNA gene as provided in Example 3. Digital PCR was also performed using primers specific to the target 23S rDNA gene as provided in Example 3 on the extracted DNA. Digital PCR detected a 2.4 fold change in rDNA copy number. The results of the digital PCR data are shown in FIG. 13.

Figures 14A, 14B:
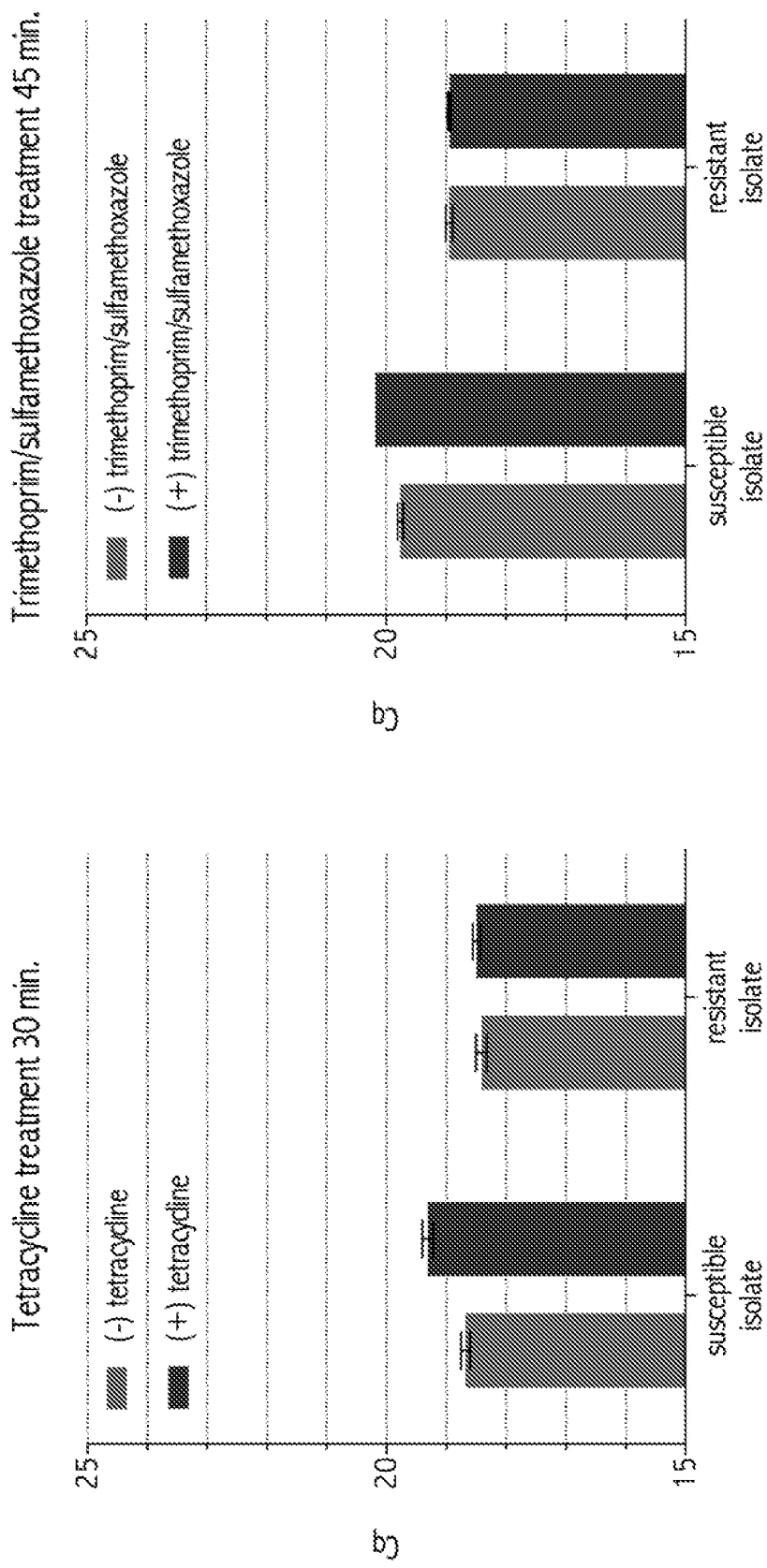
FIG. 14A shows the fold change in rDNA copy number for susceptible and resistant *E. coli* treated with tetracycline and non-treated samples measured at 30 minutes as determined by quantitative PCR.
FIG. 14B shows the fold change in rDNA copy number for susceptible and resistant *E. coli* treated with trimethoprim/sulfamethoxazole and non-treated samples measured at 45 minutes as determined by quantitative PCR

Example 6: Detection of Differences in Susceptible and Resistant E. coli Treated/Untreated with Tetracycline and Trimethoprim/Sulfamethoxazole In one experiment, E. coli isolates from patients with urinary tract infections and susceptible to various antibiotics were pre-cultured in BHI or urine prior to dilution and treatment in 1:1 BHI:urine with and without antibiotics for various treatment times. Treated and non-treated samples were extracted with Epicentre QuickExtract DNA extraction buffer. A detectable fold change in rDNA copy number between the treated and non-treated samples was measured using quantitative PCR with primers specific to the target 23S rDNA gene as provided in Example 3. Under tetracycline treatment a 1.55 fold change in rDNA copy number was observed at 30 minutes (FIG. 14A), under nitrofurantoin treatment a 1.62 fold change in rDNA copy number was observed at 15 minutes, and under trimethoprim/sulfamethoxazole treatment a 1.35 fold change in rDNA copy number was observed at 45 minutes (FIG. 14B).

Example 7: Comparison of qPCR and Digital PCR for Detection of Differences Between Resistant and Susceptible Cells In this example, the enhanced resolution of digital amplification over qPCR is shown. Specifically, differences in nucleic acids found in bacteria that have been treated with an antibiotic as compared to untreated can be resolved with digital nucleic acid quantification (including PCR or LAMP) whereas qPCR methods (or qLAMP) may not reliably resolve the difference and/or may not reliably resolve the difference without using many more replicates.

A ciprofloxacin-susceptible E. coli isolate from a patient with a urinary tract infection was pre-cultured in pooled human urine prior to dilution and treatment in 1:1 BHI:urine with and without 0.75 ug/mL ciprofloxacin for 30 minutes. DNA from treated and non-treated samples were extracted with Epicentre QuickExtract DNA extraction buffer.

Quantitative PCR was performed on each sample with primers specific to the target 32S rDNA gene (3 replicates per sample) with primers as provided in Example 3 and the following Cq's were obtained: treated—22.84+/−0.53; untreated—22.13+/−0.07. Using the method described in Weaver, et. al. "Taking qPCR to a higher level: Analysis of CNV reveals the power of high throughput qPCR to enhance quantitative resolution," Methods 2010 50: 271-276, this 1.6-fold difference in rDNA copy number is not statistically significant unless there had been 10 qPCR replicates for each sample instead of 3.

The same samples were diluted 1:10 and loaded into a SlipChip for digital amplification. One chip contained DNA from the untreated bacteria while the other chip contained DNA from the bacteria treated with antibiotic. Digital PCR was performed on the extracted DNA to amplify 23S rDNA using primers provided in Example 3.

The results were measured and the following concentrations were calculated using Poisson statistics: treated—148,031+/−7,103 copies/mL; untreated—84,964+/−5,171 copies/mL. Using the statistical methods described in Kreutz et al., "Theoretical Design and Analysis of Multivolume Digital Assays with Wide Dynamic Range Validated Experimentally with Microfluidic Digital PCR," Analytical Chemistry 2011 83: 8158-8168, a statistically significant difference with a p-value of 2e-13 was calculated.

Thus, digital PCR successfully resolved the treated vs. untreated bacterial DNA while qPCR was unable to resolve the difference in concentration with a typical number of replicates (three).

The statistical approach described with this experiment is applicable more generally. From a qPCR experiment, a standard deviation of 0.16 or greater in Cq is typical. In order to achieve a 1.25-fold resolution between two samples with this standard deviation, qPCR can require 18 replicates (Weaver et al. (2010)). For the same resolution (1.25), one digital PCR experiment can be performed, as long as the number of compartments in the digital PCR experiment is greater than 1200 (Id.).

Example 8: Target Mapping of Genes Relative to Origin of Replication

Figure 15:
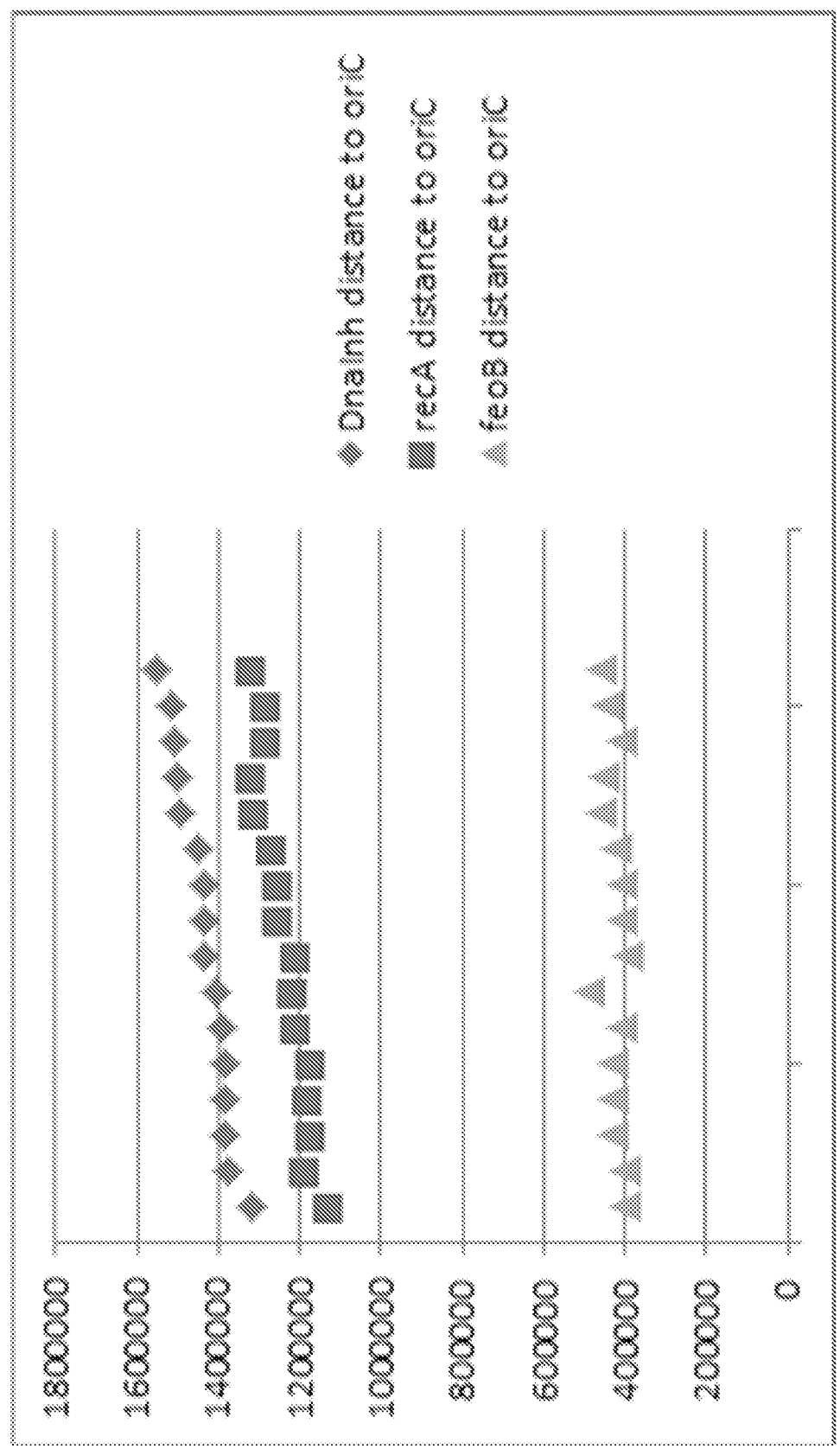
FIG. 15 shows the relative distance of feoB, recA and DnaInhibitor protein gene from oriC in genomes of UTI *E. coli* isolates. The x axis represents each individual genome (organized arbitrarily).

The position of feoB, recA, and DnaAInhibitor protein genes was mapped relative to the origin of replication in a subset of 16 available genome-sequenced E. coli strains linked to UTI patients. The results showed a trend for FeoB gene to be located in proximity to origin of replication, while recA and DnaAInhibitor protein genes are positioned more distantly from the origin of replication (FIG. 15). As a result of a replication initiation event, feoB gene is expected to replicate early, together with all other genes positioned close to origin of replication positioned at the similar distances from origin of replication as feoB gene (e.g., malB gene (GDB J01648)).

Example 9: DNA Markers in Different Time Points of Chromosomal Replication Data In this experiment, one susceptible UTI E. coli isolate and one resistant UTI E. coli were treated with 2.5 ug/mL ciprofloxacin for 15 minutes. Their nucleic acids were extracted with QuickExtra DNA extraction kit (Epicenter) and DNA was quantified via qPCR with rDNA (23S), FeoB gene, DnaA inhibiting protein gene, and RecA gene specific primers.

Figure 16:
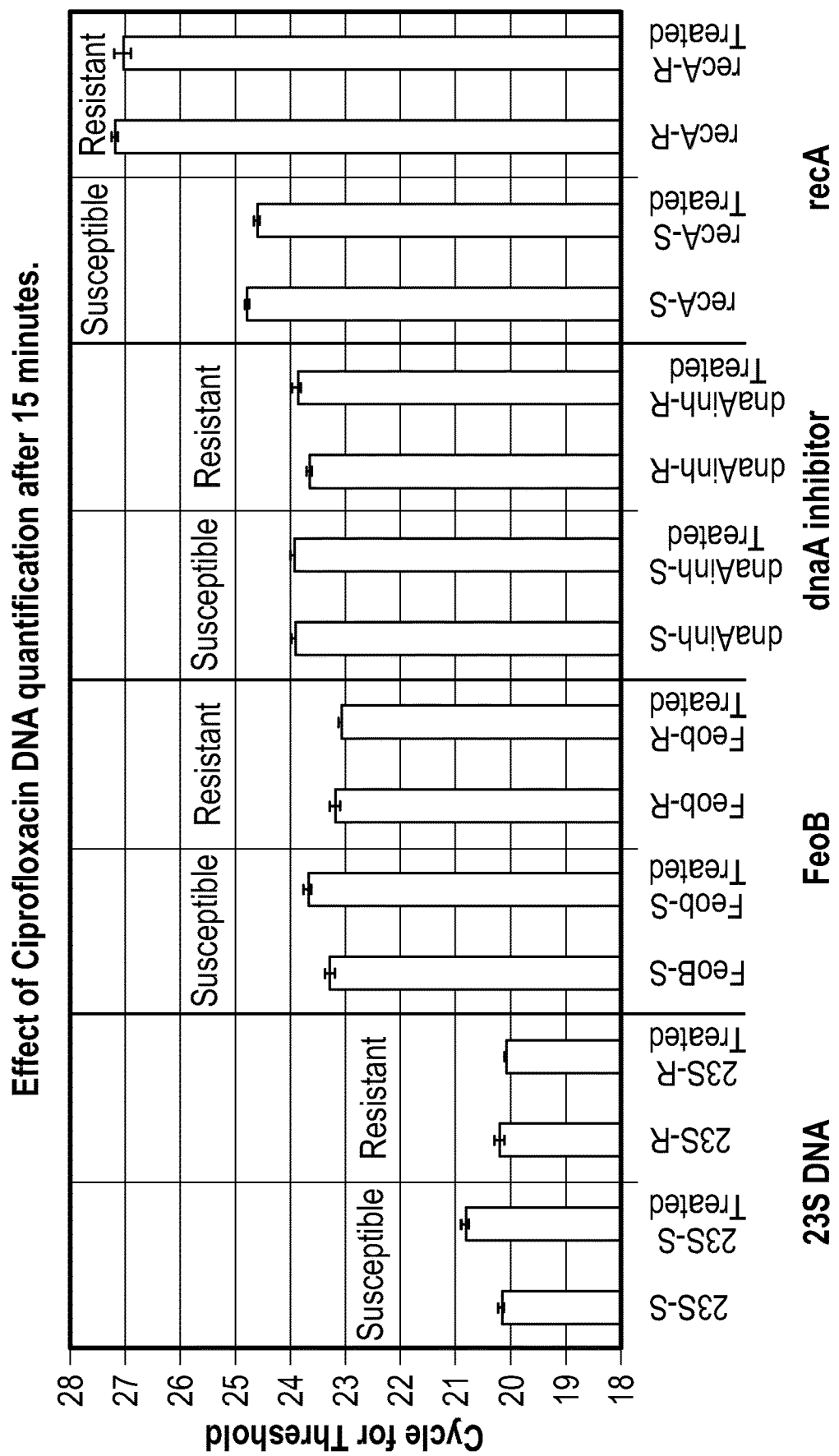
FIG. 16 shows Cycle threshold (Ct) for quantification of DNA fragments copies number in UTI clinical isolates *E. coli* genomes, in susceptible and resistant of bacteria (A) after exposure ("treated") to a 2.5 ug/ml of ciprofloxacin for 15 minutes in BHI medium.

FIG. 16 shows Cycle threshold (Ct) for quantification of DNA fragments copies number in UTI clinical isolates E. coli genomes, in susceptible and resistant of bacteria after exposure ("treated") to a 2.5 ug/ml of ciprofloxacin for 15 minutes in BHI medium. Table 2 provides the cycle threshold and fold change for each target between susceptible and resistant treated/untreated samples.

TABLE 2

|  | 23S CT Untreated/Treated | 23S Fold Change | FeoB Untreated/Treated | FeoB Fold Change | dnaAinh CT Untreated/Treated | dnaAinh Fold Change | recA CT Untreated/Treated | recA Fold Change |
|---|---|---|---|---|---|---|---|---|
| Susceptible | 20.19/20.84 | 1.57 | 23.3/23.71 | 1.33 | 23.93/23.97 | 1.03 | 24.81/24.65 | 0.89 (1.13 up) |
| Resistant | 20.22/20.13 | 0.94 (1.06 up) | 23.19/23.1 | 0.94 (1.06up) | 23.68/23.89 | 1.16 | 27.19/27.05 | 0.91 (1.10 up) |

In a susceptible strain, cells treated with ciprofloxacin showed a 1.57 fold decrease in 23S DNA, a 1.33 fold decrease in FeoB DNA, no change in dnaAinh DNA, and a 1.13 fold increase in recA compared to cells untreated with the antibiotic.

In a resistant strain, cells treated with ciprofloxacin showed no change in 23S DNA and FeoB DNA, a 1.16 fold decrease in dnaAinh DNA, and a 1.10 fold increase in recA compared to cells untreated with the antibiotic.

In this example, less rDNA (23S DNA) copies and less FeoB genes copies are observed in the genomes of the susceptible isolates as compared to the resistant isolates; while for other genes fragments—dnaA inhibitor genes and recA genes positioned more distantly from origin of replication, there was no statistically rigorous difference between drug treated and no treated bacteria.

Example 10—Target mRNA for Determining Drug Resistance or Susceptibility

Our drug susceptibility assay is validated using several targets of interest. These include the targets FeoB and RecA RNA in isolates resistant to ciprofloxacin Feo B expression is down-regulated in a presence of ciprofloxacin. Despite being downregulated at a low level it is down regulated in the bacteria which are susceptible (non-dividing, or dying) so it will ensure a good resolution compared to untreated or resistant cells.

In this example, FeoB and RecA RNA levels were used to determine cells that were susceptible or resistant to ciprofloxacin clinical isolates after 20 min of treatment with 2.5 ug/mL cipro in BHI medium. In this example, RNA quantification was done by qRTPCR with FeoB and RecA gene specific primers. In this example, FeoB expression was downregulated in susceptible isolates after antibiotic treatment. RecA expression in the same experiment was not significantly downregulated in susceptible isolates.

RNA ratios for feoB and recA allow to differentiate between susceptible and resistant UTI E. coli isolates after 20 minutes of antibiotic treatment.

In one example, one susceptible UTI E. coli isolate and one resistant UTI E. coli from overnight cultures were diluted in warm BHI medium 1:100 (10 µL in 1 mL), and grown for-3-4 hours at 37 C. Two samples of each well mixed culture were taken for antibiotic exposure assay. They were added to pre-warmed 1.7 mL VWR micro centrifuge tubes containing A) warm (37 C) BHI medium (control) or B) warm (37 C) BHI medium with added ciprofloxacin at concentration 2.5 µg/mL; the rack for all the tubes has being also pre-warmed to 37° C. to minimize the temperature variations. Both control and antibiotic containing samples were incubated for 20 minutes at 37° C. After that the samples A and B were immediately placed on ice, and were diluted 1/5 in RLT buffer (Qiagen). Their total nucleic acids were extracted using Qiagen RNAeasy Mini kit columns and buffers, and analyzed via one-step RT qPCR to quantify FeoB and Rec A RNA, using Maxima H-RT and SSO fast EvaGreen PCR mixture in a presence of 0.3 U/µL RNases inhibitor Superase In (Ambion) and 1 µg/µL BSA (Roche). Samples taken from resistant isolates are marked UTI R and samples taken from susceptible samples are marked UTI S in the plots below. Samples incubated in a presence of ciprofloxacin have "cipro" added to their names.

Figure 17A:
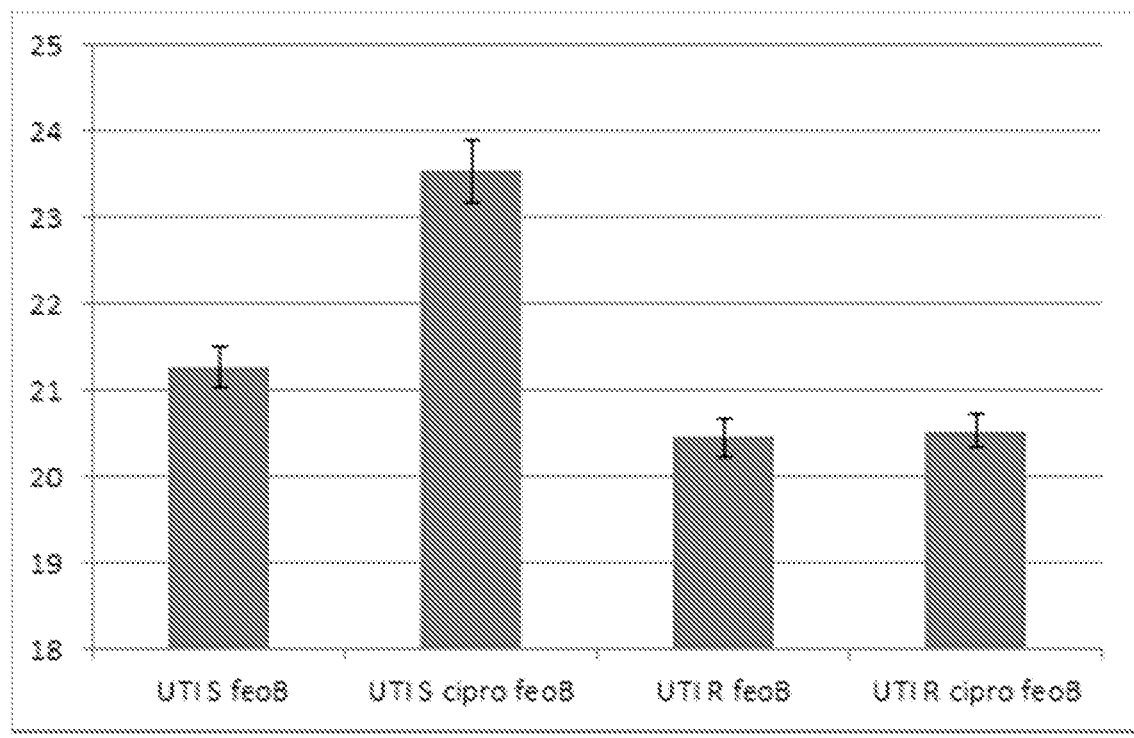
FIG. 17A and FIG. 17B show RNA quantification of FeoB and RecA genes expression in UTI clinical isolates susceptible (S) and resistant (R) to ciprofloxacin after 20 minutes of treatment with 2.5 ug/mL of ciprofloxacin in BHI medium, versus 20 minutes of being in BHI medium without antibiotics.
Figure 17B:
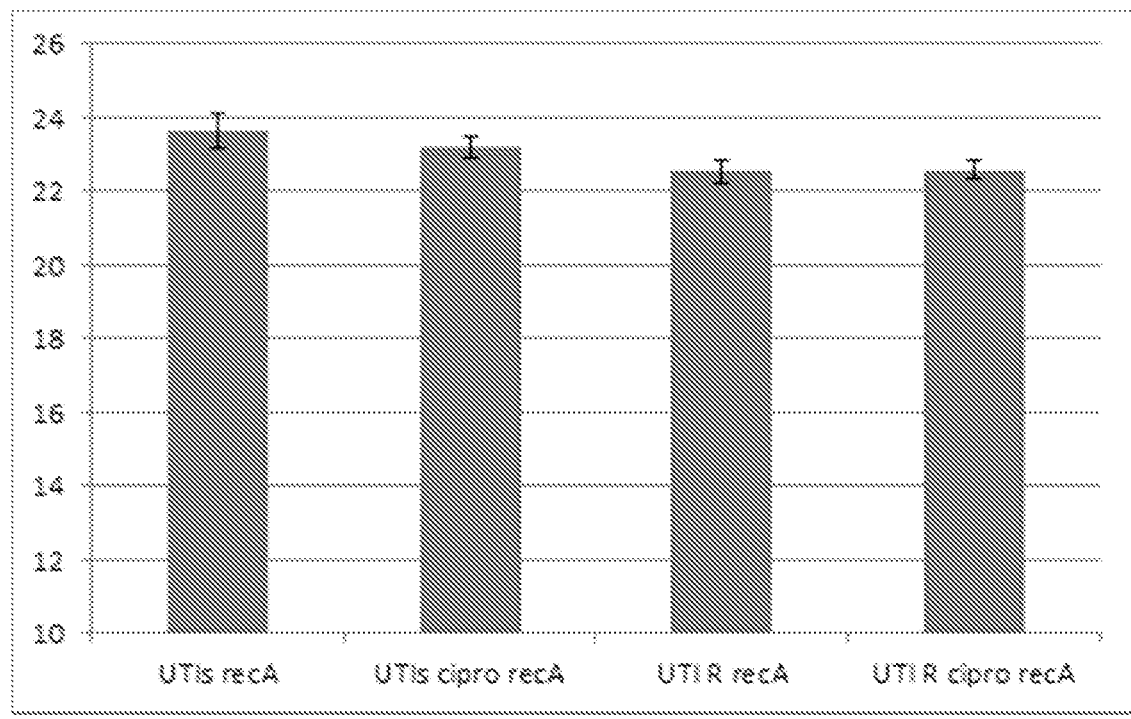

FIG. 17A and FIG. 17B show RNA quantification of FeoB and RecA genes expression in UTI clinical isolates susceptible (S) and resistant (R) to ciprofloxacin after 20 minutes of treatment with 2.5 ug/mL of ciprofloxacin in BHI medium, versus 20 minutes of being in BHI medium without antibiotics. Relative to susceptible cells exposed to ciprofloxacin, untreated susceptible cells showed a 4.86 fold increase in the expression of the FeoB target, observed as a 2.28 cycle difference. There was no significant change observed the gene expression in resistant cells. Both resistant and susceptible cells showed no significant changes in the expression of recA.

Example 11—Effects of Ciproflaxin on RNA Expression of FeoB and RecA

Clinical isolates from UTI patients were obtained and recovered on TSA blood agar medium. Colonies from the blood agar plates were inoculated into 3 mL of BHI medium, grown overnight. One susceptible UTI E. coli isolate and one resistant UTI E. coli from overnight cultures were diluted in warm BHI medium 1:100 (10 µL in 1 mL), grown for about 3 hours at 37 C. Two samples of each well mixed culture were taken for antibiotic exposure assay. They were added to pre-warmed 1.7 mL VWR micro centrifuge tubes containing A) warm (37° C.) BHI medium (control) or B) warm (37° C.) BHI medium with added ciprofloxacin at concentration 10 ug/mL; the rack for all the tubes has being also pre-warmed to 37° C. to minimize the temperature variations. Both control and antibiotic-containing samples were incubated for 20 minutes at 37° C. After that samples A and B were immediately placed on ice, and 30 µL of each sample were added to 130 µL of cold RLT buffer (Qiagen). Their total nucleic acids were extracted using Qiagen RNAeasy Mini kit columns and buffers, and analyzed via one-step RT qPCR to quantify FeoB and RecA RNA, using Maxima H-RT (and SSO fast EvaGreen PCR mixture in a presence of RNases inhibitors and BSA.

Figure 18:
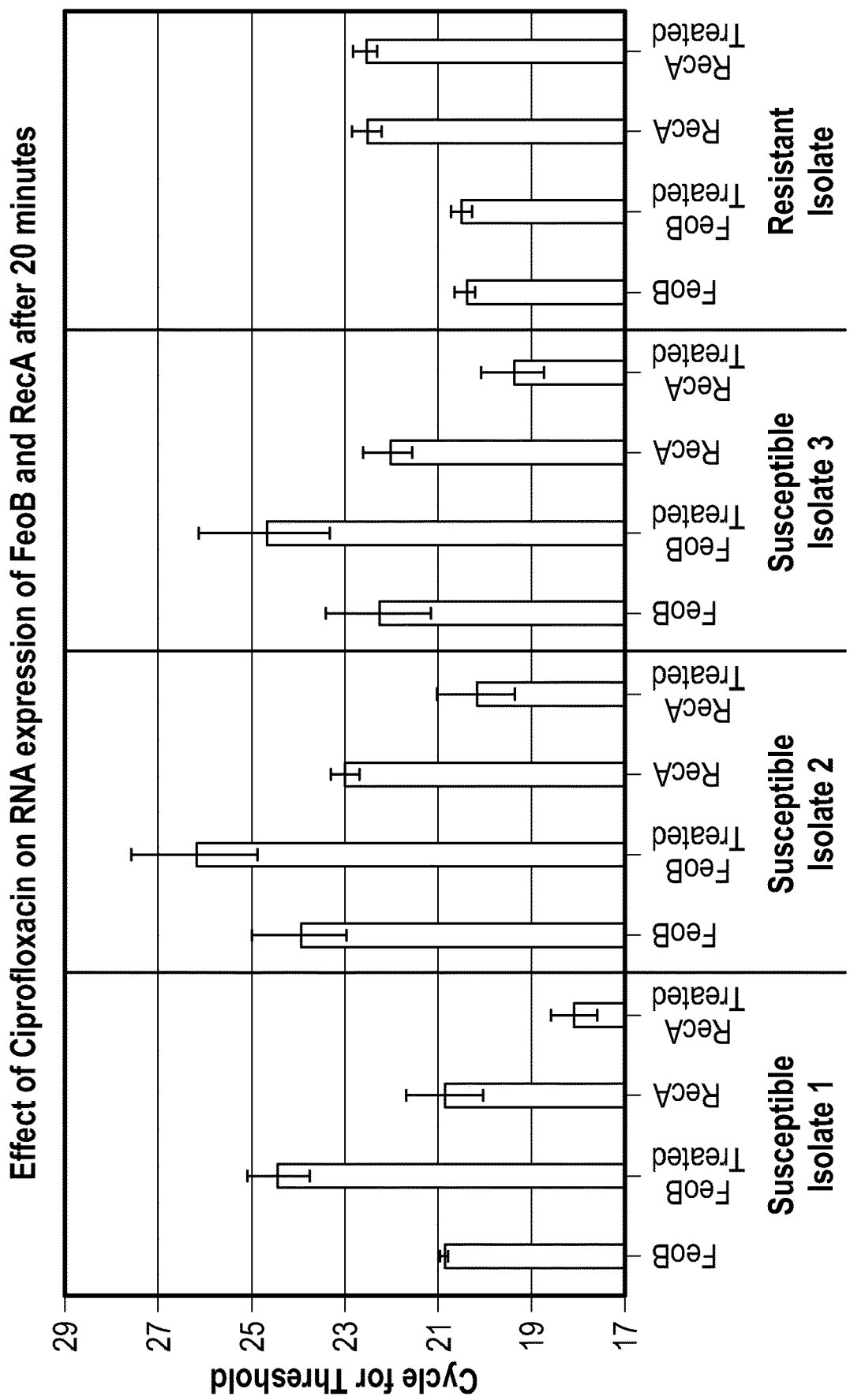
FIG. 18 shows RNA quantification of FeoB and RecA genes expression in UTI clinical isolates susceptible and resistant to ciprofloxacin after 20 minutes of treatment with 10 ug/mL of ciprofloxacin in BHI medium, versus 20 minutes of being in BHI medium without antibiotics.

FIG. 18 shows RNA quantification of FeoB and RecA genes expression in UTI clinical isolates susceptible and resistant to ciprofloxacin after 20 minutes of treatment with 10 ug/mL of ciprofloxacin in BHI medium, versus 20 minutes of being in BHI medium without antibiotics. Results are provided in Table 3.

TABLE 3

|  | FeoB | | RecA | | |
| --- | --- | --- | --- | --- | --- |
|  | CT Untreated/ Treated | Fold Change Downregulated | CT Untreated/ Treated | Fold Change Upregulated | Fold Change Ratio |
| Susceptible 1 | 20.88/24.45 | 11.88 | 20.87/18.11 | 6.77 | 80.45 |
| Susceptible 2 | 23.99/26.21 | 4.66 | 23.00/20.21 | 6.91 | 32.22 |
| Susceptible 3 | 22.28/24.73 | 5.46 | 22.08/19.42 | 6.32 | 34.54 |
| Resistant | 20.45/20.53 | 1.06 | 22.54/22.57 | 0.98 | 1.04 |

Relative to susceptible cells untreated with ciprofloxacin, susceptible cells treated showed significant downregulation of the FeoB gene. Three different susceptible isolates showed 11.88, 4.66, and 5.46 fold decrease in the presence of this RNA in cells. A resistant isolate showed no significant change. Relative to susceptible cells untreated with ciprofloxacin, susceptible cells treated showed significant upregulation of the RecA gene. Three different susceptible isolates showed 6.77, 6.92, and 6.32 fold increase in the presence of this RNA in cells. A resistant isolate showed no significant change. Individually either of these changes can be used to distinguish susceptible from resistant cells, however, taking a ratio of the change in FeoB to RecA provides even greater resolution between the resistant and susceptible cells. The susceptible strains tested showed an 80.45, 32.22, and 34.54 fold change ratio, whereas in resistant cells, this ratio was 1.04.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method, comprising:
    providing a first sample comprising a target molecule from a first portion of a population of bacteria and a second sample comprising a target molecule from a second portion of said population of bacteria, wherein the first portion has been treated with an antibiotic for a period of no more than 2 hours, and wherein the second portion has not been treated with the antibiotic;
    distributing said first sample among a plurality of first analysis regions;
    distributing said second sample among a plurality of second analysis regions;
    contacting each of the first and second analysis regions with a reagent for performing a reaction to detect the presence or absence of a threshold number of target molecules in each of the first and second analysis regions, wherein the target molecules comprise a segment of a bacterial chromosome or plasmid, wherein the segment of the bacterial chromosome or plasmid is contacted with the reagent in at least some of the first and second analysis regions; and detecting the presence or absence of the threshold number of target molecules in each of the first and second analysis regions, wherein the distribution of each sample among the analysis regions is effected such that the threshold number of target molecules is detected in some of the first and second analysis regions and is not detected in some of the first and second analysis regions after said reaction.

2. The method of claim 1, wherein the threshold number is greater than zero, one, two, three, four, or five.

3. The method of claim 1, wherein the distribution of each sample among the analysis regions is effected such that at least some of the analysis regions do not have the target molecule, and at least some of the analysis regions have only one target molecule.

4. The method of claim 1, wherein the distribution of each sample among the analysis regions is effected such that at least one of the analysis regions contains only one target molecule.

5. The method of claim 1, wherein the first sample comprises said reagent, and wherein contacting the plurality of first analysis regions with the reagent comprises said step of distributing said first sample among said plurality of first analysis regions.

6. The method of claim 1, wherein the second sample comprises said reagent, and wherein contacting the plurality of second analysis regions with the reagent comprises said step of distributing said second sample among said plurality of second analysis regions.

7. The method of claim 1, wherein said reaction comprises nucleic acid amplification.

8. The method of claim 1, wherein the reagent is disposed in a plurality of reagent regions.

9. The method of claim 8, wherein contacting is effected by placing the plurality of reagent regions in fluid communication with the first or second plurality of analysis regions.

10. The method of claim 9, wherein contacting comprises effecting relative motion between a substrate comprising the reagent regions with a substrate comprising the first and second plurality of analysis regions.

11. The method of claim 1, further comprising analyzing the detection of the presence or the absence of the threshold number of target molecules in each plurality of analysis regions to determine a resistance or susceptibility to an antibiotic in the population of bacteria.

12. The method of claim 1, wherein said detection of the presence or absence of the threshold number of target molecules in each of the first and second analysis regions is performed less than 3 hours, 2 hours, or one hour after the end of exposure of the first sample to the antibiotic.

13. The method of claim 12, wherein said detection of the presence or absence of the threshold number of target molecules in each of the first and second analysis regions is performed less than 45 minutes, 30 minutes, 15 minutes, or 10 minutes after the end of exposure of the first sample to the antibiotic.

14. The method of claim 1, wherein said bacteria from said first sample have been treated with antibiotic for a period of no more than 1 hour, no more than 45 minutes, no more than 30 minutes, no more than 15 minutes, or no more than 10 minutes.

15. A method of determining a resistance or susceptibility to an antibiotic in a population of bacteria, comprising:
providing a first sample comprising a target molecule from a first portion of a population of bacteria and a second sample comprising a target molecule from a second portion of said population of bacteria, wherein the first portion has been treated with an antibiotic for a period of no more than 2 hours, and wherein the second portion has not been treated with the antibiotic;
distributing said first sample among a plurality of first analysis regions;
distributing said second sample among a plurality of second analysis regions;
contacting each of the first and second analysis regions with a reagent for performing a reaction to detect the presence or absence of a threshold number of target molecules in each of the first and second analysis regions, wherein the target molecules comprise a segment of a bacterial chromosome or plasmid, wherein the segment of the bacterial chromosome or plasmid is contacted with the reagent in at least some of the first and second analysis regions;
detecting the presence or absence of the threshold number of target molecules in each of the first and second analysis regions, wherein the distribution of each sample among the analysis regions is effected such that the threshold number of target molecules is detected in some of the first and second analysis regions and is not detected in some of the first and second analysis regions after said reaction; and
determining a resistance or susceptibility to said antibiotic in the population of bacteria from the results of said detection in each of the first and second analysis regions.

16. The method of claim 15, wherein said bacteria from said first sample have been treated with antibiotic for a period of no more than 1 hour, no more than 45 minutes, no more than 30 minutes, no more than 15 minutes, or no more than 10 minutes.

17. The method of claim 15, wherein said reaction comprises nucleic acid amplification.

18. A method, comprising:
providing a first sample comprising a target analyte from a first portion of a population of cells and a second sample comprising a target analyte from a second portion of said population of cells, wherein the first portion has been treated with a drug for a period of no more than 2 hours, and wherein the second portion has not been treated with the drug;
distributing said first sample among a plurality of first analysis regions;
distributing said second sample among a plurality of second analysis regions;
contacting each of the first and second analysis regions with a reagent for performing a reaction to detect the presence or absence of a threshold number of target analytes in each of the first and second analysis regions, wherein the target analytes comprise a segment of a bacterial chromosome or plasmid, wherein the segment of the bacterial chromosome or plasmid is contacted with the reagent in at least some of the first and second analysis regions; and
detecting the presence or absence of the threshold number of target analytes in each of the first and second analysis regions, wherein the distribution of each sample among the analysis regions is effected such that the threshold number of target analytes is detected in some of the first and second analysis regions and is not detected in some of the first and second analysis regions after said reaction.

19. The method of claim 18, wherein said cells from said first sample have been treated with said drug for a period of no more than 1 hour, no more than 45 minutes, no more than 30 minutes, no more than 15 minutes, or no more than 10 minutes.

20. The method of claim 18, wherein said reaction comprises nucleic acid amplification.

\* \* \* \* \*